1

United States Patent [19]

Fitchen et al.

[11] Patent Number: 5,955,647
[45] Date of Patent: Sep. 21, 1999

[54] METHOD FOR USING TOBACCO MOSAIC VIRUS TO OVERPRODUCE PEPTIDES AND PROTEINS

[75] Inventors: John H. Fitchen; Roger N. Beachy, both of La Jolla, Calif.

[73] Assignee: The Scripps Research Institute, La Jolla, Calif.

[21] Appl. No.: 08/687,559

[22] PCT Filed: Feb. 3, 1995

[86] PCT No.: PCT/US95/01467

§ 371 Date: Nov. 18, 1996

§ 102(e) Date: Nov. 18, 1996

[87] PCT Pub. No.: WO95/21248

PCT Pub. Date: Aug. 10, 1995

Related U.S. Application Data

[63] Continuation-in-part of application No. 08/192,477, Feb. 3, 1994, abandoned.

[51] Int. Cl.$^6$ .............................. A01H 5/00; C07K 1/14; C12N 7/01; C12N 7/04; C12N 15/40; C12N 15/82

[52] U.S. Cl. .................. 800/205; 435/172.1; 435/172.3; 435/235.1; 435/236; 530/412; 536/23.72; 800/DIG. 9; 800/DIG. 13; 800/DIG. 25; 800/DIG. 40; 800/DIG. 42; 800/DIG. 43; 800/DIG. 44

[58] Field of Search .............................. 435/320.1, 69.1, 435/69.7, 172.3, 235.1, 236, 172.1; 536/23.72; 800/205, DIG. 43, DIG. 9, DIG. 13, DIG. 25, DIG. 40, DIG. 42, DIG. 44; 530/412

[56] References Cited

U.S. PATENT DOCUMENTS 5,618,699    4/1997    Hamamoto et al. ................ 435/69.7

OTHER PUBLICATIONS

Hamamoto H, et al. "A new tobacco mosaic virus vector and its use for the systemic production of angiotensin–1–converting enzyme inhibitor in transgenic tobacco and tomato." Bio/Technology 11: 930–932, Aug. 1993.

Holt CA, et al. "In vivo complementation of infectious transcripts from mutant tobacco mosaic virus cDNAs in transgenic plants." Virology 181: 109–117, 1991.

Citovsky, et al., Nuclear Localization of Agrobacterium VirE2 Protein in Plant Cells, Jun. 26, 1992, *Science*, 256: 1802–1805.

Bruening, et al., In Vitro and In Vivo Translation of the Ribonucleic Acids of a Cowpea Strain of Tobacco Mosaic Virus, 1976, *Virology*, 71:498–517.

Takamatsu, et al., Production of Enkephalin in Tobacco Protoplasts Unsing Tobacco Mosaic Virus RNA Vector, Aug. 1990, *Federation of European Biochemical Societies*, No. 1, 269:73–76.

Dawson, et al., Modifications of the Tobacco Mosaic Virus Coat Protein Gene Affecting Replication, Movement, and Symptomatology, 1988, *The American Phytopathological Society*, No. 6, 78:783–789.

Culver, et al., Virus–Host Interactions: Induction of Chlorotic and Necrotic Responses in Plant by Tobamoviruses, 1991, *Annu. Rev. Phytopathol*, 29:193–217.

Haynes, et al., Development of a Genetically–Engineered, Candidate Polio Vaccine Employing the Self–Assembling Properties of the Tobacco Mosaic Virus Coat Protein, Jul. 1986, *Bio/Technology*, 4:637–641.

Holt & Beachy, In Vivo Complementation of Infectious Transcripts from Mutant Tobacco Mosaic Virus cDNAs in Transgenic Plants, 1991, *Virology*, 181:109–117.

Hamamoto, et al., A New Tobacco Mosaic Virus Vector and its Use for the Systemic Production of Angiotensin–I–Converting Enzyme Inhibitor in Transgenic Tobacco and Tomato, Aug. 1993, *Bio/Technology*, vol. 11, pp. 930–932.

*Primary Examiner*—Douglas W. Robinson
*Assistant Examiner*—Amy J. Nelson
*Attorney, Agent, or Firm*—Thomas Fitting; Emily Holmes

[57] ABSTRACT

The invention describes an infectious modified Tobacco Mosaic Virus (TMV) virion comprising a modified coat protein (CP) having a heterologous peptide inserted between amino acid residues 154 and 155 of CP. Also described is an infectious TMV virion having a modified movement protein (MP). The invention further describes nucleotide sequences encoding the modified TMV virion with either a modified CP or modified MP, and methods for producing the heterologous peptide in plants using the nucleotide sequences and modified virions.

33 Claims, 23 Drawing Sheets

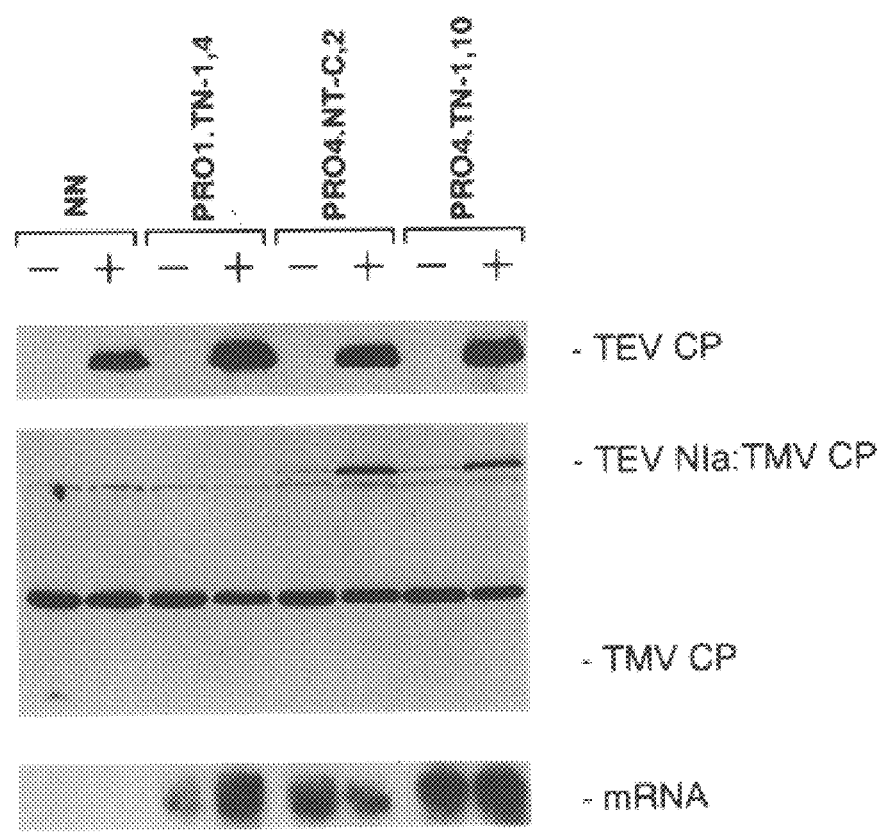

anti-ZP3 rat monoclonal

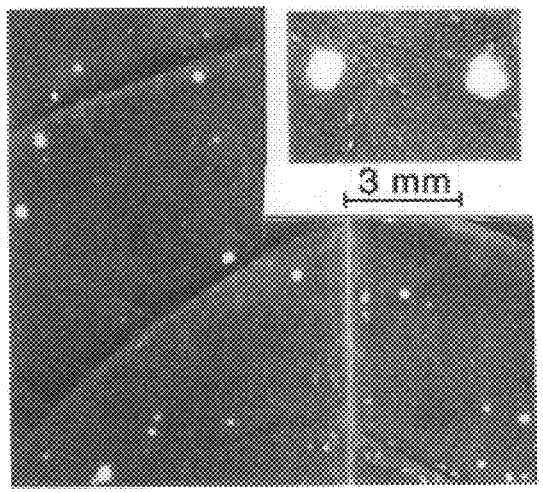
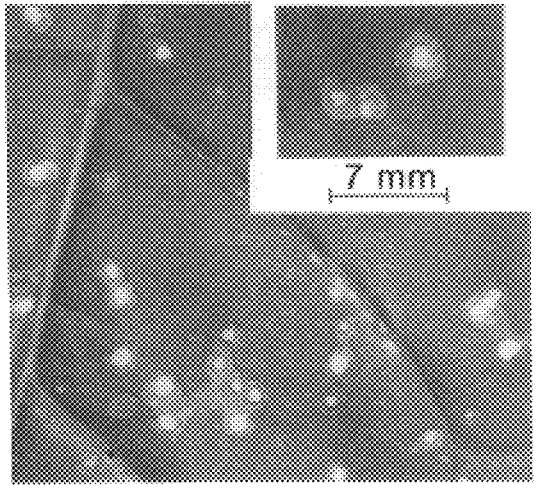
FIG. 16D  FIG. 16E
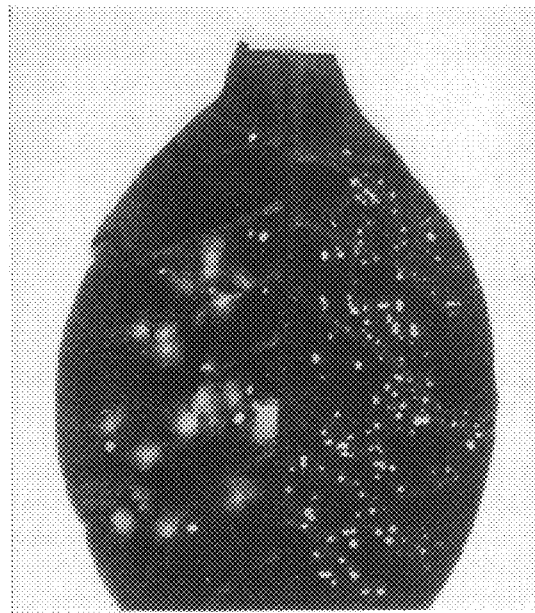
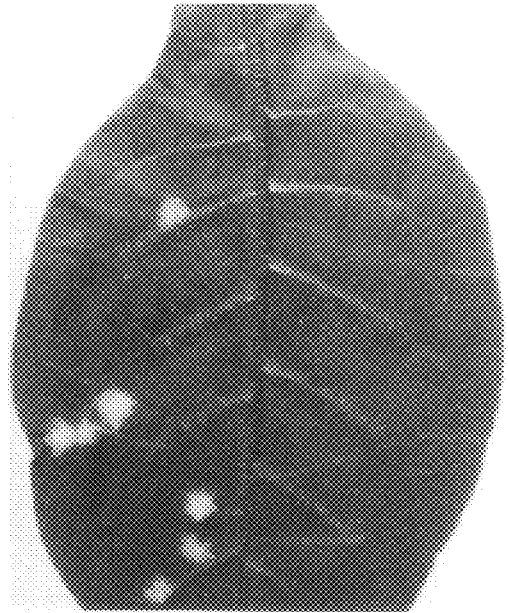
FIG. 16F  FIG. 16G

METHOD FOR USING TOBACCO MOSAIC VIRUS TO OVERPRODUCE PEPTIDES AND PROTEINS

This application is a Continuation-in-Part application of U.S. Ser. No. 08/192,477, filed Feb. 3, 1994, now abandoned.

This study was supported in part by US Public Health Service grants DK43888, AI27161 and R01-AI-27161-05A1 from the National Institutes of Health and by NSF grants MCB-9209530, MCB-9220176, and MCB-9317368. The Government of the United States may have substantial interest in this property. This invention was made with government support under Contract No. R01-A1-27161-07 by the National Institute of Health. The government has certain rights in the invention.

BACKGROUND OF THE INVENTION

1. Field of the Invention

This invention relates to methods for production of recombinant peptides and proteins. More particularly, this invention relates to techniques for inserting peptides into the coat protein of a virus, particularly for purposes of creating a vaccine.

2. Description of Related Art

Tobacco mosaic virus (TMV) is a well-characterized plant virus with a single, positive-sense RNA genome of 6395 nucleotides. The sequence of the TMV coat protein was initially derived back in the 1950's, and it was not until 1972 that the structure and roles of the forms of the TMV CP, its assembly and microscopic examination of the polymers were published (Durham, et al., *J. Mol. Bio.*, 67:315–332 and 67:307–314). In 1982 the full genomic sequence of TMV RNA was published, and confirmation of the amino acid sequence of the CP as derived from the sequence of the viral RNA was confirmed (Goelet, et al., *Proc. Natl. Acad. Sci. USA*, 79:5818–5822, 1982). The 126 and 183-kDa proteins, which are required for virus replication (Ishikawa, et al. *Nucleic Acids Res.* 14:8291–8305, 1985) are translated directly from the genomic RNA from the same initiation codon. The 30 kDA movement protein (MP), which is involved in cell-to-cell movement, and the 17.5 kDA coat protein (CP) are translated from separate 3' coterminal subgenomic mRNAs (Siegel, et al., *Proc. Nat. Acad. Sci. USA*, 48:1845–1851, 1976; R. N. Beachy, et al., *Virology*, 63:84–97, 1975.

The life cycle of the TMV virus is well known. The amount of mRNA for the viral proteins determines the amount of each protein produced. The protein produced in the largest amount is the CP, which is as much as 5–10% of the total protein made in the infected cell. The structure of the TMV CP is reviewed in Butler, et al,. (*J. of General Virology*, 65:253–279, 1984). The CP encapsidates the viral RNA and is required for long-distance movement in the plant. The CP drives the assembly and encapsidation, which in turn enables systemic spread (Dawson, et al., *Phytopathology*, 78:783–789, 1988). Viral assembly and encapsidation are not required for local cell to cell spread of the viral RNA; however, the MP protein, a non-structural protein encoded by the virus, is required for local cell to cell spread of the viral RNA.

A number of research projects have been conducted to establish the use of TMV as a potential vector by inserting peptides into the coat protein. Even before the cloned cDNA of TMV was available, Haynes, et al. (*Bio/Technology*, 4:637–641, 1986) attached additional nucleotides at the 3' end of the coat protein mRNA, resulting in production of a fusion protein carrying sequences to serve as a vaccine for polio virus. The fusion CP was able to assemble and form rod-like structures in *E. coli*. Because the cDNA was unavailable, no work was done in a plant system.

The development of in vitro expression systems that allow production of infectious TMV RNAs from cloned full length cDNA genomes (Dawson, et al., *Proc. Natl. Acad. Sci. USA*, 83:1832–1836, 1986; Meshi, et al., *Proc. Natl. Acad. Sci. USA*, 83:5043–5047, 1986) has permitted the direct manipulation of the TMV genome at the DNA level. Highly infectious RNA transcripts of a full-length infectious cDNA clone of the U1 (common) strain of TMV have been produced in vitro using bacteriophage T7 RNA polymerase (Holt and Beachy, *Virology* 181:109–117, 1991) Thus, TMV RNA is a good candidate as a vector for the expression of foreign genes in plants. However, the TMV vectors developed using a CP gene modified to insert foreign genes usually fail to systemically express foreign genes, either through failure to produce intact CP for virus particle formation, or through loss of the foreign gene sequence during replication due to RNA recombination (N. Takamatsu, et al., *EMBO J.*, 6:306–311, 1987; N. Takamatsu, et al, *FEBS Lett.*, 2:73–76, 1989; W. O. Dawson, et al., *Virology*, 172:285–292, 1989). One exception is the TMV-ORSV (odontoglossum ringspot virus) hybrid vector, which includes an ORSV CP as an additional intact CP gene, thereby avoiding RNA recombination (J. Donson, et al., *Proc. Natl. Acad. Sci. USA*, 88:7204–7208, 1991). Successful systemic expression was achieved more recently by inserting the "weak" stop codon for the TMV 130 K protein gene, which permits readthrough of the stop codon, immediately after the stop codon for the CP gene and immediately 5' of a foreign gene sequence encoding a 12 amino acid Angiotensin -I-Converting Enzyme Inhibitor (H. Hamamoto et al., *Bio/Technology* 11:930–932, 1993). Since readthrough occurred relatively rarely, the result was production of a small amount of intact CP as well as the CP fusion protein.

In 1990, a CP fusion protein was described (Takamatsu, et al., *FEBS Letters*, 269:73–76, 1990) containing a five amino acid sequence for enkephalin as a carboxyterminal fusion on the TMV CP. The carboxyl terminus of the CP is known to project from the capsid surface. A methionine sequence placed between the end of the CP and the enkephalin sequence was introduced for isolation of enkephalin in a cyanogen bromide cleavage reaction. During virus infection, a large accumulation in plant cells of virus protein of the expected size was observed. However, there was no evidence at this point that the protein could be assembled into virus particles except that one of the coat protein fusion sequences led to systemic symptoms. Other virus showed no systemic mosaic symptoms. Despite these barriers to systemic plant infection with the fusion protein, in infected protoplasts large amounts of the enkephalin fusion protein was produced, and the cyanogen bromide released the protein.

The movement protein of TMV has been studied to determine its function (Deom, et al., *Cell*, 69:221–224, 1992). The mechanism by which the movement protein functions to cause systemic invasion of the virus is unknown. Infection of a plant can be divided into several steps: (i) infection of the first cell; (ii) establishment of a multicellular infection site; (iii) short-distance or cell-to-cell spread through a leaf, which requires the MP; (iv) long-distance spread, which can be subdivided into entry into, travel through, and exit from the vascular system, and which has been shown to involve the CP in *Nicotiana tabacum* (W. O. Dawson, et al., *Phytopathology* 78:783–789, 1988; T. Saito et al., *Virology* 176:329–336, 1990; Takamatsu et al., *EMBO J.* 6:307–311, 1987), and (v) further cell-to-cell spread once the virus has left the vascular system.

The movement protein has a direct effect on the function of plasmodesmata. The molecular size exclusion limit of plasmodesmata in transgenic Xanthi tobacco plants expressing the MP gene from the cauliflower mosaic virus (CaMV) 35S promoter has been shown to be at least 10-fold greater than that in control plants (S. Wolf et al., *Science* 246:377–379, 1989). In addition, electron microscopy employing immunogold labeling has shown that the MP is localized in plasmodesmata in tobacco leaf tissue from TMV-infected plants (K. D. Tomenius et al., *Virology* 160:363–371, 1987) and in transgenic plants (D. Atkins et al., *J. Gen. Virol.* 72:207–211, 1991; B. Ding et al., *Plant Cell* 4:915–928, 1992; P. J. Moore et al., *Protoplasma* 170:115–127, 1992). MP produced in and purified from *Escherichia coli* binds single stranded nucleic acids in vitro in a cooperative but non-specific manner and forms a thin extended structure (V. Citovsky et al., *Plant Cell* 4:397–411, 1992). *E. coli*-produced MP, when injected into a tobacco mesophyll cell, can increase the plasmodesmal size exclusion limit of that cell and of adjacent cells, suggesting that the MP may be able to move from cell to cell in the absence of virus (E. Waigmann et al., *Proc. Natl. Acad Sci USA* 91:1433–1437, 1994). The tissues through which TMV must spread in order to successfully infect a plant are not known, In addition, it is not known in which tissues or in what quantities MP must accumulate in order for local or long-distance spread of the virus to occur.

When a frameshift mutation designed to cause premature termination of translation was introduced into the 30 kDa movement protein gene or the coat protein gene, the MP-frameshift mutant was unable to locally or systemically infect inoculated tobacco plants (Meshi, et al., *EMBO J.*, 6:2557–2563, 1987). However, inoculation of transgenic tobacco plants that expressed a wild-type TMV MP gene resulted in both local and systemic viral infection (Deom et al., supra). Thus, although the MP-frameshift mutant was unable to move systemically in nontransformed tobacco, systemic movement was detected in transgenic plants that expressed a wild-type TMV MP gene. Transgenic tobacco plants that expressed the appropriate wild-type TMV gene were thus able to complement, in trans, mutant viruses lacking a functional MP or CP gene. (Holt and Beachy, *Virology*, 181:109–117, 1991).

Systemic infection of plants with a virus vector containing DNA encoding a foreign protein promises an economical means for obtaining unlimited yields of recombinant proteins, which can be recovered by processing the leaves and other plant parts to recover the product protein. Therefore, despite the current advances in the art, the need exists for new and improved methods utilizing the TMV virus vector as a means for producing foreign proteins, such as viral vaccines, in planta.

The murine zona pellucida is composed of 3 sulfated glycoproteins and functions in the fertilization of the egg by providing a substrate for sperm binding (J. D. Bleil et al., *Devel. Biol.* 76, 185, 1980; S. Shimizu et al. *J Biol Chem* 258:5858, 1983).

One of the three glycoproteins, ZP3, is the primary binding site for the sperm (J. D. Bleil et al., *Cell* 20:873, 1980) and has been investigated as a target for immune contraception. Murine ZP3 antigens have been demonstrated to induce antibody mediated contraception (A. G. Sacco, *J. Rep. Fert.* 56:533, 1979; B. S. Dunbar in: J. F. Hartmann, Ed., *Mechanism and Control of Animal Fertilization,* Academic Press, N.Y., 1983, p. 140; I. J. East et al., *Devel. Biol.* 109:268, 1985; S. E. Millar et al., *Science* 246:935, 1989) as well as autoimmune oophoritis in mice. Resolution of these two responses is demonstrated in some genotypes of mice after immunization with ZP3 peptide vaccines (S. H. Rhim et al. *J. Clin. Invest.* 89:28, 1992; Y. Lou et al. *J. Clin. Invest.* 89:28, 1992; A-M. Luo et al., *J. Clin. Invest.* 92:2117, 1993) and by passive immunization with a monoclonal antibody which recognizes a murine ZP3 epitope defined by amino acids 336–342 (I. J. East et al., *Devel. Biol.* 109:268, 1985; S. E. Millar et al., supra). Several of the above investigations have focused on peptides of ZP3 in the region of amino acid residues 328 to 343 which contains epitopes independently associated with antibody mediated contraception and with autoimmune oophoritis. In this region a T-cell epitope identified with severe oophoritis, $ZP3_{330-336}$, overlaps the domain of a B-cell epitope, $ZP3_{336-342}$ responsible for antibody mediated contraception. Oophoritis and antibody mediated contraception are clearly genotype restricted. Antibodies raised against a 16 amino acid peptide, $ZP3_{328-343}$, conjugated to KLH resulted in the formation of contraptive antibodies in Swiss female mice with no appearance of ovarian disease (Millar et al., supra). Other strains (BALB/cBy, {C57BL/6J X A/J}F1, or A/J) developed ovarian disease when immunized parenterally with free peptides containing $ZP3_{330-346}$ while Swiss or C57BL/6J mice failed to develop oophoritis (Rhim et al., supra; Luo et al., supra).

As producers of protein antigens, plants provide a unique resource for generating an inexpensive supply of bulk protein with virtually universal access. Transgenic proteins or viral proteins produced in plant tissues provide a facile system for expression of subunit vaccines based on protein antigens (R. Usha, et al., *Virology,* 197:366, 1993; H. S. Mason, et al., *Proc. Natl. Acad Sci. (USA)* 89:11745, 1993). The tobacco mosaic virus (TMV) is a potential candidate as an epitope carrier since it is a self assembling virus which aggregates into rod like particles that accumulate in virus infected leaves. The protein component of the assembled particle is the coat protein (TMV CP), which is robust and tolerates modification in its carboxy terminal domain to carry non-TMV epitopes as disclosed herein. The TMV CP assembled TMV particles exhibit many characteristics of an ideal antigen system. The TMV CP has been shown to be immunogenic (N. Takamatsu, et al., *F.E.B.S. Letts.,* 269:73, 1990) and likely contains helper T-cell epitopes which could function for chimeric epitopes. The virus can be produced at high concentrations and isolated at low cost, and genetic stocks of the virus can be easily maintained for long periods of time without passaging through plants. In addition, coat protein antigens can be isolated and presented in particulate or aggregate form. This particulate nature of TMV based antigens could be advantageous for maintaining high local concentrations of antigen in parenteral immunizations (F. Loor, et al., *Virology,* 33:215, 1967) and may be useful in stimulating mucosal immune responses to orally ingested antigens.

Accordingly, the present invention provides a method for producing in a plant a viral vaccine or an immunogene peptide capable of raising a contraceptive immune response in a mammal.

SUMMARY OF THE INVENTION

A method is provided for overexpression in plants of heterologous peptides of from about 5 to 20 amino acids as fusion proteins inserted near, but preferably not at the carboxy terminus of the coat protein of tobacco mosaic virus using a modified cDNA infectious clone of TMV. Despite insertion of the foreign peptide sequence into the viral coat protein, stable virions are provided by this invention so that systemic infections is readily achieved in suitable plants. In some instances, the method utilizes coinfection of the plant with 1) the infectious clone having a modified CP gene, but a wild type movement protein (MP) gene and 2) a second TMV infectious clone having a wild type coat protein gene and a MP gene that has been modified to render the movement protein dysfunctional.

In one embodiment of the invention the CP modified infectious clone is mutagenized to insert nucleic acid sequence encoding a 10 to 20 amino acid viral antigenic epitope between the codons encoding amino acids 154 and 155 of the wild type TMV CP. The inserted peptide sequence is advantageously selected from such viral epitopes as HIV gp120 loop III, and human influenza virus hemagglutinin epitopes.

BRIEF DESCRIPTION OF THE DRAWINGS

FIGS. 1A and 1B show that anti-TMV antibodies were raised by administration of either the TMV and the TMV-ZP3 hybrid. FIGS. 1C and 1D show that inoculation with the TMV virus did not raise anti-ZP3 titer, but inoculation with the TMV-ZP3 CP modified virions raised a high titer of anti-ZP3 that gradually declined after inoculation ceased on day 27.

FIG. 4A is a photograph of Western blot analysis of proteins extracted from plant lines transformed with PRO1-derived constructs extracted from R1 plant lines immunostained with anti-TMV CP antisera. Molecular weight markers in kD are indicated at the right and left.

FIG. 4B is a photograph of Western blot analysis of proteins extracted from plant lines transformed with PRO1-derived constructs extracted from R1 plant lines immunostained with anti-TEV-NIa antisera. Molecular weight markers in kD are indicated at the right and left.

FIG. 6A shows the percentage of plants from untransformed tobacco (x) and lines PRO1.TN-1,4 (squares), PRO4.NT-C,2 (triangles) and PRO4.TN-1,10 (circles), showing systemic symptoms on successive days post inoculation with TEV. Eight plants per line were inoculated with a 1:1000 dilution of sap from TEV-infected tobacco.

FIG. 6B is a photograph of a Western blot analysis of protein extracts from systemic leaves of the plants shown in FIG. 4A at 5, 7, 10 and 14 days post inoculation (dpi). Proteins were immunostained with an anti-TEV CP antibody. On the left are indicated the different tobacco plant lines analyzed.

FIGS. 8A–8C show photographs of Western blot analyses of transgenic transcript and proteins upon TEV infection. Untransformed tobacco and plant lines PRO1.TN-1,4, PRO4.NT-C,2, and PRO4.TN-1,10 were either mock (−) or TEV inoculated (+). Migrations of TEV NIa:TMV CP fusion protein and TMV CP are indicated on the right.

FIG. 8A shows protein extracts immunostained with an anti-TEV CP antibody.

FIG. 8B shows protein extracts immunostained with an anti-TMV CP antiserum. Northern blot analysis of total RNAs hybridized to a TMV CP-specific DNA probe.

FIG. 8C shows Northern blot analysis of total RNAs hybridized to a TMV CP-specific DNA probe.

FIG. 9A shows a Coomassie blue stained gel of SDS-PAGE (12%) separation of TMV coat protein, leaf proteins and proteins from leaves of tobacco plants infected with recombinant TMV-ZP3$_{331-343}$.

FIG. 9B shows an immunoblot of an identical gel labeled with rat monoclonal antibody specific for ZP3$_{336-342}$. Column M contains protein molecular weight markers; Lanes 1 and 6, purified wild type TMV coat protein; Lanes 2 and 7, extract from uninfected tobacco leaf; Lanes 3 and 8, extract from tobacco leaf infected with TMV-ZP3$_{331-343}$; Lanes 4 and 9, protein purified from the primary pellet fraction of leaves infected with TMV-ZP3$_{331-343}$; Lanes 5 and 10, protein purified from the primary supernatant fraction of leaves infected with TMV-ZP3$_{331-343}$.

FIG. 10A shows the serum titer to TMV of C57BL/6J mice from experiment 1.

FIG. 10B shows the serum titer to KLH-ZP3 of C57BL/6J mice from experiment 1.

FIG. 10C shows the serum titer to TMV of BALB/cBy mice from experiment 2.

FIG. 10D shows the serum titer to KLH-ZP3 of BALB/cBy mice from experiment 2.

FIG. 10E shows the serum titer to TMV of BALB/cBy mice from experiment 3.

FIG. 12A is a micrograph of material isolated from the primary pellet.

FIG. 12B is a micrograph of the primary supernatant fraction. Both fractions were deposited onto grids, negatively stained, and viewed at 60,000 magnification.

FIG. 13 shows four photomicrographs of ovarian follicles of BALB/cBy mice (Example 12, experiment 3).

FIG. 14A shows leaves that contain the 35S-uidA gene construct.

FIG. 14B shows leaves that contain the cAB-uidA gene construct.

FIG. 14C shows leaves that contain the pal2-uidA gene construct.

FIGS. 16A–16G are a series of photographs illustrating functional complementation of viruses lacking the MP gene by transgenic tobacco plants that express the MP gene.

FIG. 16A shows GUS activity in leaves of line cAB-NN F 3 days after inoculation with RNA transcripts of TMVΔMP-GUS.

FIG. 16B shows GUS activity in leaves of line 2005 3 days after inoculation with RNA transcripts of TMVΔMP-GUS.

FIG. 16C shows GUS activity in leaves of line PMN 3 days after inoculation with RNA transcripts of TMVΔMP-GUS.

FIG. 16D shows morphology of local lesions in line cAB-NN F plants 3 days after inoculation with transcripts of TMVΔMP at higher magnification.

FIG. 16E shows morphology of local lesions in line 2005 plants 3 days after inoculation with transcripts of TMVΔMP at higher magnification.

FIG. 16F shows cAB-NN J leaf inoculated with TMVΔMP virions (right side of leaf) at a concentration that would produce approximately 75 lesions on a plant line 2005 leaf, and with TMV virions (left side of the leaf) at a concentration that would produce about one quarter as many lesions.

FIG. 16G shows cAB-NN O line inoculated with TMVΔMP virions (right side of leaf) and TMV virions (left side of leaf) using the same inocula as in FIG. 16F.

FIG. 17A shows the relative concentration of inoculum necessary to produce local lesions on TMVΔMP inoculated plants.

FIG. 17B shows the relative concentration of inoculum necessary to produce local lesions on wt TMV inoculated plants. The values are the averages of 2 leaves on each of 3 plants, 3 days after inoculation with 50 μl per leaf of a standard virion inoculum solution (TMVΔMP or TMV) that would produce approximately 300 local lesions on a plant line 2005 leaf (defined as a relative concentration of 1), and with dilutions of this solution. Lines of best fit were determined by linear regression.

DETAILED DESCRIPTION OF THE INVENTION

Figure 1A:
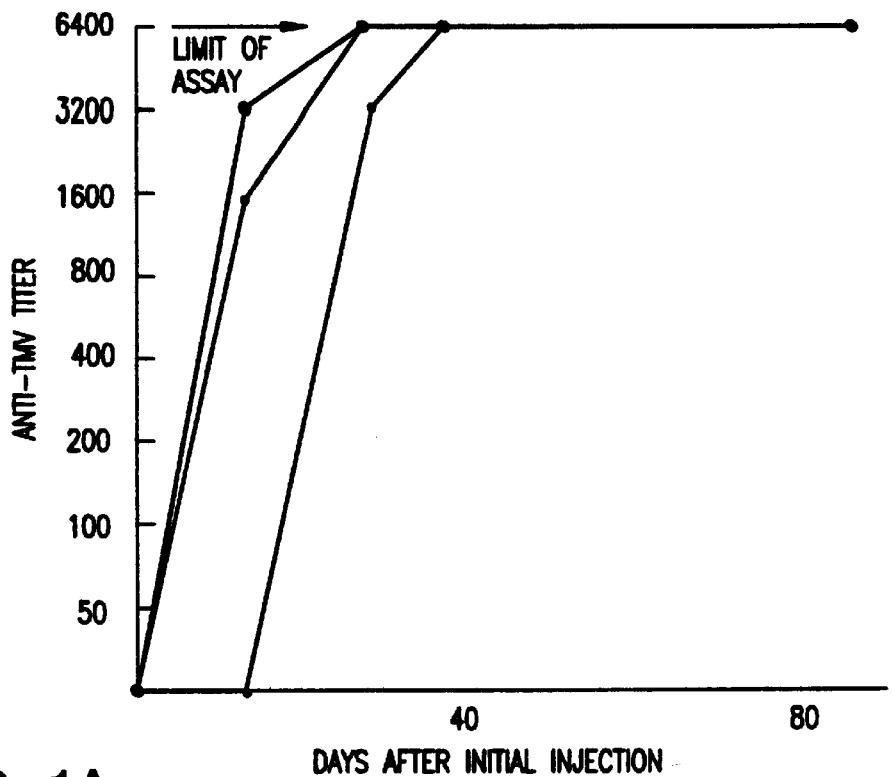
FIGS. 1A–1D show graphs of serum titers raised in mice by administration of TMV or TMV-ZP3 CP modified virions.
Figure 1B:
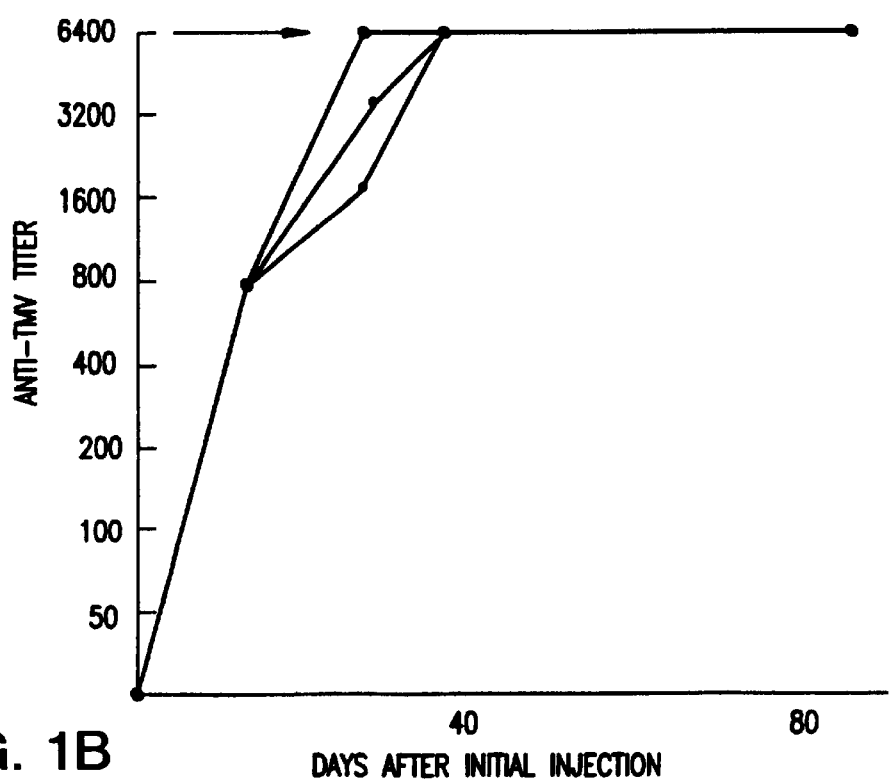
Figure 1C:
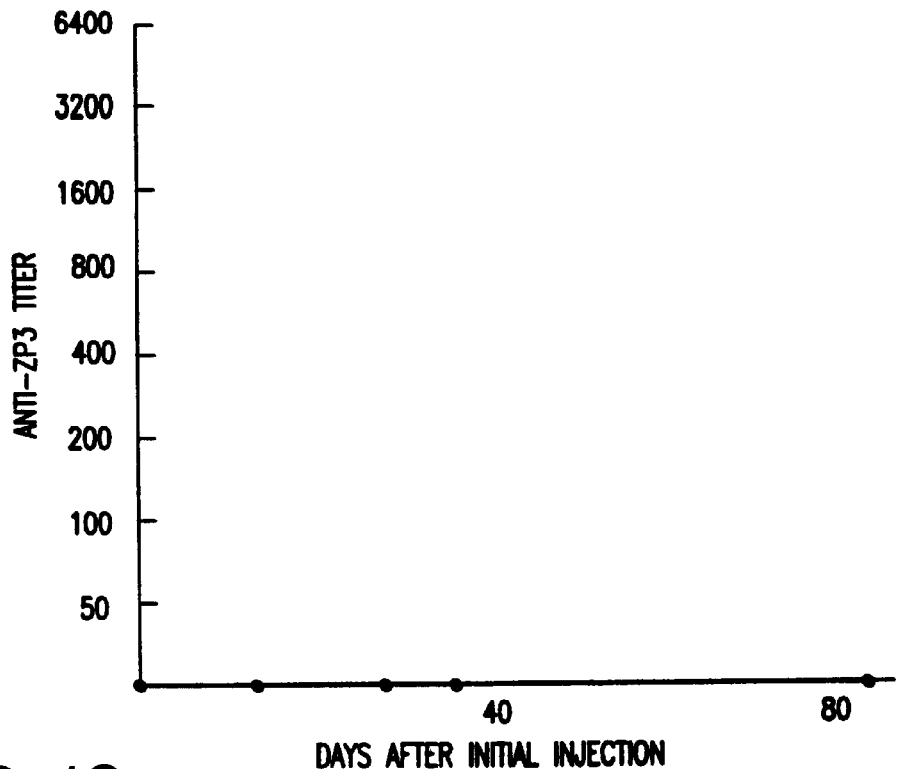
Figure 1D:
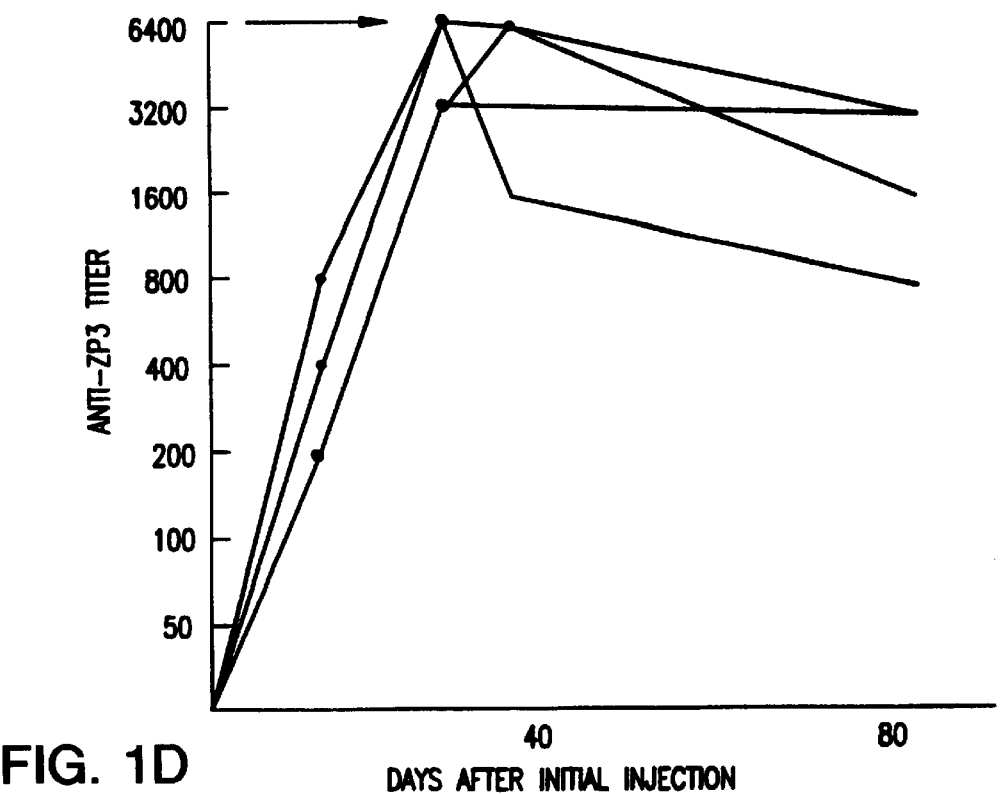

The present invention provides a recombinant TMV coat protein-based protein precursor containing the amino acid sequence for a heterologous protein, preferably of between 5 and 20 amino acids. The CP-based precursor protein can be engineered to contain one or more amino acids immediately adjacent to the heterologous protein that are readily treated chemically or enzymatically to release the heterologous protein from the precursor protein. For instance, an inserted codon for methionine immediately upstream of the nucleotide sequence encoding the heterologous protein is readily hydrolyzed with cyanogen bromide, and an inserted codon for arginine will release the heterologous peptide by trypsin digestion. Since the TMV CP (SEQ. ID. NO. 1) contains no methionines, it is preferred that the recombinant TMV CP be treated with cyanogen bromide to release the heterologous protein.

Further, the present invention provides two types of modified TMV viral vectors derived from the "infectious clone" of the virus: a primary viral vector and a "helper" viral vector. Both types of vector are derived from the well known "infectious clone" of the TMV virus, which comprises the promoter of the T7 polymerase gene ligated to the full length cDNA clone of the U1 (common, (ATCC #PV-135)) strain of TMV and encodes both the CP and MP proteins (Holt and Beachy, supra). The nucleotide sequence of TMV is provided herein as SEQ. ID NO. 2. Transcription by T7 polymerase of the cloned cDNA encompassing the full genome, operably linked to the promoter of the T7 polymerase gene, produces a full length transcript. This transcript, when inoculated into suitable plant species, such as tobacco plants, spinach plants, and others causes infection and is therefore referred to herein as an "infectious clone" of the virus.

To produce the CP-based protein precursor of this invention, the TMV wild type CP gene in the above described infectious clone is replaced by a gene similar to the CP gene but modified to encode a CP fusion protein with heterologous amino acids inserted near, but not at, the carboxyl terminus (amino acid 158). Preferably the heterologous amino acids are inserted between amino acids 154 and 155 of the wild type TMV coat protein. The modified infectious cDNA clone so produced encodes a wild type MP and a CP modified as described above when transcribed by T polymerase. One skilled in the art will appreciate that the modified infectious clone can also be further modified to replace the T polymerase promoter by any other strong promoter for transcription of the cDNA clone in vitro by contact with a polymerase therefore. Such modified clones are also contemplated within the scope of this invention.

Placement of the heterologous protein within the TMV CP-based precursor in the primary vector is key to the practice of this invention. It has been discovered that a TMV CP having a heterologous protein sequence attached to the carboxy terminus will assemble to form virions in vitro or in planta. However, plants infected with the viral vector producing this C-terminal modified CP experience only a lethal necrotic (local) reaction. Hence, viruses with C-terminal modified coat proteins did not spread in the plant beyond the inoculated leaf. In addition, in some cases the modifications to the CP interfere with assembly of the recombinant virions in inoculated plants.

Computer modelling of the TMV virion based upon X-ray diffraction studies was used to predict the amino acid sequences that would be most likely not to interfere with proper folding and assembly of the coat protein. These studies showed that the last four amino acids of the wild-type CP are not fixed, but project from the capsid when the virion assembles. It has been discovered that when the amino acids encoding the heterogeneous peptide sequence are inserted immediately following the last fixed (non-projecting) amino acid of the wild type CP (amino acid 154), and plants are infected with the modified infectious clone cDNA transcript, for some, but not all of the modified CPs, the viral capsids form and the heterologous amino acid sequence projects from the capsid surface, as well as amino acids 155–158 of the CP. Infection of plants with the virion so formed can be accomplished using the method of this invention without rapid plant death. For those modified CPs so altered that will not assemble into virus particles, a helper virus is used to provide wild type CP, which co-assembles with the modified CPs, thus enabling isolation of infectious virus particles that display, on their surface, the target amino acid sequences that are recognized by antibodies specific thereto.

When such plants are coinfected with the primary virus and the helper virus of this invention described below, successful systemic infection can be accomplished. Therefore, it is preferred that in the primary vector, the DNA encoding the heterologous peptide be inserted into the CP gene between the codons for amino acids 154 and 155. Any method of site-directed mutagenesis known in the art (see Sambrook, et al., *Molecular Cloning A Laboratory Manual*, Second Edition, Cold Spring Harbor Laboratory Press, 1989) can be used to insert the DNA encoding the heterologous peptide.

Any antigenic epitope of from about 5 to 20 amino acids can be used for which antibodies are known or are discovered that neutralize a virus or other pathogen, as shown by routine tests well known in the art. For instance, as shown in Table 1, antigenic epitopes from gp 120 loop III of the HIV virus, the Hemagg. 12CA5 of the influenza virus, c-myc 9E10 of the human c-myc oncogene, and zp3 of the murine zona pellucida have all been successfully incorporated into the modified CP of TMV.

In addition to the CP-modified infectious clone, the present invention provides a second type of modified infectious clone, the helper virus, also known herein as the "MP-modified infectious clone." The MP-modified infectious clone functions as a TMV helper virus and complements the CP-modified infectious clone by producing in infected plants sufficient wild type CP to assist in stable assembly of the viral capsid. Systemic spread of the virions cannot be accomplished without formation of stable virions, and it has been discovered that in some cases systemic spread of the virions containing modified CP could not be accomplished with virus produced from the CP-modified infections clone alone, even though stable capsid formed. Hence, the MP-modified infectious clone of this invention helps to accomplish systemic plant infections so that the potential for large scale production of vaccines and other peptides can be realized.

The "MP-modified infectious clone" is derived similarly to the CP-modified infectious clone, except that it contains a wild type CP gene and a MP gene that has been genetically modified to inactivate the MP. In one embodiment of the invention, the wild type MP (SEQ. ID. NO. 25) of the infectious clone is modified to produce a completely dysfunctional MP, but without decreasing production of the wild type CP from the modified transcript. There are many ways to inactivate the MP, for instance deletions, frame shifts, etc. A frameshift mutation introduced into the movement protein gene as described in Example 7 creates a deletion mutant (SEQ. ID NO. 3) of the MP with amino acids 229–231 of the wild type MP deleted. This deletion creates a termination codon and leads to the production of a truncated MP composed of 62 amino acids, compared with the wild type 30 kDa MP of 267 amino acids. The MP produced from the MP-modified infectious clone is non functional and cannot spread from one plant cell to another. Surprisingly, however, the MP-modified infectious clone assists in systemic spread of the virion produced from the CP-modified infectious clone.

In another embodiment, the MP-modified infectious clone, known as TAD26, contains DNA encoding a fragment of the TMV MP gene comprising the wild type nucleotide sequence 6559–5703, but with a deletion of nine nucleotides (6677–6695) (SEQ. ID NO. 4). When TAD26 is engineered into the TMV infectious clone cDNA in the place of the wild type MP gene, upon replication and expression, the MP-modified infectious clone so formed produces an inactivated MP and has the additional characteristic that production of the wild type CP is reduced as well. Thus TAD26 constituitively down regulates production of the wild type CP.

It has been discovered that dual infection of a suitable host plant with both the primary virus containing the modified CP and the helper virus containing the inactivated or modified MP leads to systemic plant infections, and hence to production of large quantities of the heterologous peptides. The wild type coat protein produced from the helper virus is incorporated into the viral capsid along with the modified CP, thereby assuring formation of a stable capsid that incorporates a substantial proportion of the modified CP containing the heterologous amino acids. Thus, even though the helper virus contains no functional MP, the MP produced by the primary virus enables movement of sufficient wild type CP along with the modified CP to supplement formation of the capsids without overwhelming the capsids with wild type CP.

The ratio of CP-modified infectious clone to MP-modified infectious clone used for co-infection of plants is determined empirically for any particular combination of host plant and heterologous peptide sequence, and MP-modified infectious clone. The goal is to adjust the ratio to produce sufficient wild type CP to facilitate viral movement through plant cell walls, but not enough that wild type viral particles are formed. For instance, since TAD 26 produces a decreased amount of wild type coat protein, the proportion of MP-modified infectious clone can be increased when TAD26 is used as the MP-modified infectious clone in the co-infection process over what is used when the MP-modified infectious clone does not constituitively down regulate production of wild type CP in the helper virus. Generally, however, the ratio of CP-modified infectious clone to MP-modified infectious clone is in the range from about 1:1 to 10:1.

As used herein a suitable plant host is any variety of plant known to be subject to infection by tobacco mosaic virus or by the plant virus whose MP is engineered into the primary viral vector. For instance suitable host plants for TMV include lettuce, spinach, tomato, potato as well as *Nicotiana tabacum, N. glutinosa, N. sylvester, Phaseolus vulgaris* and *Chenopodium amaranticolor.*

Since the modified CP is produced under the control of the virus promoter rather than under the control of the plant promoter, up to 40 percent of the total protein in the plant is the modified CP containing the TMV coat protein-based protein precursor of this invention.

Therefore, in one embodiment, co-infection using viral transcripts of the CP-modified infectious clone and of the MP-modified infectious clone is used to accomplish systemic infections of suitable host plants. After construction of the modified clones, the DNA constructs are transcribed in vitro by suitable reactions carried out in the presence of a polymerase active with the promoter (i.e., T7 polymerase with the T7 promoter) to generate RNA for sequential inoculation of plants. Alternatively, simultaneous co-infection can be accomplished using the recombinant viruses in the appropriate ratio.

In another embodiment, the MP-modified helper virus is not used. Instead the wild type CP necessary to accomplish systemic infection of the CP-modified infectious clone or virions produced from it is provided by using a transgenic host plant that synthesizes an RNA molecule encoding wild type CP. In another embodiment the transgenic host plant produces an RNA molecule which, upon infection by the virus, is replicated, leading to production of messenger RNA that is translated to produce virus CP. The transgenic coat protein catalyzes assembly of the mutant proteins into virus particles, and facilitate transport of the infection from leaf to leaf in the infected plant. For instance, a CP transgenic tobacco plant line, such as plant line 3646 (see Powell-Abel, et al., *Science,* 232:738–743, 1986), which contains a transgenic wild type TMV CP gene, upon infection with the CP-modified infectious clone, undergoes systemic infection of the recombinant virus.

In one preferred embodiment of the invention, tobacco plants, preferably var. Xanthi nn are co-infected with recombinant TMV virus produced from the CP-modified infectious clone encoding a heterologous antigenic epitope of from about 5 to 20 amino acids located between amino acids 154 and 155 of the TMV coat protein. The TMV is used as a carrier protein for small antigens, preferably viral antigens, useful for inducing production of protective antibodies to neutralize the antigen when a subject is immunized by exposure to the viral particles carrying the exposed antigenic sequences. In one embodiment of the invention the ZP3 protein (SEQ. ID NO. 16) is used as the antigen for the purpose of inducing a contraception inducing immune response that prevents conception in mammals.

The method of exposure can be by inoculation of the subject with purified antigen at appropriately spaced intervals using methods routine in the art or by the subject ingesting plants that have been infected with the virions produced from the CP-modified clones of this invention into which a nucleotide sequence encoding a heterologous viral or other antigen has been encoded. The purified virus or a plant in which the recombinant virus is accumulated is administered in an immune response stimulating dose as determined by those skilled in the art taking into account, for instance, the body weight and general health of the subject.

Modified TMV virions produced from such transcripts have the heterologous viral or other antigen projecting from the surface of the viral coat, and are capable of stimulating producing of antibodies in the subject that neutralize the antigen. Alternatively, immunogenic exposure can be by a combination of inoculation and ingestion of the antigenic epitopes, or by ingestion alone as described in Examples 8, 9 and 12. The virus can be ingested directly by intubation or oral inoculation of a subject can be accomplished by the subject consuming a sufficient quantity of a plant, such as spinach, that has been systemically infected with a CP-modified infectious clone to raise a neutralizing level of antibodies to the heterologous antigenic epitope encoded by the CP-modified infectious clone.

Virus can also be grown and maintained in protoplasts of such plant lines as *N. tabacum* L. cv BY-2. Generally in vitro transcripts are inoculated into tobacco protoplasts by electroporation as described by Watanabe, et al. (*FEBS Lett.,* 219:65–69, 1987). In addition, virus can be grown in cultures of infected cells. Such cells can be maintained for extended period of time (Murakishi et al., *Virology* 43:62–68, 1971).

In an alternative embodiment, the method of co-infection with CP-modified clones and MP-modified clones can be adapted to express the mutant CPs in a wide variety of different hosts in which TMV is not an infectious virus. This embodiment of the invention takes advantage of the fact that host tropism/specificity is often reflected in the ability of the movement protein of a particular virus to function in one host or another. For example odontoglossum ringspot virus (ORSV) spreads systemically in orchids, but not in tobacco plants. Replacing the MP of TMV with that of ORSV enables TMV to move systemically in orchids. In the present invention, therefore, systemic infection of the CP-modified infectious clone of TMV in a plant host system other than tobacco can be accomplished by mutagenizing the CP-modified infectious clone to replace the wild type TMV CP gene with the wild type MP gene of a plant virus that is infectious in the plant in which infection is desired. For systemic co-infection this CP-modified infectious clone would be used with a helper virus engineered to produce the wild type TMV CP and an inactive form of the MP of the same host plant virus. Alternatively, the single infection method can also be modified and employed in a transgenic plant line engineered to produce the TMV CP upon inoculation with the CP-modified infectious clone.

In yet another embodiment of this invention, the CP gene of the TMV cDNA infectious clone is removed to make room for insertion of a nucleotide sequence (SEQ. ID NO. 5) encoding TEV-NIa based expression cassette PRO1, described in full in U.S. patent application Ser. No. 08/192, 152, filed on Feb. 3, 1994, which is incorporated herein by reference. The TEV-NIa based expression cassette (SEQ. ID NO. 6) contains two cassette sites into which heterologous DNA can be inserted recombinantly for expression of protein sequences. The NIa based vector allows transcription and translation under the control of a single transcriptional promoter, of a polypeptide comprising the protease flanked on each side by its heptapeptide cleavage sites. Upon translation, the protease releases the two heterogeneous proteins in equimolar amounts by autoproteolytic reaction. Nucleotide sequences encoding heterologous peptides ligated into the insertion sites of the NIa-based cassette contained within the modified infectious clone can replicate in isolated protoplasts held in culture, and tissue cultures derived therefrom, or can be inoculated into host plants for expression therein. In the present invention, it is contemplated that one or two TMV modified CP genes are inserted into the cassette sites of the NIa based vector, which is in turn inserted into the TMV cDNA infectious clone in the place of the CP gene. Alternatively, genes encoding a wild type CP and one or more modified CP can be linked in the cassette, or genes encoding one or more MP and one or more CP can be placed into the cassette sites.

Therefore, in this embodiment of the invention the coat proteins of plant viruses belonging to a different taxonomic group than TMV, or other genes capable of protecting a plant against insect or disease, can be ligated into the cassette sites of the NIa-based vector in the infectious clone for production in the host plant. If recombinant plants transfected with a gene encoding the wild type movement protein of the TMV are inoculated with the modified infectious clone, the viral infection will spread systemically. This modified infectious clone vector takes advantage of the extremely high level of expression characteristic of the viral system, and can be used to economically produce large amounts of polypeptides, virions suitable for use as vaccines, etc. The vector of this invention can also be used to simultaneously provide systemic resistance to insect and virus. This modified infectious clone vector takes advantage of the extremely high level of expression characteristic of the viral system, and can be used to economically produce large amounts of polypeptides, virions suitable for use as vaccines, etc.

One skilled in the art will appreciate that such product polypeptides and/or virions can be purified from plant leaves using standard methods (Bruening, et al., *Virology,* 71:498–517, 1976). Generally virus is purified from infected leaf tissues by homogenizing the infected leaf tissues in appropriate buffer, removing the leaf debris, and concentrating the virus either by a salting out procedure, or by ultracentrifugation. The standard methods for purification of TMV can lead to the isolation of 1 to 5 mg of purified virus per gram fresh weight of tobacco leaves.

The following examples illustrate the manner in which the invention can be practiced. It is understood, however, that the examples are for the purpose of illustration and the invention is not to be regarded as limited to any of the specific materials or conditions therein.

EXAMPLE 1 cDNA SYNTHESIS

The cDNA sequence and nucleotide numbering for TMV-U1 were derived from Goelet, et al., supra., cDNA cloning of U1-TMV was as described in Meshi, et al., 1986 with the following modifications. The genomic RNA was annealed with an excess of the oligonucleotide primer pdGGTAC-CTGGGCCCCTACCGGGGTAACGGG (SEQ. ID NO. 7), which is complementary to the 3' end of the RNA and contains a unique 3'-flanking KpnI restriction site. First-strand synthesis utilized AMV reverse transcriptase (Seikagaku) in a buffer described by Ahlquist (1986). After the viral RNA was degraded under alkaline conditions, first-strand cDNA was fractionated by electrophoresis through 2.5% polyacrylamide/8.3 M urea gels. Full length cDNA was recovered and annealed with the oligonucleotide pdGCTGCAGTATTTTTACAACAATTACC (SEQ. ID NO. 8), which corresponds to nucleotides 1–20 of the genomic RNA plus a unique 5'-flanking PstI restriction site. Second-strand synthesis utilized Klenow polymerase (Promega, Madison, Wis.) followed by AMV reverse transcriptase. PstI linkers (New England Biolabs, Beverly, Mass.) were added to the double-stranded (ds) cDNA by ligation and digested with PstI, and the cDNA was size fractionated on a Bio-Gel A-150m (Bio-Rad, Hercules, Calif.) column. The full length cDNA thus obtained was restricted with BamHI at a unique site at nucleotide 3332 of the viral genome, and the fragments so created were ligated into plasmid pSP73 (Krieg and Melton, 1987) that had been digested with PstI/BamHI. Recombinant plasmids were transformed into competent *Escherichia coli* strain DH5α cells (Bethesda Research Laboratories, Grand Island, N.Y.). The resulting transformants were screened for the presence of half-genome cDNA inserts by restriction analysis and nucleotide sequencing.

EXAMPLE 2

CONSTRUCTION OF INFECTIOUS CLONES

A 270-base pair PstI-EcoRI restriction fragment corresponding to nucleotides 1–270 of the modified TMV sequence was subcloned into the vector pBluescript KS+ (Stratagene, San Diego, Calif.). Sequences in the polylinker between the T7 RNA promoter in the vector and TMV nucleotide number 1 were removed by oligonucleotide-directed deletion mutagenesis utilizing the oligonucleotide pdGTAATACGACTCACTATAGTATTTT-TACAACAATTA (SEQ ID NO 9). This placed the T7 promoter region immediately adjacent to the 5' end of the TMV cDNA. The remainder of the TMV genome was reassembled downstream by introducing a SmaI-BamHI (nucleotides 256–3332) restriction fragment, and subsequent a BamHI-KpnI (nucleotides 3333–6396) restriction fragment using standard techniques (Sambrook, supra). Replacements of defective segments of the genome were made by exchanging SmaI-BamHI or BamHI-KpnI restriction fragments with those of alternate cDNA clones.

To produce in vitro transcripts from the cloned TMV genome, a fragment corresponding to the 5' terminus of TMV was isolated, confirmed by nucleotide sequencing, and fused directly to the initiation site of a bacteriophage T7 promoter. Ten micrograms of TMV genomic RNA yielded approximately $2\times10^3$ 5'-half cDNA clones (nucleotides 1–3332 and $5\times10^3$ 3'-half cDNA clones (residues 3333–6395).

EXAMPLE 3

ISOLATION OF VIRION AND COMPONENT RNAs

To 8 ml of cold nucleoprotein solution (3 to 7 mg/ml) in 1 mM sodium EDTA buffer was added 0.4 ml of 100 mg/ml SDS. The tube was transferred immediately to a boiling water bath and the contents were stirred until the solution reached 80° C. The tube was transferred to ice water and stirring was continued until the solution temperature dropped below 40° C. After the tube had remained 5 to 10 minutes more on ice, 0.16 ml of 0.4 M Tris, 0.04 M acetic acid was added, followed by 8 ml of liquid phenol that had been equilibrated with 0.05 M Tris, 0.004 M acetic acid. The phases were mixed by shaking for 2–3 minutes and separated by centrifugation. The aqueous phase was extracted a second and, sometimes, a third time. The RNA was precipitated by adding 0.8 ml of 2 M sodium acetate, 0.2 M acetic acid, and 16 ml of cold 95% ethanol. The insoluble material was recovered by centrifugation. The precipitate was washed once with 95% ethanol and brought nearly to dryness in a stream of dry nitrogen. It was dissolved in water, and the RNA solution was stored at -20° C. RNA concentrations were estimated using an extinction coefficient of 21 $cm_2mg^{-1}$ at 260 mn for sodium ribonucleate in 0.1 or higher ionic strength buffer (Mandeles and Bruening, 1968).

EXAMPLE 4

In vitro TRANSCRIPTION AND INOCULATION

Plasmids containing full-length modified TMV cDNA clones were linearized with KpnI, which restricts the plasmid at the 3' end of the TMV cDNA, blunted by removing the 3' overhang with Klenow polymerase, and used for the production of run-off transcripts. Transcription by T7 RNA polymerase (Promega, Madison, Wis.) used the reaction conditions as described by Nielsen and Shapiro (*Nucleic Acids Res.*, 14:5936, 1986), except that the concentrations of ATP, CTP, and UTP were increased to 1 mM each and BSA was added to a final concentration of 100 µg/ml. After incubation, 20 mM sodium phosphate buffer, pH 7.0, was added and the mixture inoculated directly onto leaves dusted with 330 grit carborundum (Fisher Scientific, Pittsburgh, Pa.). Immediately after inoculation, plants were rinsed with water and placed in growth chambers. Plants were observed daily for signs of infection (necrotic local lesions or systemic vein yellowing and mosaic). Accumulation of infectious virus was monitored by local lesion assay of leaf homogenates made in ice cold inoculation buffer (20 mM potassium phosphate, pH 7.2, 1 mM EDTA). This procedure was followed using modified clones containing the nucleotide sequences for encoding each of the heterologous proteins described in Table 1.

Systemic movement of TMV was monitored by ELISA of non-inoculated tissue to detect virus CP, or by inoculating homogenates of leaf tissues to indicator hosts (e.g., cv. Xanthi NN tobacco). One can also use a modification of a tissue print method developed by Cassab and Varner (1987). Briefly, nitrocellulose paper was soaked in 0.2 m Calcium chloride for 30 minutes and dried on Whatman paper. Thin sections less than or equal to 1 mm of fresh tissue were cut by hand and blotted on the nitrocellulose for 10 sec. and removed from the paper. The prints were blocked with BSA and probed with diluted rabbit anti-TMV primary antibody, followed by alkaline phosphatase-conjugated goat anti-rabbit secondary antibody (Promega). BCIP (5-bromo-4-chloro-3-indolyl phosphate) and NBT (nitro blue tetrazolium) were used as substrate to detect TMV antigen.

Transcripts generated by T7 RNA polymerase from 1 µg of linearized template DNA produced approximately 4–5× $10^3$ necrotic local lesions when inoculated onto Xanthi 'nc' tobacco leaves. Differences were observed between lesions induced by mutant RNA and lesions induced by wild type TMV (Data not shown). Generally the lesions formed by mutants were smaller and had more strongly pigmented (darker brown) centers. When inoculated onto host plant permissive for systemic viral spread (e.g., Xanthi tobacco), the transcripts containing the CP-modified gene produced disease symptoms identical to those caused by wild-type TMV RNA in regard to type, severity of symptoms, and rate of symptom development.

EXAMPLE 5

MUTATION OF CP GENE TO FORM HIV GP120 V3 LOOP FUSION

The CP gene was modified to produce a gene encoding a fusion protein containing the TMV coat protein with an epitope of various proteins inserted near the carboxyl terminus between amino acids 154/155 of the wild type coat protein. The heterogeneous DNA insert encodes an epitope of between ten and twenty amino acids from the proteins of known functions, including those of several viruses as shown in Table 1.

TABLE 1

|  | Epitope | Insertion | Insertion Point |
|---|---|---|---|
| HIV | pg120 loop III | RIHIGPGRAF (SEQ ID NO. 10) YNKRKRIHIGPGRAF (SEQ ID NO. 11) RIHIGPGRAFYTTKN (SEQ ID NO. 12) YNKRKRIHIGPGRAFYTTKN (SEQ ID NO. 13) | 154 |

TABLE 1-continued

| Epitope | | Insertion | Insertion Point |
|---|---|---|---|
| Influenza | Hemagg. 12CA5 | YPYDVPDYA (SEQ ID NO. 14) | 1,154,158 |
| Human c-myc | c-myc 9E10 | EQKLISEEDL (SEQ ID NO 15) | 155 |
| Murine zona pellucida | zp3 | SSSSQFQIHGPRQ (SEQ ID NO. 16) | 154 |

A DNA fragment corresponding to virus nucleotides 5460 to 6396 of the cDNA clone of the CP gene as described above was obtained by digestion with NcoI and KpnI, and cloned into plasmid pBluescript KS (Stratagene, San Diego, Calif.). DNA amplifications by PCR were performed using DNA from the clone as template and two synthetic oligonucleotide primers:

Pair No 1.

5' CATATAGGACCAGGAAGAGCCTTCGGTC-CTGCAACTTGAGG 3' (SEQ. ID NO. 17) and

5' ATTAACCCTCACTAAAG 3' (SEQ. ID NO. 18)

Pair No. 2.

5' GGCTCTTCCTGGTCCTATATGTATTCTA-GAGGTCCAAACCAAAC 3' (SEQ. ID NO. 19) (and SEQ. ID NO. 18)

The polymerase used for amplification was AmpliTaq (Perkin-Elmer-Cetus, Emoryville, Calif.), and the reaction conditions were as recommended by the manufacturer's instructions. The thermal profile of the cycler was: 30 seconds at 95 degrees C., 1 minute at 30 degrees C., one minute at 72 degrees C. Thirty cycles were used, followed by a single 10 minute soak at 72 degrees C.

DNA product from each of the above amplifications was mixed and used as template for a further amplification with the synthetic oligonucleotide primers SEQ. ID NOS. 18 and 20. Reaction conditions and thermal cycling parameters were as described above. DNA product from this second-round amplification was cleaved by digestion with NcoI and KpnI. The fragment containing the modified viral sequence was isolated by size following electropheresis in agarose gels and inserted to replace the equivalent sequence in the in vitro transcription vector. The nucleotide sequence of the modified gene encoding the fusion protein containing the 10 amino acid epitope was confirmed by conventional techniques of DNA sequence analysis. The above technique was modified in keeping with the teachings of the art to obtain modified CPs containing each of the amino acid inserts shown in Table 1.

The amino acid sequences of the modified CPs containing viral epitopes of HIV gp 120 loop III inserted between amino acids 154 and 155 of the wild type CP are provided herein as SEQ ID NOS: 21, 22, 23 and 24. Using well known methods of site-directed mutagenesis, the amino acid sequence of the TMV CP was mutagenized to insert a nucleotide sequence encoding a 10 to 20 amino acid sequence of the desired heterologous protein so as to generate a CP fusion protein having the insert at the desired location as shown in Table 1. In one embodiment the inserted amino acid sequence is homologous to the carboxy terminus of an alternative viral coat protein.

EXAMPLE 6

MUTATION OF MP GENE TO FORM TRUNCATED MOVEMENT PROTEIN

A frameshift mutation was introduced into the movement protein gene as was described in Holt and Beachy, supra. The translation product of the modified MP gene is non functional and viruses with this non-functional movement protein cannot spread from one plant cell to another. The nucleotide sequence encoding the truncated TMV MP is given as SEQ ID. NO. 3.

The procedure used to create the mutation was as follows: A portion of the cDNA clone of the TMV virus bounded by BamHI and KpnI recognition sites and including nucleotides 3333–6396 was subcloned as in Example 3 above. The resulting plasmid was digested with HindIII, which recognizes a site at virus nucleotide 5080. The nucleotides AGCT were added to the 3-prime end of each strand with the Klenow fragment of DNA polymerase I, and the plasmid was then religated with T4 DNA ligase. This procedure created a termination codon and would lead to the production of a truncated MP composed of 62 amino acids, compared with the authentic 30 kDa MP of 267 amino acids.

The fragment released by digestion with BamHI and KpnI containing the modified viral sequence was isolated on SDS PAGE and Western blot and inserted to replace the equivalent sequence in the in vitro transcription vector. The amino acid sequence of the modified MP is shown in (SEQ ID NO: 3).

Inserting a nine amino acid heterologous epitope of Influenza HA between coat protein amino acid residues 154/155 of the TMV CP resulted in systemic infection in the normal systemic host for TMV (Tobacco var. Xanthi$^{nn}$) by the method of this invention. By contrast, when the same insert was attached to residue 158 (the carboxyl terminus of the CP), local necrosis resulted, indicating limited spread of the virus. In addition, the yields of virus particle are much greater from non-necrotic tissue than from necrotic tissue. Spread of the virus was also affected by growing temperature. In plants grown at 32 degrees C. necrotic response was reduced and systemic spread of the virus was observed.

EXAMPLE 7

METHOD OF VIRUS INFECTION AND PURIFICATION

TMV is transmitted to tobacco plants by techniques common to those skilled in the art of plant virology. Briefly, a tobacco plant of appropriate size and age (generally 4–6 weeks after planting the seeds in soil) is dusted with an abrasive, generally carborundum or celite, and a suspension of virus or viral RNA (or transcript derived from the in vitro transcription reaction described above) is added, and spread on the leaf so as to cause a mild wound, thereby introducing the virus or RNA into the wounded leaf cells. The plants are grown under conditions suitable for healthy growth of the plant. Such conditions result in infection in the plant with virus concentrations as low as 0.001 $\mu$g/ml. Increasing the inoculum concentration increases the number of sites of infection and the rate of virus accumulation in the inoculated leaves, as well as the rate of spread to the upper leaves. Replication of the virus, localized spreading of the virus, and systemic spreading of the virus leads to infection of all or most tissues in the plant. Systemic infection was identified in developing leaves by the typical symptom of a dark green and light green mosaic, caused by alterations in the development of chloroplasts in viral-infected cells. Mosaic symptoms generally develop in tobamovirus-infected tobacco plants in nascent leaves that are less than 1.5 cm in length at the time of the initial infection. All subsequently developing leaves display the mosaic symptom. The inoculated leaves and leaves greater than approximately 5–6 cm in length at the time of infection develop no visible symptoms, even though they support high levels of viral replication (J. N. Culver, et al., *Annu. Rev. Phytopathol.*, 29:191–217, 1991).

For co-infection with the helper virus, the helper virus is mixed in effective amounts so as not to overwhelm the infection with large amounts of wild-type coat protein, typically in a ratio of modified CP infectious clone to modified MP infectious clone of from 1:1 to 1:10. Alternatively the RNA transcripts of the modified CP and truncated MP genes can be used in similar ratio to inoculate transgenic plant lines that carry wild-type CP, such as plant line 3646 (see Powell-Abel, et al., *Science* 232:738–743, 1986). These plants are grown in like manner as non-transgenic plants, and are inoculated in the same way.

EXAMPLE 8

ISOLATION OF VIRIONS AND COMPONENT

Using the method of G. Bruening, et al., supra, modified Tobacco mosaic virus virions and component RNA was obtained. The mutant viruses were constructed using oligonucleotide mutagenesis (Kunkel, et al., 1987) of the U1 CP gene. The cloned cDNA encoding the U1 CP was isolated from an infectious cDNA clone of U1 TMV on an Apa I fragment (nucleotides 5455 to 6389) (Nejidat, et al., supra) s fragment was subcloned, mutagenized and inserted back into the original cDNA infectious clone as an Apa I fragment, replacing the wild type sequence. All clones were sequenced by the dideoxy sequencing method to confirm the presence of the desired sequence changes. The mutants were propagated by inoculating *N. tabacum* cv. Xanthi plants with in vitro transcripts of the full length mutant cDNA clones as described by Nejidat, Cellier, et al., 1991. Briefly, seedlings of *N. tabacum* cv Xanthi$^{nn}$ were grown to the 8–10 leaf stage, at which time the plants were inoculated.

Systemically infected tissue was recovered from plants that had been inoculated several weeks earlier with 30 to 200 μg/ml of transcript of the MP-modified infectious clone. The leaves were collected and frozen on dry ice and were powdered by crushing them in a plastic bag. Into a blender containing cold 0.04 M sodium EDTA buffer, pH 7.3 and 1 μl/ml of B-mercaptoethanol were slowly added at 0.02 g per g of leaves of NaHCO$_3$. One to 1.15 ml of buffer was used per g of leaves (Mandeles and Bruening, *Virology*, 71:498–517, 1968).

Homogenization was continued until the temperature of the homogenate rose to about 10° C. Succeeding steps were at 0 to 4° C. Both supernatant fluid and solids were recovered after centrifugation at 3000 rpm for 10 minutes. The solids were homogenized with 0.35 to 0.5 ml per g of original leaf tissue of the EDTA buffer with mercaptoethanol. The supernatant fluid recovered after another 3000 rpm, 10-min. centrifugation was combined with the first supernatant fraction. This fluid was centrifuged at 14,000 rpm for 20 min. The supernatant fluid was filtered through Whatman No. 1 paper. To each 100 ml of filtrate was added 0.75 ml of 200 mg/ml of Triton X-100. The detergent-treated solution was distributed into thick-walled, capless centrifuge tubes containing 17.5 ml per tube. Six milliliters of a solution of 300 mg/ml of sucrose in 1 mM sodium EDTA buffer was layered on the bottom of each tube with a syringe. The tubes were centrifuged in a Spinco 30 rotor for 5.5 to 7 hr at 27,000 rpm at 6° C.

Characterization of the CP Mutants.

CPs of the mutant viruses were analyzed by immunoblot analysis using polyclonal rabbit anti-virus antibodies raised against U1 TMV or SHMV using techniques well known in the art. The secondary antibody was $^{125}$I-labeled goat anti-rabbit IgG (Amersham, Arlington Heights, Ill.). The CPs were fractionated by SDS-PAGE using the method of U. Laemmli (*Nature* 227:680–685, 1970) and electrophoretically transferred to nitrocellulose for analysis (Towbin, et al., *Proc. Natl. Acac. Sci. USA*, 76:4350–4354, 1979).

EXAMPLE 9

TMV was purified from tobacco plants infected with a modified infectious transcript producing virions having exposed on the capsid surface the ZP3 antigenic epitope of Seq. ID NO: 7. In this experiment a helper virus was not used. Yield by this procedure was about 100 micrograms virus per gram fresh weight of leaf. The bulk of the virus was not extracted but remained in the pellet after the first centrifugation. For this reason a different procedure was used for a future preparation.

Purification was accomplished as described in Asselin and Zaitlin, *Virology*, 91:173–181, 1978. Frozen (−70° C.) infected leaves were homogenized with a mortar and pestle using 1.3 ml of 0.5 M Na$_2$HPO$_4$ and 0.5% (w/v) Na-ascorbate per g of fresh tissue. The homogenate was filtered through four layers of cheesecloth. Celite was added to the juice at 5 g/100 ml and the extract was centrifuged at 10,000 g for 30 min. The clarified supernatant fraction was passed through eight layers of cheesecloth, and then PEG 6000 and NaCl were added to the filtrate at final concentrations of 3% (w/v) and 1% (w/v), respectively. The extract was stirred for 10 minutes, left 20 minutes on ice, and centrifuged at 10,000 g for 30 minutes. Pellets were resuspended in one-fourth the original volume with 0.01 M Na$_2$HPO$_4$ and 0.01% (W/V) Na-ascorbate, and treated again with Celite. After a second PEG precipitation and clarification at 10,000 g for 15 minutes, Triton X-100 was added to a final concentration of 2.5 mg/ml. The virus solution was stirred for 10 minutes, left for 20 minutes at room temperature, and centrifuged at 90,000 g for 90 minutes. The virus pellets were resuspended overnight (4° C.) in 1 mM EDTA, pH 7.2. After a clarification spin at 10,000 g for 10 minutes, the virus solution at a concentration of 2.5 mg/ml was made 0.2 M with respect to sodium phosphate buffer, pH 7.0. The modified TMV-ZP3 hybrid was purified following the same protocol through the first PEG/NaCl precipitation.

A group of five mice were injected intraperitoneally and subcutaneously (50 micrograms each) with 100 micrograms of virus protein (total) per mouse, prepared with RIBI adjuvant as per manufacturer's instruction (Ribi Immunochem Research, Hamilton, Mont.). Booster injections at 13 and 27 days after the initial injection contained 50 micrograms (total) per mouse. Blood was sampled from a retro-orbital sinus at days 1, 13, 27, 36, and 84. Serum titers were assessed by capture ELISA on NUNC polysorb plates coated with either TMV coat protein (FIGS. 2A and 2B) or a synthetic ZP3 peptide containing the ZP3 antigen (SEQ. ID NO. 7) conjugated to KLH by a NHS-ester-maleimide heterobifunctional crosslinker via a cysteine residue on the peptide using Eliman's solution according to the manufacturer's instructions (Pierce Chemicals, Rockford, Ill.) (FIGS. 2C and 2D). Detection was using goat anti-(mouse IgG) horse radish peroxidase.

As can be seen by comparing the results in FIGS. 2A and 2C, the virus with unmodified TMV CP induces an antibody against TMV, but not against the ZP3 antigen. By contrast, as can be seen by comparing the results in FIGS. 2B and 2D, the virus having the CP modified to contain the ZP3 antigen raised an antibody titer both to TMV and to ZP3 peptide antigen. The titer of antibodies to ZP3 began to decline somewhat after the administration of TMV-ZP3 was discontinued on day 27.

EXAMPLE 10

Three groups, each containing 5 mice, were utilized in this study. The mice in group A were given an initial injection of 100 micrograms of the unmodified TMV virus with RIBI adjuvant, followed by booster injection of 100 micrograms at 28 and 42 days after the initial injection. The purification procedure followed for the virus used in this experiment differed from the procedure described above. Frozen leaves were ground and filtered as above. However, celite was not added to the homogente. The first centrifugation was also as described, except the pelleting fraction was recovered, further homogenized in a mortar and pestle with about 2 ml of 50 mM Tris, pH 8.0 per gram of starting material. The homogenate was centrifuged again under the same conditions and again the pellet was recovered. The pellet was further homogenized in the above buffer containing 1% Triton X-100 and again centrifuged. This pellet was resuspended in the same buffer containing 0.5% Triton X-100, centrifuged, and twice resuspended in buffer without Triton and recentifuged. The final pellet was resuspended in water and divided into aliquots before freezing at -20° C. Yield exceeded 1 mg virus per gram fresh weight of leaf.

Figure 2:
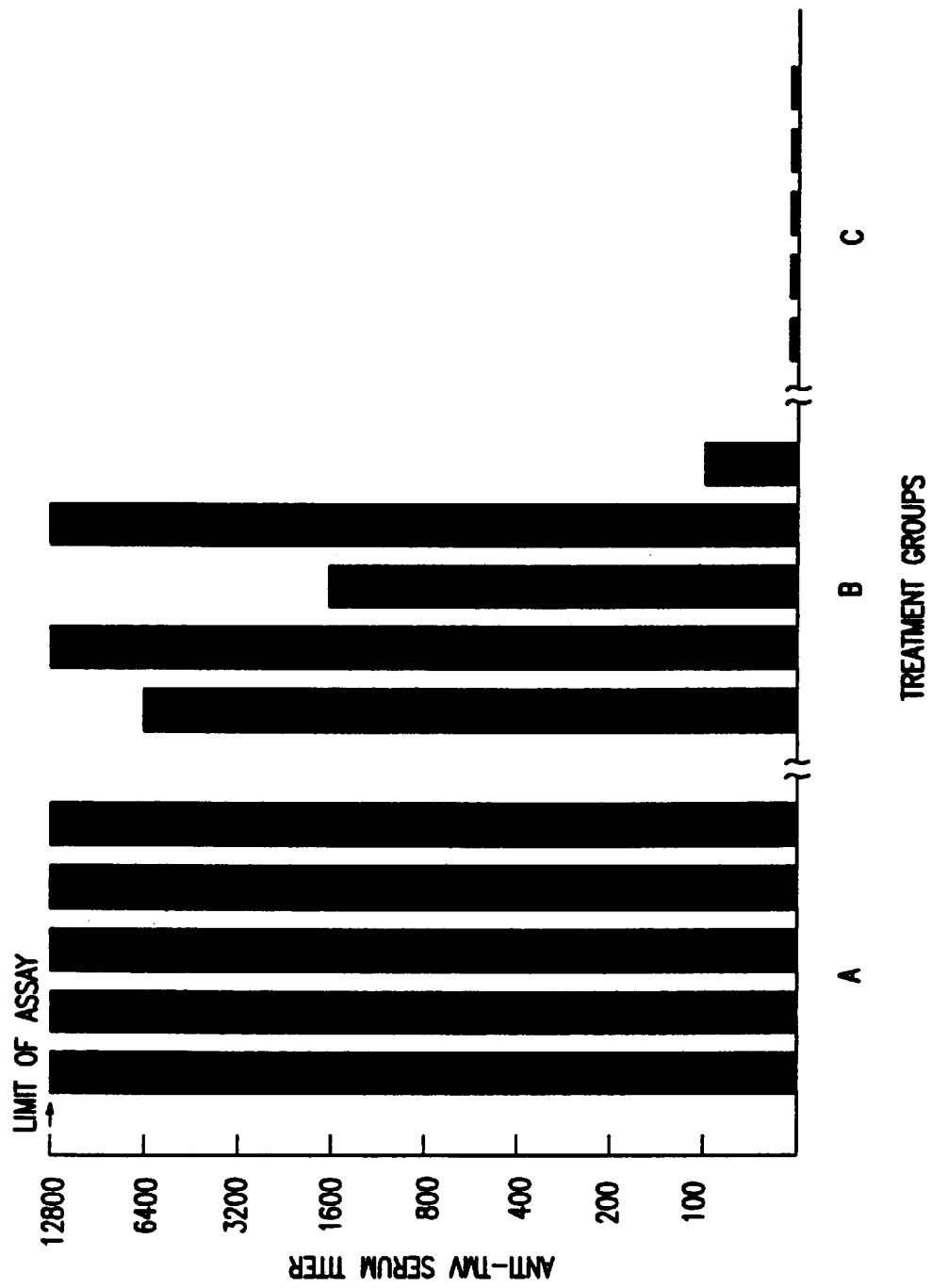
FIG. 2 is a bar graph comparing the levels of anti-ZP3 serum titers developed in mice at 52 days after administration of TMV CP fusion proteins bearing a 15 amino acid fragment of murine zona pellucida 3 (ZP3) as antigen. Group C received the ZP3-modified TMV CP intraperitoneally and subcutaneously. Group B received the ZP3-modified TMV CP intragastricly. Group C did not receive the vaccine. Each bar represents an individual mouse.

Mice in group B received 100 micrograms of the TMV-ZP3 hybrid virus of Example 7 in a 1:1 mixture of phosphate buffered saline and Mylanta® (Johnson & Johnson/Merck, Ft. Washington, Pa.) delivered intragastricly on days 1, 4, 6, 8, 11, 13, 15, 18, 20, 22, 25, 27, 29, 32, 34, 36, 39, 41, 43, 46 48, and 50. Mice in group C were not exposed to the TMV-ZP3 hybrid virus. Blood was sampled and anti-TMV serum IgG titers were assessed as described in Example 7 above. As shown in FIG. 2 (each bar represents an individual mouse), four of five mice in the group receiving the vaccine intragastricly raised IgG anti-TMV serum titer of antibodies of 1600 or above, and all five in the group receiving the vaccine by injection raised titer of antibody to the limit of the assay at 12,800.

EXAMPLE 11

To determine whether the NIa cassette can express and process functional viral genes in vivo, the TMV CP was cloned into PRO1 in either of the two possible locations and the resulting gene constructs were introduced into *Nicotiana tabacum*. Gene constructs were also made in which cleavage by the proteinase was abolished to determine the effects of such modification on protein accumulation and protection. The analysis of transgenic plant lines showed that while the polyproteins were processed in planta, TMV CP accumulated only to a low level, and the level of resistance against TMV was likewise low. Plant lines were also protected against TEV, presumably as a result of NIa expression in accordance with recent studies with other polyviruses (Maiti, et al., *Proc. Nat. Acad. Sci. USA*, 90:6110–6114, 1993; Vardi et al., *Proc. Nat. Acad. Sci. USA*, 90:7513–1517, 1993). Surprisingly, while the initial levels of transgenic protein accumulation were low in all the lines analyzed, in some lines the levels were substantially increased upon infection by TEV, but not by TMV.

A. Description of transgenic plant lines.

Figure 3A:
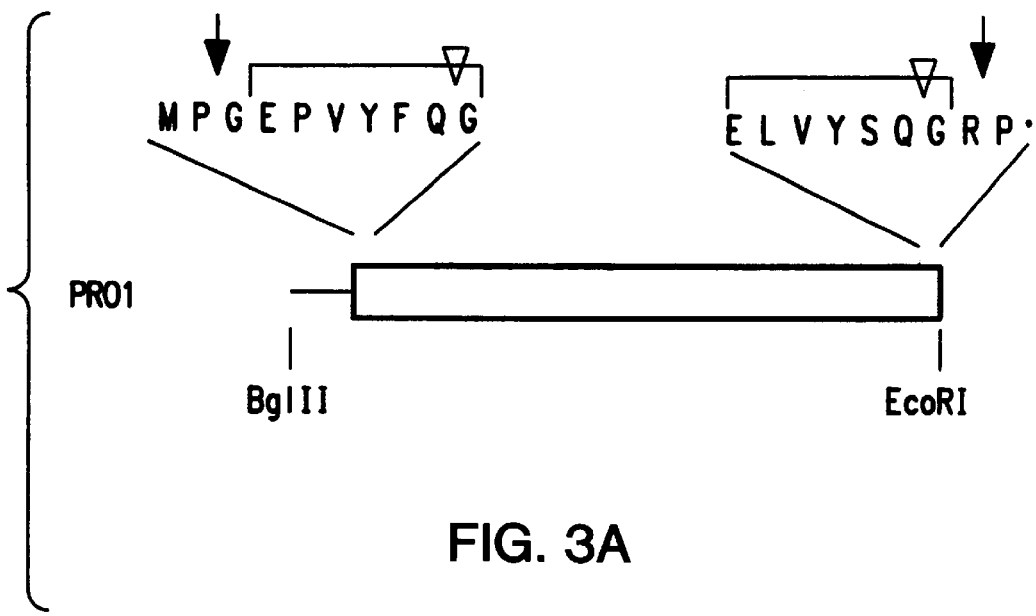
FIG. 3A is a schematic diagram of the NIa-based expression cassette PRO1. TEV NIa protein sequence and TEV 5' untranslated region are shown as an open box and a line, respectively. The single letter amino acid code at the N and C termini include the heptapeptide recognized by the NIa proteinase (indicated by a bracket with an open arrowhead at the cleavage site). The cloning sites for the insertion of foreign proteins (black arrowhead), the methionine start codon, and the stop codon (dot) are also indicated. Position of relevant Bgl II and EcoR I restriction enzyme sites are also indicated.
Figure 3B:
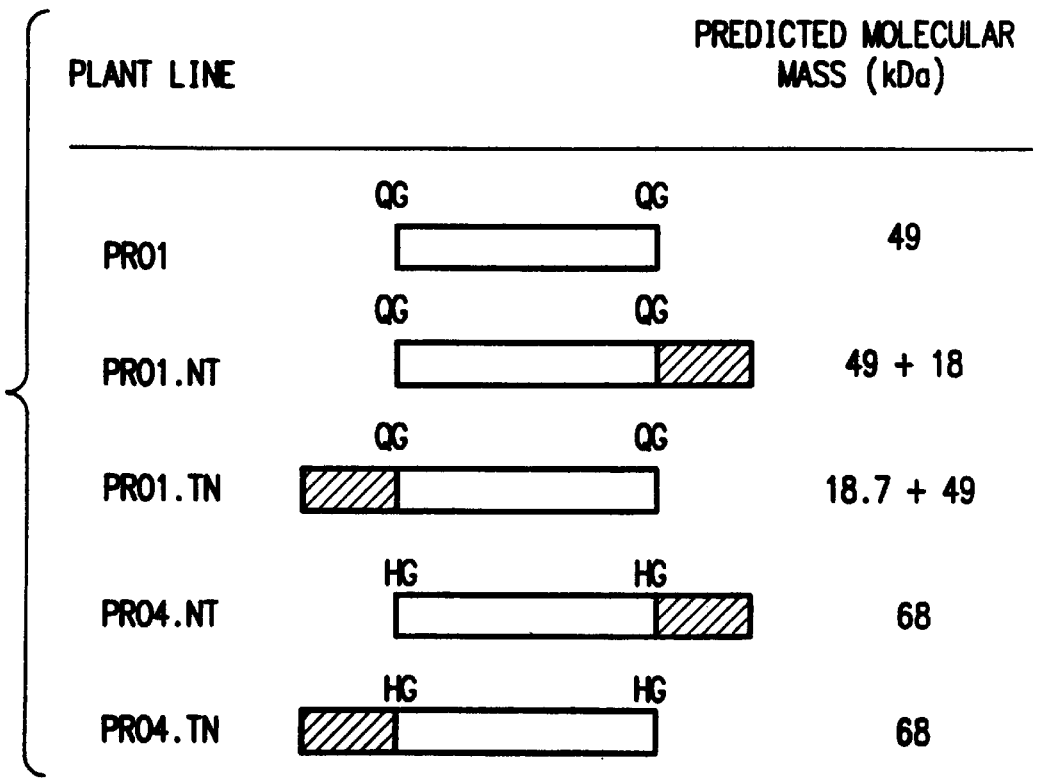
FIG. 3B is a schematic diagram of the PRO1-derived constructs used for plant transformation. The designation for each construct is indicated at the left. Open and striped boxes represent the TEV NIa and TMV CP open reading frames, respectively. At the boundaries between NIa and CP are indicated the sequences for either the wild type (QG, in PRO1 constructs) or the mutated (HG, in PRO4 constructs) recognition sites for the proteinase. The predicted molecular mass resulting from the translation and processing of each construct is also indicated. TMV CP predicted molecular mass is 17.4 kDa.

Xanthi NN plants were transformed with genes containing either of several derivatives of the proteinase cassette containing the sequence encoding the TMV CP (FIG. 3B). Two versions of the cassette were used: PRO1, which contains the natural heptapeptide recognition sequences for the TEV NIa proteinase under the control of the CaMV 35S promoter (FIG. 3A), and PRO4, in which glutamine to histidine mutations were engineered at the cleavage sites to disrupt proteinase processing (Marcos and Beachy, *Plant Mol. Biol.*, 24:495–503, 1994). PRO4 constructs were initially designed to demonstrate that in vivo processing resulted from specific recognition and cleavage by NIa. In both cases the sequence for the TMV CP was inserted either preceding (PRO1.TN and PRO4.TN) or following (PRO1.NT and PRO4.NT) the NIa sequence.

Processing of all constructs in vitro has been previously demonstrated (Marcos and Beachy, supra). A control construct comprising only TEV NIa and target heptapeptides (PRO1) was also introduced into tobacco plants.

B. Plant Material and Plant Transformation.

*Nicotiana tabacum* cv. Xanthi NN plants were used for genetic transformation as well as a non-transformed control. Plant line 748 is a transgenic *N. tabacum* cv. Xanthi NN that expresses the TMV CP under the control of the CaMV 35S promoter (Nelson, et al., *Virology*, 158:126–132. 1987). Plants were grown under greenhouse conditions, and 4–5 weeks old plants were inoculated and held in the greenhouse or transferred to a growth room under artificial light (14 h light/10 h dark) at 25–30° C. The pPRO1-derived gene constructs described by Marcos and Beachy (supra) were digested with Bgl II and EcoR I and inserted in the polylinker region of the intermediate plasmid pMON316, between the CaMV 35S transcriptional promoter and the nopaline synthase 3' untranslated region (Sanders, et al., *Nucl. Acids Res.*, 15:1543–1558, 1987). Leaf disks were transformed through *Agrobacterium tumefaciens*-mediated gene transfer as previously described (Horsch, et al., *Science*, 227:1229–1231, 1985). The resulting plants were screened for gene insertion by polymerase chain reaction, nopaline accumulation (Otten and Schilperoort, *Biochem. Biophys. Acta*, 257:497–500, 1978), accumulation of TMV CP-containing peptides by Western blot analysis, and protection against TMV infection.

C. DNA and RNA analysis.

Young leaf tissue was frozen in liquid nitrogen and stored at -80° C. Total RNA was extracted following a small-scale procedure described previously (Verwoerd, et al., *Nucl. Acids Res.*, 17:2362, 1989). DNA was recovered by ethanol precipitation from the supernatant resulting from the 2M LiCl precipitation of RNA in the extraction procedure.

One microgram of total DNA was analyzed by polymerase chain reaction for the presence of the gene using primers that were specific for either the TMV CP or TEV 5' nontranslated region (5' NTR). For RNA analysis, 20 mg of total RNA were denatured with formaldehyde, subjected to electrophoresis in agarose gels, blotted onto a nitrocellulose membrane (Schleicher & Schuell, New Hampshire, USA), and hybridized to randomly primed 32P-labeled fragments of the TMV-CP cDNA essentially as described (Sambrook, et al., supra).

A total of 15 parental (R0) independent plant lines were produced, including three transformed with PRO1.NT, six with PRO1.TN, two with PRO4.NT, and four with PRO4.TN. R0 lines were selected for further study when scored positive in any one of four assays: detection of nopaline (a nopaline synthase gene was included in the transformation vector), identification of transformed lines by polymerase chain reaction, accumulation of TMV CP-related proteins as shown by Western blot, and/or protection against TMV infection as shown by reduction in the number of necrotic local lesions following inoculation by TMV. R1 seeds were obtained from selected lines and the assays were applied to progeny.

D. Protein analysis.

Leaf tissue was frozen in liquid nitrogen, ground to a fine powder and proteins were extracted in a buffer containing 62.5 mM Tris-HCl, pH 6.8, 6 M urea, 1% (w/v) SDS and 10% (v/v) b-mercaptoethanol. Extracts were boiled, spun to remove debris, and supernatants were loaded onto polyacrylamide gels containing SDS and electrophoresed as described (Laemmli, supra). In all cases, equivalent amounts of cell extract were loaded on the gels. Proteins were blotted onto a nitrocellulose membrane (Schleicher & Schuell, Keene, N.H.) and probed with either a polyclonal antiserum raised against TMV CP, a polyclonal antiserum raised against TEV NIa (kindly provided by J. C. Carrington, Texas A&M University), or a monoclonal antibody raised against the core of potyviral coat proteins (kindly provided by D. D. Shukla, CSIRO, Melbourne, Australia). Antibody binding was detected by immunoreaction to an anti-rabbit IgG coupled to horseradish peroxidase (Pierce, Rockford, Ill.) and subsequent enhanced chemiluminescence (Amersham, Arlington Heights, Ill.).

E. Viruses and Viral Inoculations.

TMV (tobacco mosaic virus, U1 strain) was propagated on *N. tabacum* cv. Xanthi nn, and TEV was propagated on *N. tabacum* cv. Xanthi NN. TMV RNA was extracted from purified virions as described by Bruening et al. (supra). Prior to infection, plants were topped, kept one day in the dark and TMV or TMV RNA was applied in inoculation buffer (20 mM potassium phosphate, pH 7, 1 mM EDTA) and rubbed onto leaves dusted with carborundum. TEV inoculant was prepared by grinding infected plant tissue in inoculation buffer (40 mg/400 μl), and dilutions of the grindate were rubbed to leaves dusted with carborundum.

F. Accumulation of TEV NIa and TMV CP.

Figure 4A:
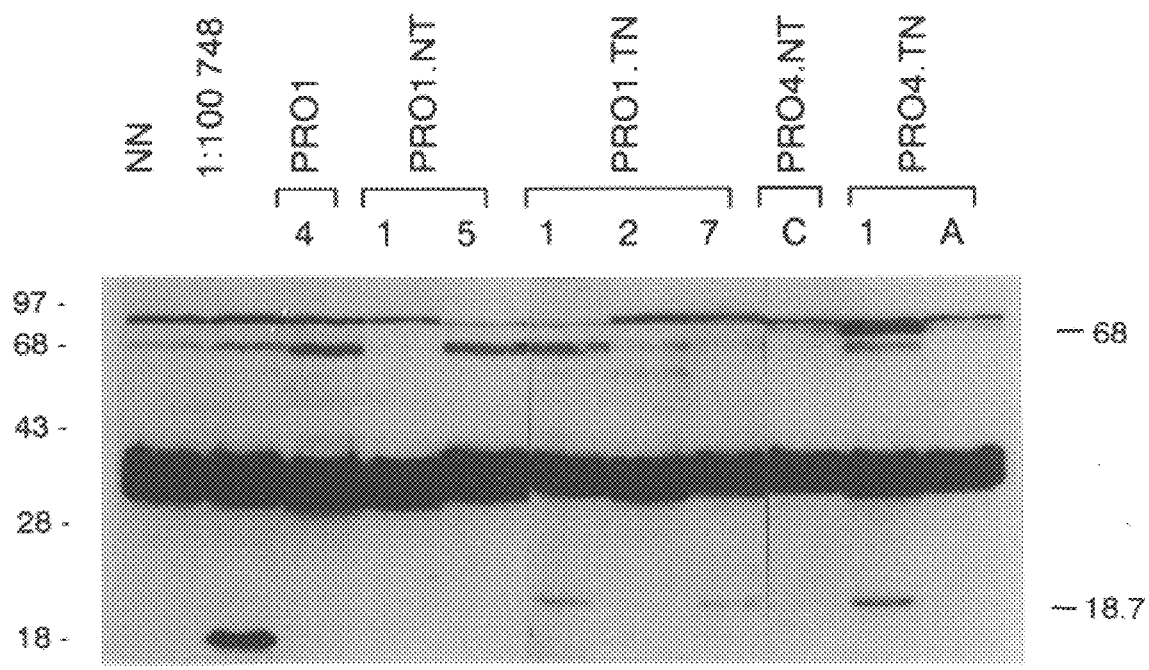
FIGS. 4A–4B show photographs of Western blot analysis of proteins extracted from R1 plant lines transformed with PRO1-derived constructs. The different plant lines analyzed are indicated above each lane, with the prefix (corresponding to the construct) at the top and the suffix below. On the right of each panel are indicated the migrations of the 68 kDa TEV NIa:TMV CP fusion proteins and the 18.7 kDa TMV CP cleaved from the polyprotein. Detectable levels of 18.7 kDa TMV CP were observed in plant line PRO1.TN-2 in the original autoradiograph. The molecular mass (kDa) and positions of pre-stained protein markers are indicated on the left.
Figure 4B:
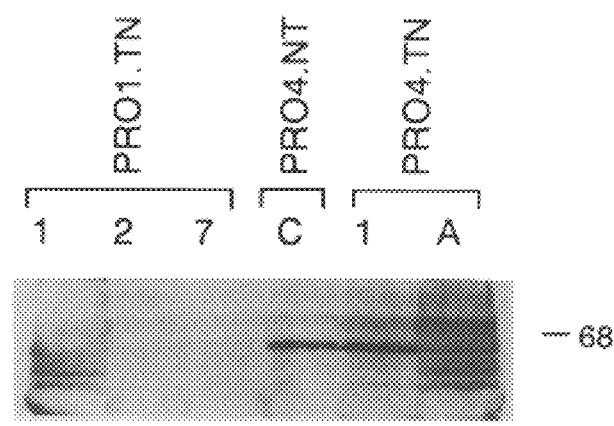

Initial attempts to detect accumulated transgenic proteins by Western blot analysis were unsuccessful. After several experimental modifications to the standard Western blotting procedure, it was found necessary to extract plant tissue with a buffer containing 6 M urea and to overexpose the blots in order to obtain reproducible results. Protein extract from control line 748 was diluted 1:100 with untransformed tobacco extract (NN). Proteins were immunostained with either anti-TMV CP (FIG. 4A) or anti-TEV Nia (FIG. 4B) antisera. FIG. 4 shows the detection of TMV CP-related proteins present in some of the R1 transgenic plant lines that contain the corresponding genes. Several expressors (eight out of ten transformed lines) were identified among lines containing constructs in which the CP was translated preceding the NIa (i.e., PRO1.TN and PRO4.TN; FIG. 3). TMV CP sequences were detected in one plant line (out of 2) in which the CP was translated following the proteinase, e.g. line PRO4.NT-C, resulting in the predicted non-processed polypeptide. No plant lines were recovered that expressed the PRO1.NT gene, although three lines contained the intact gene (data not shown).

TMV CP expressed as part of construct PRO1.TN had a molecular size larger than that of the wild type CP (FIG. 4A) as predicted (FIG. 3B). The difference in size is due to additional amino acid residues that comprise the recognition site for the proteinase. The 49 kDa TEV NIa with anti-TEV NIa antiserum could not be detected due to its reaction with a protein of the same mobility found in transgenic as well as non-transgenic plants (not shown). As shown by the data in FIG. 4, plant lines expressing construct PRO1.TN did not accumulate detectable levels of the 68 kDa fusion protein, indicating that proteolytic processing was highly efficient when the heptapeptide recognition site for the NIa proteinase was present. On the other hand, the uncleaved polyprotein accumulated in those plant lines expressing mutated versions of the cassette; in such cases a 68 kDa band was detected following immunoreaction with either anti-TMV or anti-NIa serum, as shown in FIG. 4. Small amounts of TMV CP were apparently released from the polyprotein in lines that carry constructs PRO4.NT and PRO4.TN (FIG. 4A). The extent of this unspecified cleavage was variable among different protein extracts, and we concluded that it resulted from activities of cellular proteases.

Very low levels of accumulation of transgenic proteins (not above 0.0001%, w/w, of the total protein) were observed in all the plant lines characterized. The accumulation of proteins in plants expressing PRO1-derived constructs was up to three orders of magnitude lower than the CP in plant line 748 (FIG. 4A); this line harbors the TMV CP sequence under control of the 35S cauliflower mosaic virus (CaMV) promoter and is highly resistant to TMV infection (Nelson, et al., supra). Line 748 accumulates a relatively high level of TMV CP (0.01%), while the TMV CP gene, the level of CP in the lines developed in this study is considerably below what is expected from a gene whose expression is driven by the 35S promoter.

Figure 5:
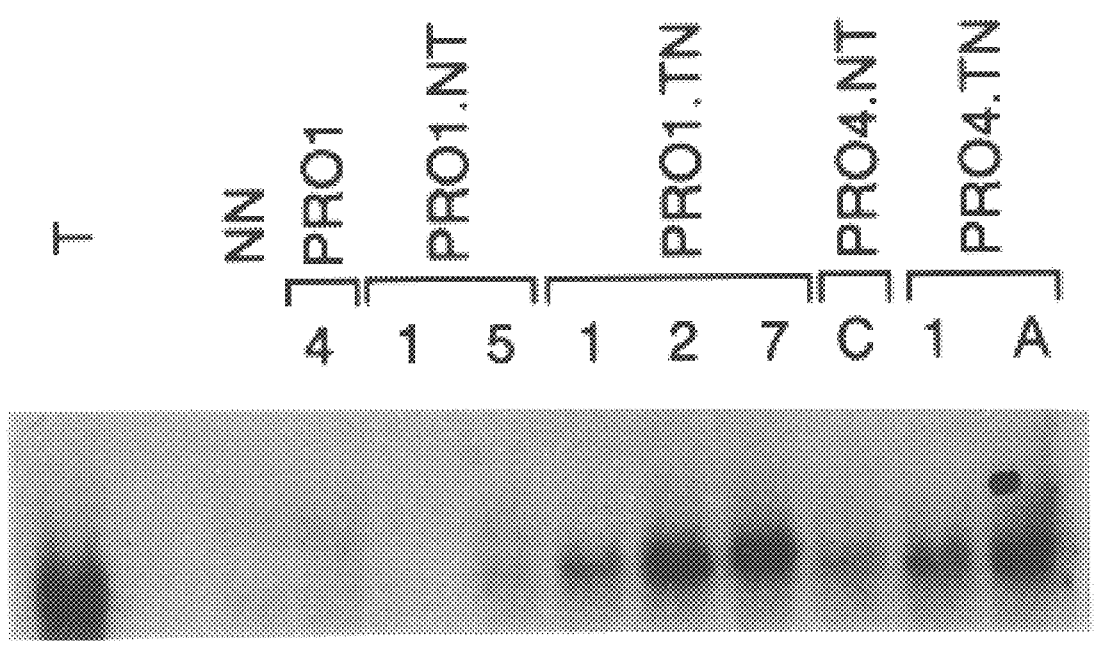
FIG. 5 is a Northern blot analysis of total RNA extracted from R1 plant lines transformed with PRO1-derived constructs. The different plant lines analyzed are indicated above each lane, with the prefix (corresponding to the construct) at the top and the suffix below.

Northern blot analyses were conducted to investigate whether the amounts of transgenic mRNA reflected the levels of accumulated proteins. FIG. 5 shows that the steady-state levels of most of the transgene-related mRNAs were between 1 and 5 pg/μg of total RNA, which are levels within the range found for transcripts from transgenes driven by the 35S promoter (data not shown). It was concluded that the levels of transgene-related mRNA did not account for the low levels of accumulation of transgenic proteins. Other experiments showed that the accumulation of certain transgenic proteins was greatly increased upon inoculation with TEV without affecting the amount of the corresponding steady-state mRNAs (see Section H of this example below).

G. Assays of pathogen derived resistance in transgenic plant lines.

The next step in the analysis of the transgenic lines was to determine if they were protected against TMV infection due to expression of TMV CP genes and accumulation of CP. The transformation vector contains, in addition to the target gene, and gene for selection of transformed cells, a gene to encode nopaline synthase, known as the nos gene. In most of the transgenic lines the nos gene is co-transformed with the other two genes. Appearance of the product of the gene, nopaline, can be readily scored by a simple assay, and serves as a marker to identify transgenic lines. In this example it was used to identify and score the number of transgenic individuals amongst a segregating population of progeny (R1) from the parental (Ro) transgenic line. A segregation Table 2 of this application shows the results of several representative experiments to illustrate the low level of protection found in R1 progeny of selected plant lines upon inoculation by TMV; each plant line was tested at least three times with similar results. In addition to untransformed tobacco plants, two different negative controls are used: plant PRO1–4 was transformed with a PRO1 construct lacking TMV CP sequences, and PRO4.TN-3 was considered to be a non-expressor as it did not show transgenic protein accumulation or nopaline accumulation. Control plant lines include nos$^{(-)}$ progeny non-transgenic plants, or transgenic plants that carry the vector only. Leaves of between four and eight plants were inoculated with TMV (40–100 mg/ml). As expected, the number of necrotic local lesions elicited on these lines did not differ from the number produced on untransformed plants (data not shown). Expression was determined in each plant by Western blot analysis or by accumulation of nopaline.

TABLE 2

Number of Lesions Produced in Transgenic Plant Lines Following Inoculation with TMV

| Plant Line[a] | Level of[c] Transgenic Protein | Number of Local Lesions[b] | | |
|---|---|---|---|---|
| | | Transgenic Expressors | Control | Non-expressors; or transgenic w/vector only |
| PRO1, TN-1 | ++ | 52 ± 34* | 112 ± 33 | ? |
| PRO1, TN-2 | + | 78 ± 33? | 111 ± 25 | |
| PRO1, TN-7 | ++ | 24 ± 8* | 45 ± 20 | |
| PRO1, TN-A | + | 142 ± 66* | 277 ± 31 | ? |
| PRO1, TN-1 | n.d. | 57 ± 35? | 97 ± 17 | |
| PRO1, TN-5 | n.d. | 85 ± 24* | 140 ± 38 | |
| PRO1, TN-1 | ++ | 40 ± 22* | 72 ± 12 | |
| PRO1, TN-A | ++ | 94 ± 19* | 131 ± 11 | |
| PRO1, TN-C | ++ | 51 ± 31* | 156 ± 42 | |

[a]Plant lines carrying the gene constructions described in FIG. 3. The final number or letter designates the transgenic plant line.
[b]The average number of necrotic local lesions ± standard deviation is given.
* indicates statistical difference from the number of lesions produced by the control lines.
[c]Levels of accumulated CP or CP-fusion proteins determined by Western blot analysis. ++ = >0.001% w/w, of total proteins; + = <0.001%, w/w, of total proteins; n.d. = not detected.

In plant lines PRO1.TN-1, PRO1.TN-7, PRO4.NT-C, PRO4.TN-1 and PRO4.TN-A, each of which accumulated higher levels of CP or CP:NIa fusion protein (see FIG. 4) than other lines, the number of local lesions on the expressors [i.e., CP (+)] was statistically lower as shown by the data in Table 2 than that produced either on the non-expressors of the same plant line (when applicable) or on untransformed plants. Taken together, the data indicate that transgenic accumulation of TMV CP using the proteinase cassette is correlated with protection against TMV infection. Interestingly, protection was also observed in plant lines accumulating uncleaved polyproteins (PRO4 constructs), although we cannot to rule out the possibility that this protection was due to the unspecified cleavage of TMV CP detected in some of these lines (as discussed above). Lines PRO1.TN-2 and PRO1.TN-A, which were among the lines with lower amounts of accumulated CP, showed only a slight reduction in the mean value of the number of local lesions when compared to controls (Table 2). As reported above, it was not possible to identify a plant line containing the construct PRO1.NT which accumulated the corresponding transgenic proteins. Nevertheless, two different plant lines transformed with this construct, PRO1.NT-1 and PRO1.NT-5, showed weak protection when nopaline accumulation was taken as a reporter of transformation (Table 2).

This result left open the possibility that these lines are actually expressors of TMV CP but at levels that were undetectable in our assays. R2 seeds were obtained from the most resistant lines and their progeny also were shown to accumulate TMV CP-related proteins of the expected size (not shown). Four R2 lines were selected for further study; PRO1.TN-1,4, PRO1.TN-7,2, PRO4.NT-C,2, and PRO4.TN-1,10. Each was a homozygous R-2 population. Half leaves were inoculated with either TMV (50 ng/ml) or TMV RNA (3 µg/ml). Between five and eight plants (one leaf per plant) were inoculated, depending on the plant line and the experiment. According to the data shown in Table 3, of this application, these plants were as protected against TMV infection as their parental lines when compared with non-transgenic plants. All value for inoculated plants were statistically lower than those shown by the corresponding untransformed control plant line at 95% confidence as determined by t Student's test. PRO1 constructs produced a polyprotein that is proteolytically processed; PRO4 constructs produced a non-processed polypeptide.

TABLE 3

Numbers of Lesions Produced Following Infection With TMV or TMV RNA of R2 Progeny[a]

| | Plant Line[b] | TMV | | TMV RNA | |
|---|---|---|---|---|---|
| Exp 1 | Non-transgenic | 72 ± 26 | | 106 ± 29 | |
| | 748 | 0 ± 0 | (0) | 64 ± 15 | (60) |
| | PRO1.TN-1,4 | 20 ± 21 | (28) | 15 ± 18 | (14) |
| | PRO1.TN-7,2 | 4 ± 2 | (6) | 13 ± 7 | (12) |
| Exp 2 | Non-transgenic | 151 ± 22 | | 91 ± 36 | |
| | 748 | 0 ± 0 | (0) | 35 ± 20 | (38) |
| | PRO4.NT-C2 | 47 ± 13 | (31) | 28 ± 12 | (31) |
| | PRO4.TN-110 | 86 ± 16 | (57) | 45 ± 6 | (49) |

[a]The average number of necrotic local lesions ± standard deviation per half leaf is given. Numbers in parenthesis indicate the percentage of the average number of necrotic local lesions when compared with the corresponding untransformed control. All values were statistically lower than those shown by the untransformed control at 95% confidence (Student's t test).
[b]Nontransgenic plants are N. tabacum cv. Xanthi NN; plant line 748 contains the CaMV 35 S promoter and TMV CP gene and accumulates large amounts of TMV coat protein; other plant lines are as described in Table 2 and FIG. 3. Each were homozygous R-2 populations; PRO1 constructs produced a polyprotein that is proteolytically processed; PRO4 constructs produced a non-processed polypeptide.

It was previously reported that TMV CP mediated protection is partially overcome by inoculation with viral RNA (Nelson et al., supra). To further characterize the protection in R2 plant lines, they were inoculated with TMV RNA and all were found to be protected against this virus to the same extent as against TMV (Table 3). This behavior is significantly different than that found with line 748, in which protection against TMV is much more effective than against TMV RNA (Table 3). In an additional control experiment, the R2 lines described above were challenged with the heterologous potato virus X (PVX) and the plants were found to be as susceptible to infection as the untransformed controls (data not shown). It has been recently reported that the transgenic expression of the NIa proteinase of tobacco vein mottling potyvius (TVMV) confers protection against infection by TVMV, but not against other poty rses (Maiti et al., supra). Similar results were obtained with the NIa protein of potato virus Y (PVY) (Vardi et al., supra). The R2 plant lines described here were subsequently challenged with TEV. As shown in Table 4 of this application, between 20 and 40% of the individuals of lines expressing the transgenes did not show symptoms after inoculation with dilutions of 1:1000 or 1:2000 of homogenates from TEV-infected plants.

TABLE 4

Susceptibility to Infection with TEV of R2 Progeny of Tobacco Plant Lines Transformed with PRO1 Contructs[a]

| Plant Line | Expt. 1 (1:100)[a] | Expt. 2 (1:1000) | | Expt. 3 (1:1000) | | Expt. 4 (1:2000) | | Totals at |
|---|---|---|---|---|---|---|---|---|
| | 7 dpi | 7 dpi | 14 dpi | 7 dpi | 14 dpi | 7 dpi | 14 dpi | 14 dpi[b] |
| NN | 8/8 | 8/8 | 8/8 | 8/8 | 8/8 | 5/8 | 7/8 | 23/24 (96) |
| PRO1.TN-1,4 | 8/8 | 2/8 | 5/8 | 5/6 | 5/6 | 2/6 | 2/6 | 12/20 (60) |
| PRO4.NT-C,2 | 8/8 | 8/8 | 8/8 | 7/8 | 7/8 | 2/8 | 3/8 | 18/24 (75) |
| PRO4.TN-1,10 | 8/8 | 6/8 | 8/8 | 5/8 | 6/8 | 4/8 | 5/8 | 19/24 (79) |

[a]The results of three experiments are presented; the ratios given in parenthesis represent the dilution of TEV-infected tobacco sap used as inoculum. Each plant was scored for visual symptoms at 7 and 14 days post inoculation (dpi).
[b]Combined number of plants with symptoms over the total number of plants analyzed in experiments 2, 3, and 4, at 14 dpi. The percentage of plants with symptoms is presented in parenthesis.

Figure 6A:
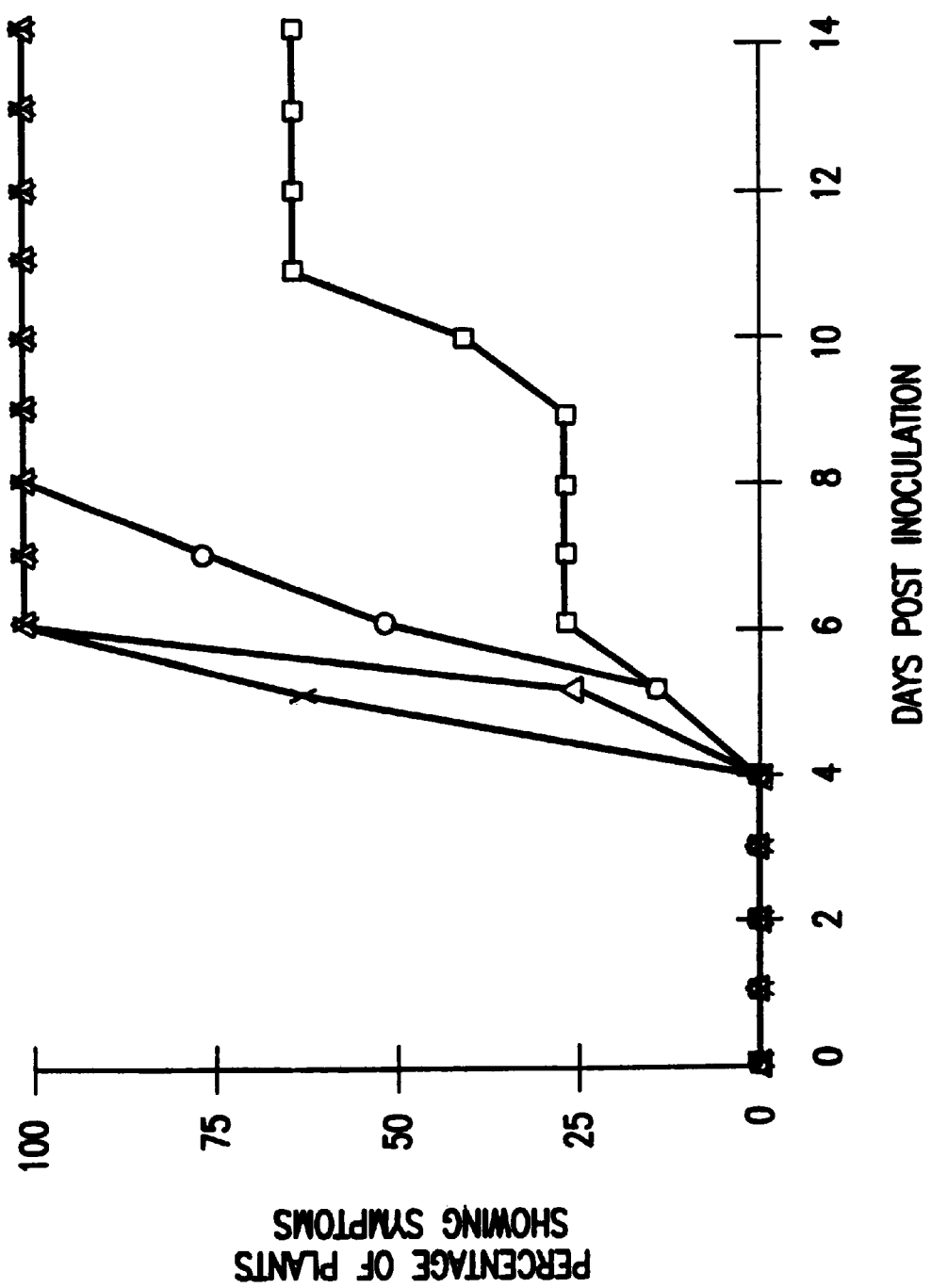
FIGS. 6A–6B show the level of protection against TEV infection in R2 plant lines transformed with PRO1-derived constructs.
Figure 6B:
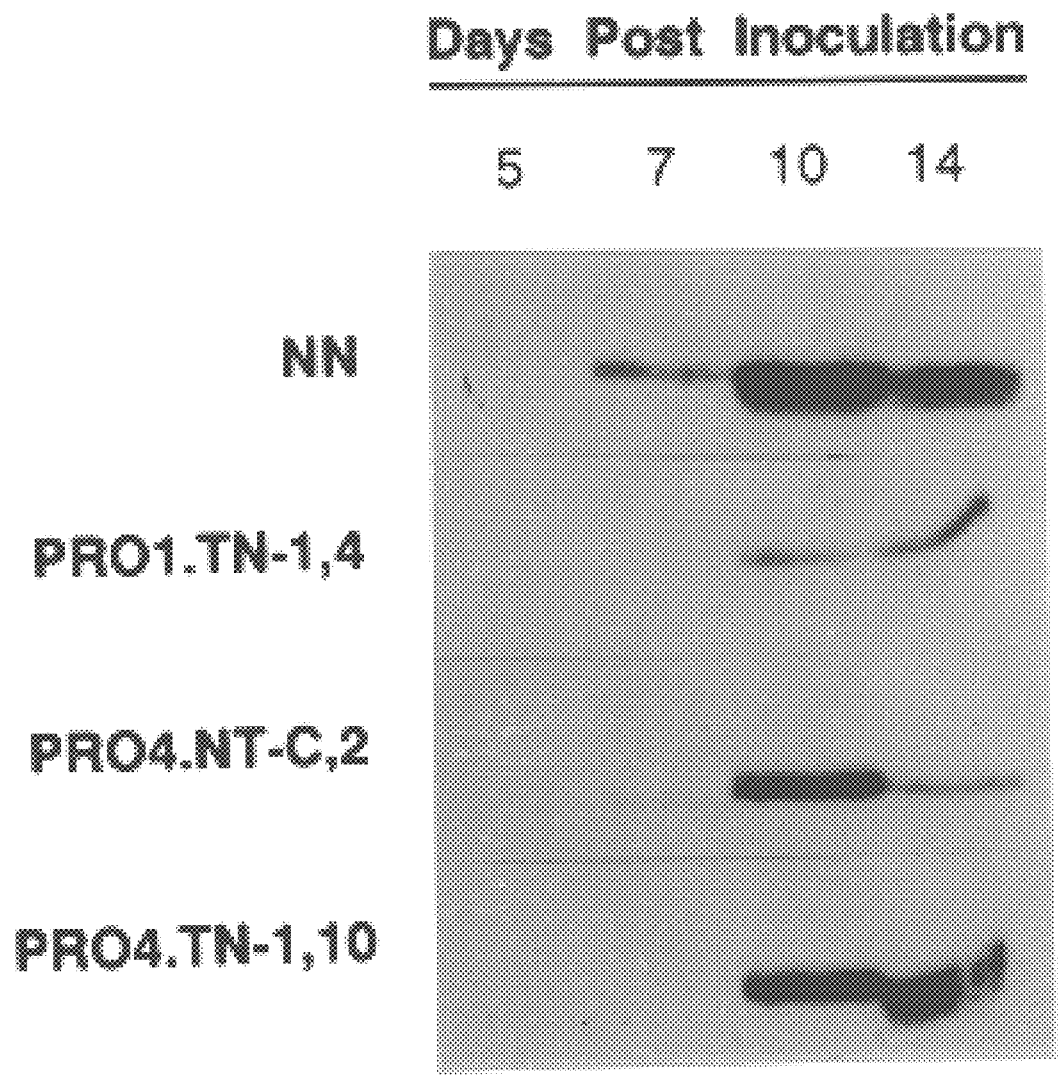

When the level of inoculum was a 1:100 dilution no protection was evident in any plant line (Table 4, experiment 1). Plant line 748 was equally as susceptible to TEV as non-transgenic Xanthi NN (not shown). FIG. 6 presents in greater detail the results of one experiment, showing not only that some plants did not become symptomatic but also that there was a clear delay in the appearance of symptoms in individuals that became infected (FIG. 6A). The absence or delay in the appearance of symptoms correlated with reduced accumulation of the challenging virus in the systemic leaves, as evidenced by the detection of the TEV capsid protein by Western blot analysis (FIG. 6B). Also, the systemically infected leaves of transgenic plants that eventually became infected showed symptoms that were milder than those of untransformed plants.

H. Increase of transgenic protein accumulation upon infection with TEV.

Figure 7:
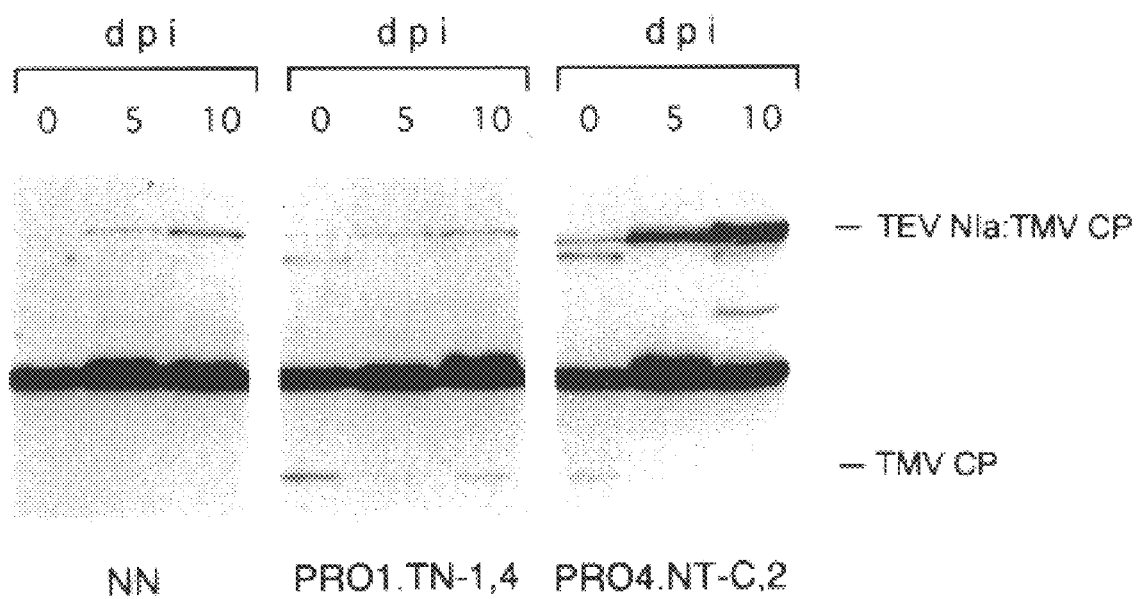
FIG. 7 is a photograph of a Western blot analysis showing changes in accumulation of transgenic proteins upon TEV infection. Protein extracts immunostained with an anti-TMV CP antiserum from TEV-infected systemic leaves of untransformed tobacco NN and plant lines PRO1.TN-1,4 and PRO4.NT-C,2 were analyzed at 0, 5, and 10 days post inoculation (dpi). The migrations of the TEV NIa:TMV CP fusion protein and the TMV CP that accumulate, respectively, in plant lines PRO1.TN-1,4 and PRO1.NT-C,2 is indicated on the right side.

Based on the amounts of transgenic viral proteins that accumulated, little or no protection against virus infection was predicted. During several of our experiments, systemic plant tissue was harvested at different times after inoculation with TEV and analyzed for the accumulation of transgenic proteins using the anti-TMV CP antiserum. Western blot analysis of protein extracts from TEV-infected systemic leaves of untransformed tobacco NN and plant lines PRO1.TN-1,4 and PRO4.NT-C,2 was performed at 0, 5, and 10 days post inoculation (dpi). Plants were infected with a 1:500 dilution of sap from TEV-infected tobacco. Proteins were immunostained with an anti-TMV CP antiserum. However, as shown by the data in FIG. 7, there was an unexpected significant increase in the amount of uncleaved fusion protein in plant lines PRO4.NT-C,2 and PRO4.TN-1,10 (not shown), but not in plant line PRO1.TN-1,4, in which the polyprotein is cleaved. The amount of uncleaved proteins was greater in plants that became infected and accumulated TEV, indicating that this result was a direct consequence of infection with TEV. Furthermore, the small amounts of TMV CP detected in line PRO4.NT-C,2 disappeared with TEV infection (FIG. 7). To eliminate the possibility that accumulation of the fusion protein was a consequence of plant age rather than of viral infection, plants were either mock- or TEV-inoculated and tissue was analyzed at ten days post inoculation for the presence of the fusion protein and TEV coat protein.

As shown by the data in FIG. 8, the increase in the amount of fusion proteins, but not of TMV CP, was confirmed by Western blots to be dependent on TEV infection. Systemic tissue was harvested at 10 days post inoculation for subsequent analysis utilizing a 1:500 dilution of sap from TEV-infected tobacco immunostained with an anti-TEV CP antibody (FIG. 8A) or with an anti-TMV CP antiserum (FIG. 8B). Considering that the increase in the level of the fusion protein was observed only in TEV infected plant lines that accumulated PRO4 (FIGS. 7 and 8B), this accumulation could result from increased gene expression or protein stability. Northern blot analysis was carried out with ROA isolated from upper leaves of plants that were infected with TEV, using as probe total RNAs hybridized to a 32P labeled TMV CP-specific DNA probe derived from the TMV coat protein gene. 20 $\mu$g of total RNA were loaded in all lanes. In lane T a mixture of 100 pg of transcript synthesized in vitro and 20 $\mu$g of total RNA from untransformed tobacco was analyzed. As shown in FIG. 8C, such analyses confirmed that steady 0-state levels of transgene-specific mRNAs remained unchanged in all the plants before and after infection. Therefore, it was concluded that the increased accumulation of transgenic polyprotein following infection with TEV is most probably a consequence of protein stabilization.

Data presented in FIG. 4 confirm that the TMV CP is properly translated and processed as a result of the expression of transgenic chimeric genes derived from PRO1. Processing of the polyproteins was NIa specific, since processing was largely abolished by mutations in the heptapeptide that is recognized by NIa. No precursor polyprotein was detected in plant lines that harbor the construct PRO1.TN, indicating that processing at the N terminus of the proteinase is highly efficient. In these plant lines the TMV CP apparently retained the additional amino acid residues at its termini, and it is predicted that these amino acids will be located at the surface of the protein (Namba et al., 1989). In plant lines that express the mutated PRO4 constructs, minor amounts of TMV CP were detected (FIG. 4), presumably due either to unspecified proteolysis by cellular proteases or due to low levels of activity by NIa on the mutant sequences.

Relatively low levels of transgenic proteins accumulated in the plant lines analyzed. Studies with other CP genes (including other potyvirus CPs) expressed in tobacco plants using PRO1-derived constructs yielded similar results with correspondingly low levels of pathology derived resistance (PDR). It is worth noting that lines that express the transgene were more readily obtained when TMV CP was positioned at the N terminus rather than at the C terminus of the polyprotein. This observation could indicate that higher levels of accumulation result when target proteins are translated preceding the NIa sequence. In a previous report in which the β-glucuronidase gene (uida) was fused to the TEV NIa gene to study the nuclear targeting of the viral protein, GUS activity was higher when the reporter protein was translated at the N terminus of the proteinase (Restrepo-Hartwig et al., *Plant Cell* 2:987–998, 1990).

J. Viral genes expressed as part of the PRO1 cassette have biological activity in conferring pathogen derived resistance.

Despite the low accumulation of transgenic proteins, selected transgenic plants exhibited a low but reproducible degree of protection against infection by the TMV and TEV, and also against some related tobamoviruses (data not shown). As shown by the data in Table 4, the phenotype of protection against TMV was modest when compared to plant line 748; however, resistance appeared to be qualitatively different since it was equally effective against TMV and TMV RNA. Although not wishing to be bound by the mechanism, it is believed that the molecular mechanism operating in the plant lines employed in this experiment may be different from that in line 748, in which inhibition of virion disassembly is a major component of resistance (reviewed by Reimann-Philipp and Beachy, *Sem. Virol.*, 4:349–356, 1993).

The plant lines that express NIa sequences were protected to a low degree against TEV, in agreement with previously reported data from studies with other potyviruses (Maiti et al., supra; Vardi et al., supra). The data do not enable us to determine whether the protection observed in plants that express genes encoding fusion proteins is due to the minor release of NIa, to the complete polyprotein, or to the corresponding transcript.

K. Effect of TEV infection on accumulation of transgenic proteins.

There are numerous reports in which transgenic viral proteins did not accumulate to high levels; although, PDR was achieved (Fitchen and Beachy, *Ann. Rev. Microbiol.*, 47:739–763, 1993). In most cases it is not possible to study the accumulation of transgenic proteins following challenge by virus because the transgenes encode proteins that cannot be readily distinguished from those produced by the challenge. Farinelli, et al. (*BioTechnology*, 10:1020–1025, 1992) reported that accumulation of transgenic CP from PVYN increased upon inoculation of the plants with PVYO using strain-specific antibodies. The data provided by this study as shown in FIGS. 7 and 8 demonstrate that the accumulation of NIa:CP fusion proteins, but not of CP cleaved from the polyprotein, increased following TEV infection. This increase was specific to TEV infection since it did not occur when plants were infected with PVY or TMV (data not shown). Since it was observed only with fusion proteins, accumulation of the transgenic protein was most likely due to protein stabilization. Furthermore, as shown by FIG. 8C, the levels of transcript were not changed by TEV infection. This would imply that in the absence of viral infection transgenic proteins do not accumulate well due to protein instability.

Although not wishing to be bound by mechanism, it is believed that the fusion proteins are stabilized because of their interaction with products produced during TEV infection. Transgenic proteins containing TEV NIa may be included in the nuclear inclusions formed by the NIa and NIb replicase following virus infection. The accumulation of the NIa:CP fusion reported here is apparently different from the accumulation of transgenic RNA. Lindbo, et al., *Plant Cell*, 5:1749–1759, 1993 reported a marked decrease in the steady-state levels of transgenic mRNA as a consequence of an co-suppression mechanism mediated by RNA. This mechanism may operate in plants prior to viral infection and, following challenge, be responsible for the inhibition of viral replication in some examples of pathogen derived resistance.

EXAMPLE 12

In this study the capacity of well characterized murine zona pellucida epitope(s) presented in the context of TMV CP to induce antibodies and to mediate antibody based contraception is presented. A peptide sequence from ZP3 was used to construct a chimeric TMV CP antigen for immunization. The ZP3 sequence included the entire B cell epitope associated with contraception (Millar, et al., supra), $ZP3_{336-342}$, but lacked the critical amino terminal residue of the T cell epitope linked to severe autoimmune oophoritis (Rhim, et al., supra; A-M. Luo, et al., supra). The immediate objectives of this study were to evaluate the quality of the antibody response due to parenteral immunization with this chimeric antigen, to evaluate female mice for contraception subsequent to the stimulation of antibody production and to observe ovaries for pathological effects of the immunization.

A. Construction of modified virus.

The sequence of a cDNA clone of a fragment of the TMV genome including the gene for the coat protein was modified by oligodeoxyribonucleotide directed mutagenesis to contain a peptide from the murine zona pellucida ZP3 protein. The resulting coat protein gene contained an additional 13 codons encoding residues 331 to 343 of murine ZP3 (SEQ ID NO: 16) between the codons for residues 154 and 155 of the coat protein. The coat protein gene of a clone used to prepare infectious RNA transcripts of TMV was replaced by this modified gene after cleavage at flanking restriction enzyme recognition sites. A cDNA clone of the coat protein coding sequence of TMV strain U1 (common) and flanking sequences, nucleotides 5459–6395 (P. Goelet, et al., supra, in pBluescript KS+ was constructed by subcloning of the appropriate NcoI-KpnI fragment from pU3/12-4 (Holt and Beachy, supra) and used as a template for oligonucleotide directed PCR mutagenesis. Oligonucleotides GTCTTG-GTCCGTGTATTTGGAATTGGAGCTA CTAGAAGA GGTCCAAACCAAAC (SEQ ID NO: 26) and AATAAC-CCTCACTAAAGGGA (SEQ ID NO:27)(T3), or CCAAATACACGGACCAAGACAAGGTCCT-GCAACTTGAGG (SEQ ID NO:28) and TAATACGACTCACTATAGGGAGA(T7) (SEQ ID NO: 29) were used with template digested with KpnI or NcoI respectively, to direct the synthesis of overlapping partial cDNA copies of the TMV coat protein gene containing 39 additional nucleotides encoding the $ZP3_{331-343}$ peptide between amino acids 154 and 155 of the TMV CP. The resulting DNA fragments were used to direct a second round of PCR synthesis producing the full length NcoI-KpnI fragment with the additional ZP3-peptide encoding sequence. Cycle parameters used for the PCR were 95° C., 30 sec; 47° C., 60 sec; 72° C., 60 sec for 25 cycles in the first round followed by a 72° C., 600 sec incubation and 95° C., 30 sec; 42° C., 60 sec; 72° C., 60 sec for 20 cycles followed by a 72° C., 600 sec incubation in the second round. This second round of PCR yielded a modified NcoI-KpnI fragment, which was inserted into the homologous sites of the TMV cDNA fragment in a derivative of pU3/12-4 yielding a modified full length cDNA clone of TMV. The plasmid pU3/12-4 is described in Holt and Beachy, 1991, supra, which is incorporated herein by reference in its entirety. The sequence of this recombinant TMV CP gene was verified by sequencing the modified coat protein sequence with oligodeoxyribonucleotides flanking and internal to the TMV gene.

B. In vitro transcription.

RNA transcripts of the linearized plasmid containing the hybrid coat protein gene were prepared as described (Holt and Beachy, supra). Briefly, T7 RNA polymerase was used to catalyze synthesis of full length TMV genomes including the modified coat protein gene. Typically 2 µg of linear plasmid provided sufficient material for inoculation of 10 to 20 leaves.

C. Infection of tobacco.

Primary infections of Xanthi nn tobacco leaves were initiated with in vitro transcription products described above. Transcription product was diluted 1/10 in 20 mM sodium phosphate pH 7.2, and 100 ml was applied to expanding tobacco leaves. Inoculation was effected by gentle rubbing in the presence of carborundum (320 grit; Fisher, Pittsburgh, Pa.) to spread the inoculum and abrade the leaf surface. Leaves were rinsed with water immediately after inoculation to remove excess carborundum. Plants were isolated in a greenhouse and maintained with normal watering and fertilization. Products of in vitro transcription from the hybrid clone were used to inoculate young tobacco leaves. For large scale inoculation, crude homogenate of infected leaves from the primary infections was substituted for in vitro transcription product. Symptoms typical of TMV infection were observed on newly formed leaves of the inoculated plants by 14 days post inoculation with the exception that necrotic lesions were not formed. The modified virus induced typical infection symptoms including a mosaic pattern on leaves and like wild type virus, but unlike some other TMV with modified coat proteins, did not induce a necrotic response on *Nicotiana tabacum* cv Xanthii nn (J. R. Haynes, et al., *Biotechnology* 4:637, 1986). Modified virus spread throughout infected plants facilitating production of large amounts of protein. The viral genome encoding the hybrid coat protein is stable at for least 3 successive passages. Infected plant material retains infectivity and antigenicity when stored at −20° C., providing a convenient method of storing virus as inoculum or antigen.

D. Sampling of leaf tissue.

Figure 9A:
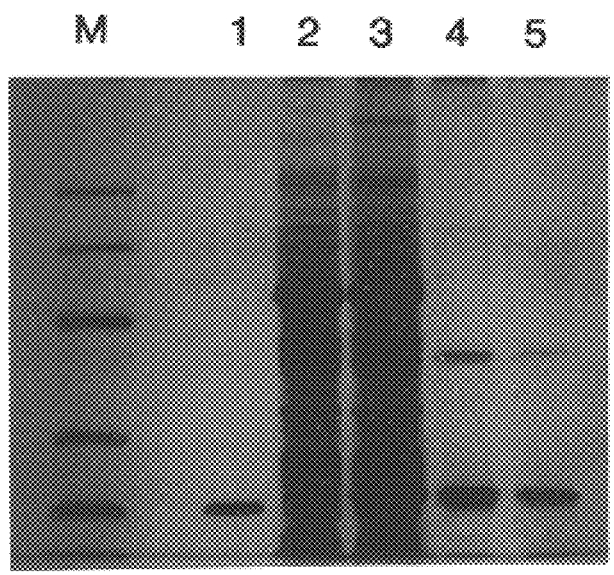
FIGS. 9A–9B show photographs of an SDS polyacrylamide gel separation and an immunoblot of proteins extracted from leaves of tobacco plants.
Figure 9B:
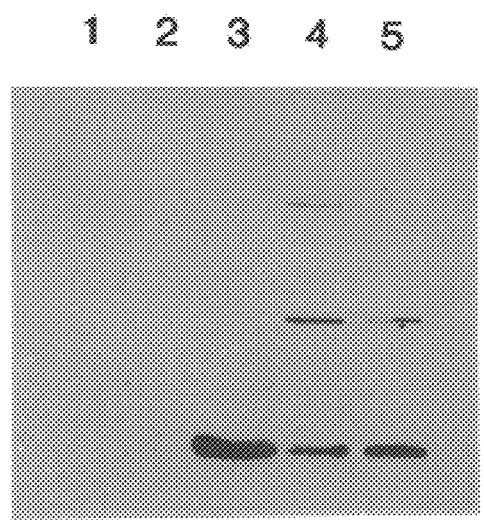
Figure 10A:
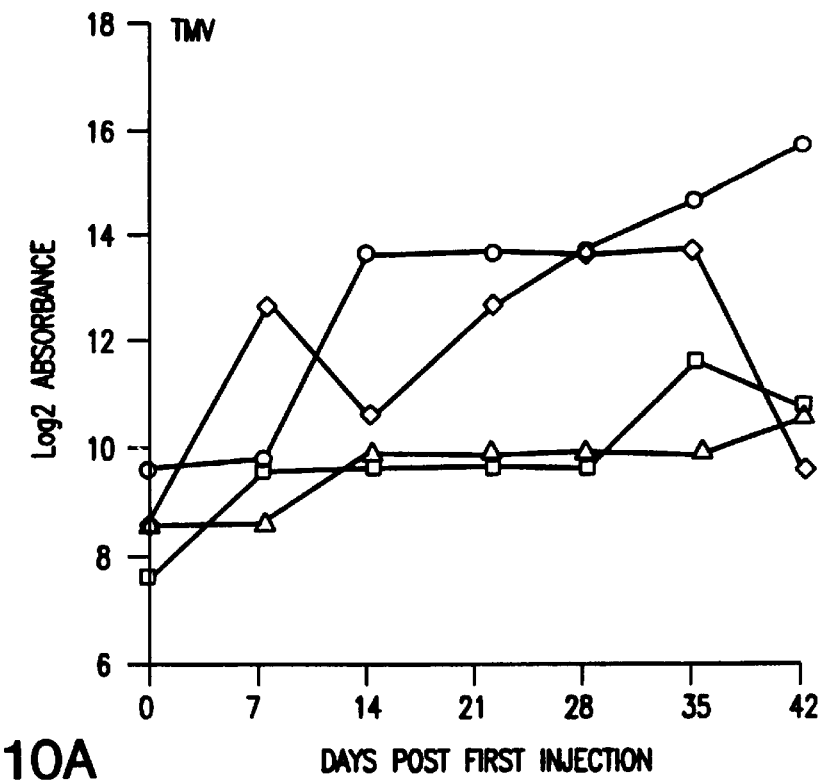
FIGS. 10A–10E display graphs showing the serum antibody response of mice immunized i.p. with TMV-ZP3$_{331-343}$ measured by ELISA on microtiter plates coated with TMV CP or a KLH-ZP3 $_{331-343}$ conjugate. Murine antibody was detected with a horseradish peroxidase conjugate of goat anti-mouse kappa chain secondary antibody. Each point represents the log2 dilution of sera required to reach 120% of baseline absorbance. Baseline absorbance was defined as the absorbance displayed in microtiter wells that received secondary antibody but not primary mouse serum. ELISA microtiter plates included a standard dilution of a pooled anti-ZP3$_{331-343}$ serum, which was developed to the same absorbance endpoint on each plate, and each assay was performed at least twice.
Figure 10B:
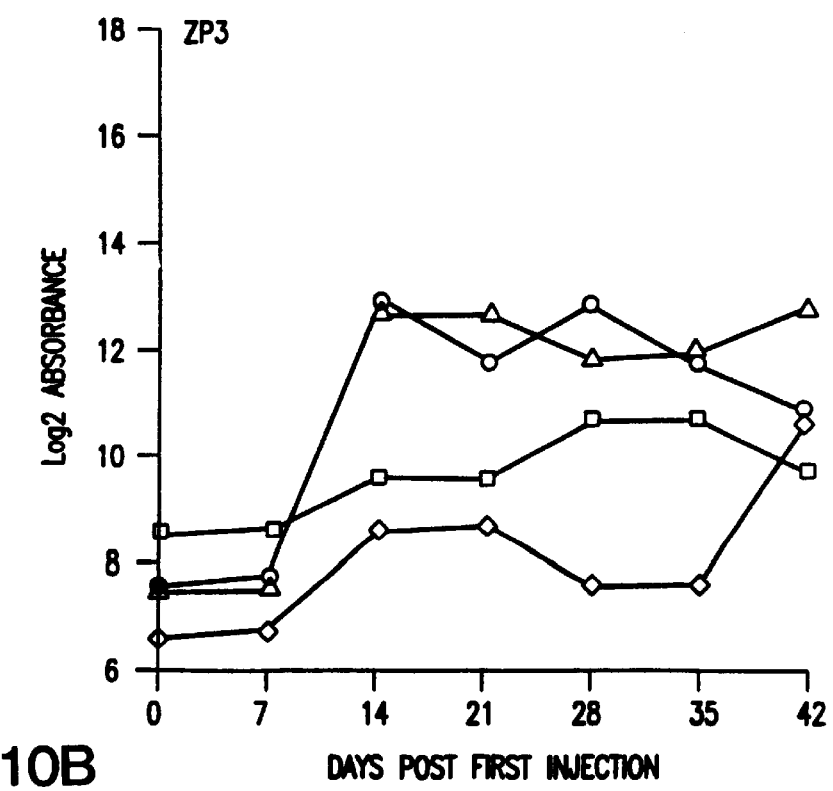
Figure 10C:
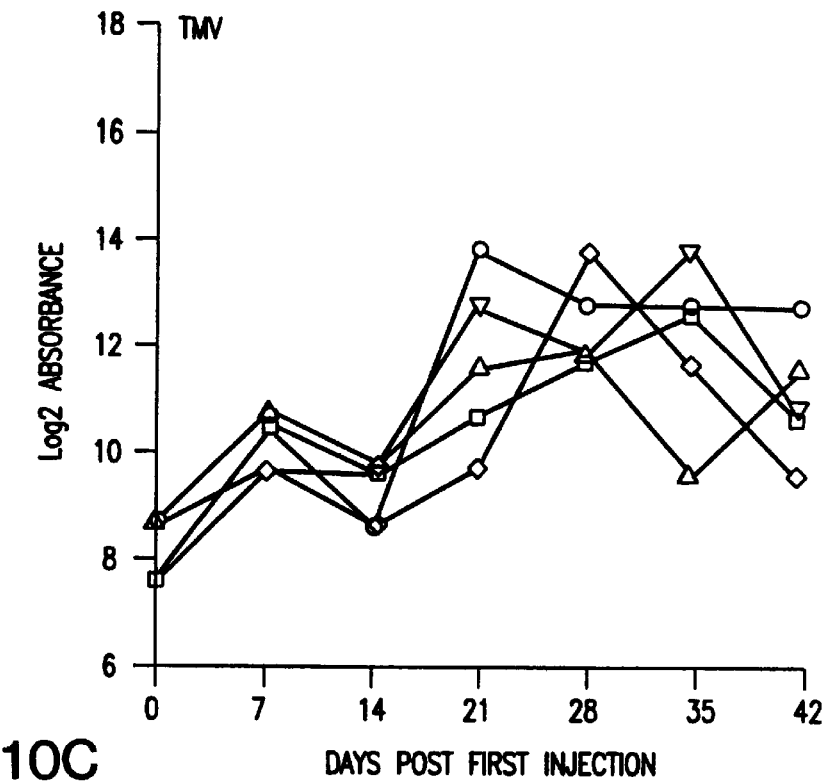
Figure 10D:
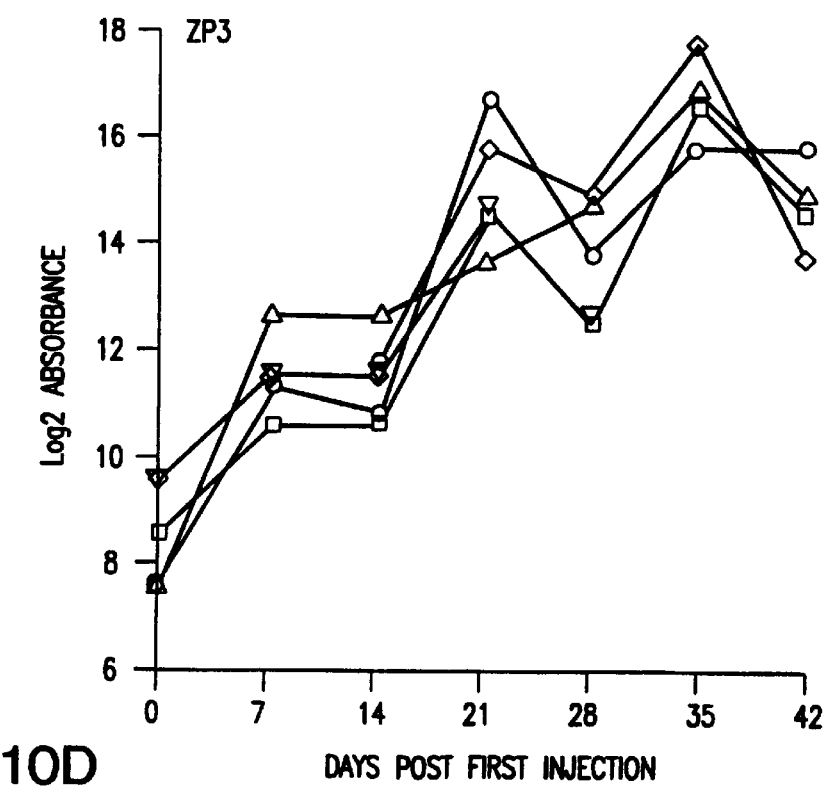
Figure 10E:
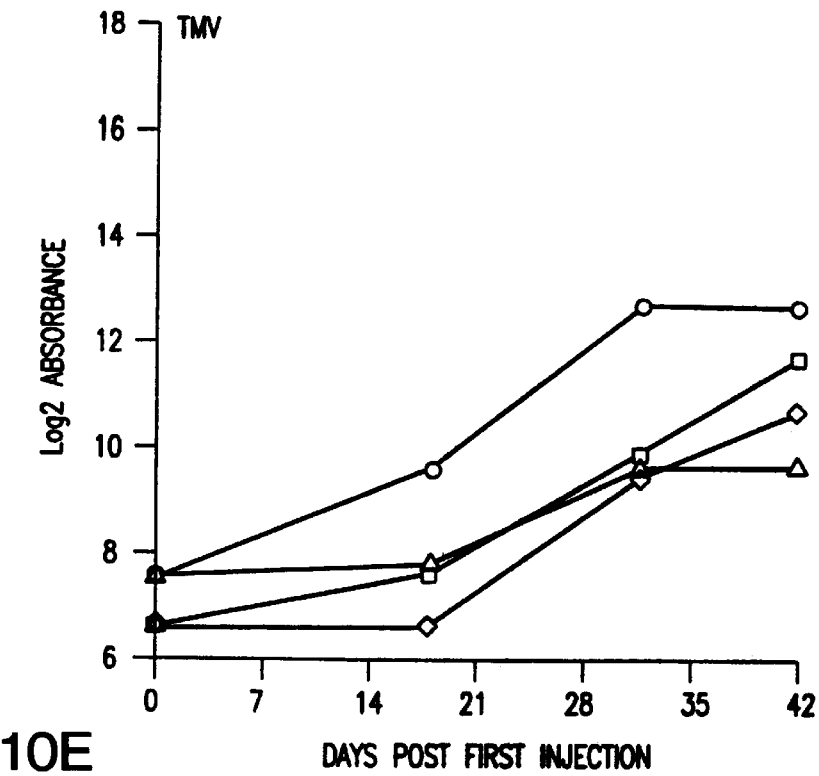
Figure 10F:
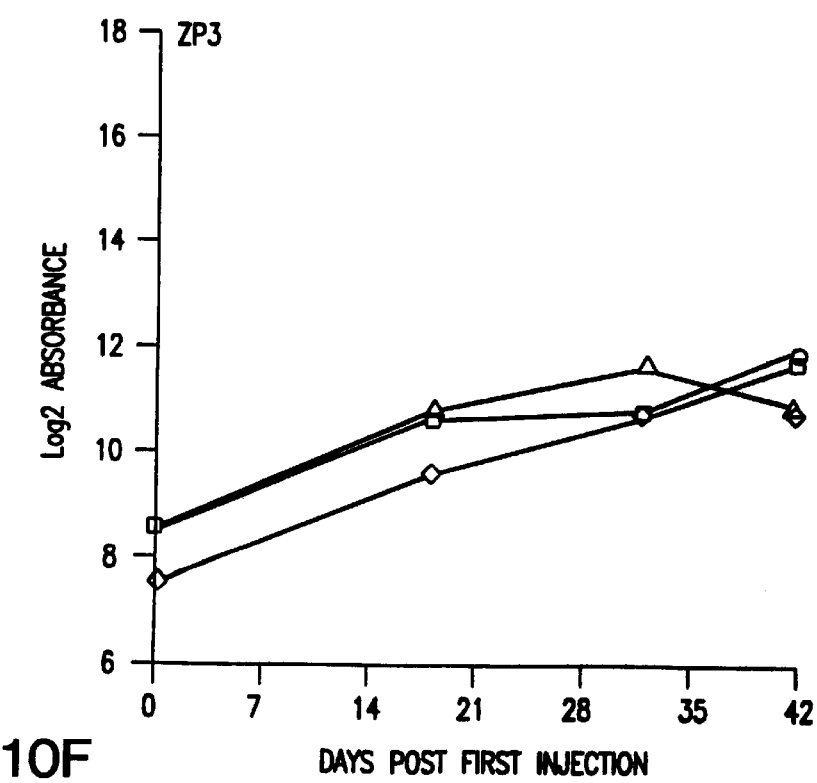
FIG. 10F shows the serum titer to KLH-ZP3 of BALB/cBy mice from experiment 3.

One cm diameter leaf discs taken from infected leaves were frozen, thawed, and homogenized in 50 ml sample buffer (0.28M Tris pH 6.8, 2% SDS, 20% glycerol, 1% 2-mercaptoethanol, 0.25% bromophenol blue). Proteins remaining in the supernatant after boiling and centrifugation at 13,000×g for 5 minutes were resolved by SDS-PAGE. Accumulation of virus-encoded hybrid coat protein was monitored by analysis of tissue samples from the infected plant leaves. As shown in FIG. 9A, an abundant protein species migrating slightly more slowly on SDS-PAGE than wild type TMV coat protein was detected in extracts from plants infected with the modified virus. The intensity of Coomassie blue staining of the modified coat protein relative to staining of other proteins in leaf extracts approximated that of native TMV coat protein in leaf extracts of plants infected with wild type virus. The intensity of staining of the modified coat protein was also similar to that of the large subunit of ribulosebisphosphate carboxylase, indicating a similar concentration in infected leaves. Sampling of upper uninoculated leaves revealed the presence of the hybrid coat protein, indicating that infection by the modified virus spread systemically, although at a somewhat slower rate than the wild type virus. As shown in FIG. 9B, the ZP3 epitope in the recombinant TMV CP was detected by a rat monoclonal antibody (IE-10) specific for $ZP3_{336-342}$ (I. J. East, et al., supra) on Western blots of proteins in crude leaf extract and in each of the partially purified virus fractions.

For isolation of bulk antigen, leaves were harvested 14 days post inoculation and stored at −20° C. These leaves were thawed and extensively ground in a chilled mortar and pestle in 1 ml/g of 50 mM Tris pH 7.4. Homogenate was separated into a primary supernatant and primary pellet fraction by centrifugation at 4,400×g for 20 minutes at 4° C. The primary supernatant fraction was centrifuged again and its pellet discarded. One tenth volume of 30% PEG (6,000)/ 10% NaCl was added to the supernatant, and the mixture was incubated at 4° C. with stirring for 2h. The mixture was centrifuged at 14,000×g for 20 minutes at 4° C., and the supernatant was discarded. The pellet was disrupted with ultrasonic treatment in deionized-distilled water and repelleted at 153,000×g for 90 minutes at 20° C. For use as antigen this pellet was resuspended in PBS at 1 mg modified coat protein/ml with ultrasonic disruption. For analysis by electron microscope (EM) or SDS-PAGE, the pellet was resuspended in deionized-distilled water by ultrasonic disruption.

The primary pellet from the initial centrifugation step was ground in a mortar and pestle, washed and repelleted five times in a series of buffers: 50 mM Tris pH 7.4; 50 mM Tris pH 7.4+5% Triton X100; 50 mM Tris pH 7.4+1% Triton X100; and finally twice with 50 mM Tris pH 7.4. The supernatant from each wash was discarded and the final washed pellet was analyzed by SDS-PAGE and EM after resuspension in deionized-distilled water by ultrasonic disruption.

The coat protein in the soluble fraction, once pelleted with PEG, could not be solubilized. Resuspension of this fraction could be achieved with 1 M acetic acid. While this PEG precipitated fraction accounted for only 10% of the extractable antigen, it lacked the high concentration of cell wall debris found in the primary insoluble fraction. The yield of antigen from infected tobacco was typically 100 mg per cm$^2$ of leaf. This is equivalent to approximately 25 µg of antigen from one mature greenhouse grown tobacco plant. The modified coat protein accumulates to concentrations as much as 2.5 mg per gram of leaf tissue in the leaves of infected plants, and is easily purified in two fractions from the bulk of plant proteins without chromatographic methods. These fractions contain insoluble, particulate antigen at high concentration. The primary pellet fraction is highly enriched in viral protein but contains significant amounts of plant cell wall debris, while the primary supernatant fraction is composed largely of virus-like particles. Neither formulation of the viral coat protein could be solubilized in neutral pH aqueous buffers.

This particulate character of the TMV CP antigen may have a positive impact on the magnitude and duration of the immune response. Whole TMV particles have been demonstrated to induce a more vigorous and persistent serum antibody response than either soluble TMV coat protein or reaggregated coat protein (F. Loor, et al., *Virology* 33:215, 1967). Whole TMV persists at the site of injection longer than either of these coat protein preparations maintaining a persistent and high local concentration of antigen.

E. Electron microscopic analysis of virus-like particles.

Figure 12A:
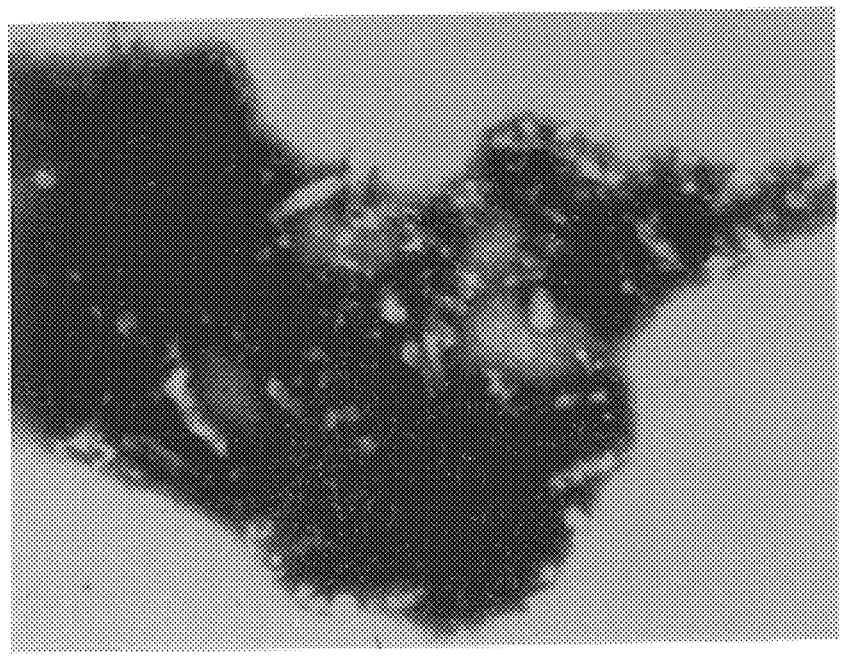
FIGS. 12A–12B show electron micrographs of insoluble TMV-virus like particles isolated from leaves infected with recombinant TMV-ZP3$_{331-343}$ RNA. The bar equals 100 nm.
Figure 12B:
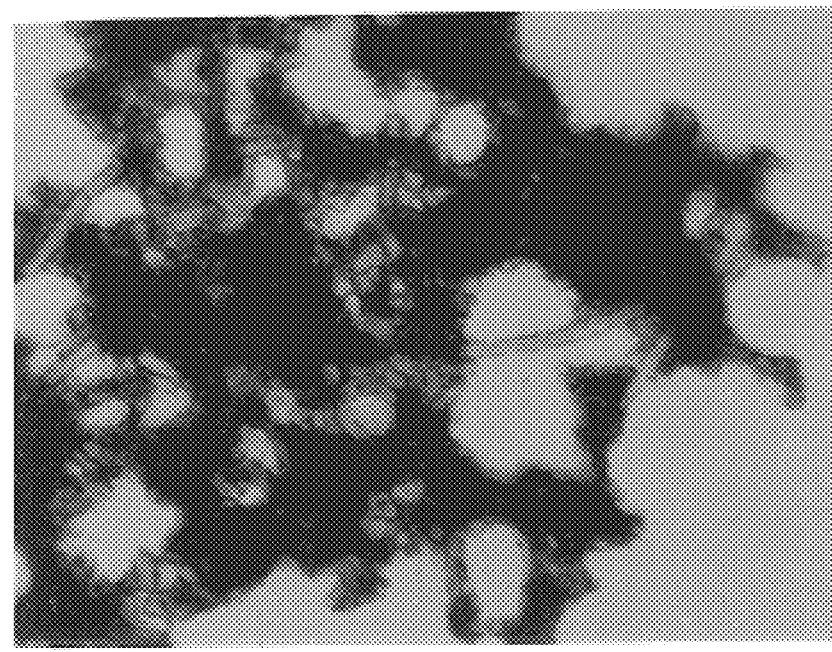

The partially purified leaf extracts described above were applied to carbon-film coated copper grids. Material was negatively stained with uranylacetate and examined in a Hitachi 600 electron microscope at 60,000 magnification. EM observation of negatively stained material from the two partially purified fractions represented in FIG. 9 (lanes 4 and 5) showed that both contained rod-shaped particles (FIG. 12). The particles in the primary pellet fraction were about 16 nm in diameter, similar to the observed 18 nm diameter of wild type virus. The length of the rods was highly variable, but was much shorter than 300 nm, the length of wild-type TMV virions. Penetration of stain into a central channel could be seen as is observed with the wild type virus, and striations with 2.5 nm spacing could be observed which is also similar to wild-type TMV particles (2.3 nm).

The transgenic coat protein carrying a 13 amino acid fragment of the murine zona pellucida ZP3 protein is robust, is not degraded in the leaves of plants infected with modified virus and assembles into rod like particles. These particles were observed to be smaller than full length wild type TMV particles which may be due in part to the ultrasonic disruption of antigen prior to evaluation by EM. Reduced stability of the rod may also result from the presence of the ZP3 epitope near the carboxy terminus of the coat protein.

F. Immunization of Mice.

Female C57BL/6J or BALB/cBy were acquired from the Scripps Research Institute rodent breeding colony at 4 to 5 weeks of age. Immunizations were initiated with mice of 5 to 6 weeks of age. During experiments mice were housed in sanitized cages, four mice per cage except during mating, and were provided sterile food and water ad libitum. Mice were immunized parenterally with virus particles suspended in phosphate buffered saline (PBS) emulsified with MPL-TDM adjuvant (RIBI Immunochemicals Research, Hamilton, Mont.) according to the manufacturer's instructions. For the initial immunization, approximately 50 μg of hybrid TMV coat protein were injected in 100 ml into the peritoneal cavity of mice and 50 μg of hybrid TMV coat protein were injected subcutaneously in 100 ml in the neck region of C57BL/6J or BALB/cBy mice. Subsequent immunizations at 32 days (Experiment 1) or 13 and 22 days (Experiment 2) or 13 and 27 days (Experiment 3) contained 50 μg in 200 ml of PBS/MPL-TDM, and were divided equally between subcutaneous and parenteral injection. Control mice received injection similar injections of wild type TMV coat protein.

G. Serum collection and enzyme immunoassay of antiserum.

Serum was collected from mice prior to immunization and at weekly intervals after the initial immunization by withdrawing approximately 200 ml of blood from an orbital sinus cavity. After removal of cells by centrifugation, serum samples were stored frozen until evaluation by ELISA or Western blotting. Serum titers of antibody recognizing either TMV coat protein or $ZP3_{331-343}$ were determined by limiting dilution of antisera on microtiter plants coated with authentic TMV coat protein or with $ZP3_{331-343}$ conjugated to KLH with sulfoMBS, (Pierce Chemical Co., Rockford, Ill.) via the amino terminal cysteyl residue of the synthetic ZP3 peptide: CSSSSNGHPQFQR (SEQ ID NO: 30). Antibodies recognizing the immobilized antigens were detected by oxidation of 2,2'-azino-bis (−3-ethylbenz-thiazoline-6-sulfonic acid) diamonium salt, (Boehringer Mannheim, Indianapolis, Ind.), (ABTS) after decoration with a horseradish peroxidase conjugate of goat anti-mouse kappa chain antiserum (Southern Biotechnology Associates, Birmingham, Ala.). Microtiter plates (Maxisorp, Nunc, Naperville, Ill.) were coated with a 50 ml suspension of either TMV CP or $ZP3_{331-343}$ conjugated to KLH in PBS pH 7.4 for 2 hours at room temperature, then washed with deionized, distilled water and blocked with 200 ml 2% BSA in PBS for 1 hour at 37° C. All sera were diluted initially at least 1:100 in 2% normal horse serum/PBS and diluted serially 1:2 in the same buffer as the initial dilution and incubated 50 ml/well for 2h at 37° C. After washing with deionized, distilled water a 50 ml volume of secondary antibody solution (1:2000) in TBS-tween 20 (TBST)+2% horse serum was incubated in each well for 2h at 37° C. Wells were washed with deionized, distilled water and developed in a solution of 20 mg/ml of ABTS in 0.1 M citrate pH 4.0 containing 0.01% $H_2O_2$.

Serum antibody titers against $ZP3_{331-343}$ and TMV coat protein are shown in FIG. 2. Serum antibodies in BALB/CBy mice (experiment 2) specific for $ZP3_{331-343}$ and for TMV coat protein were observed by 21 days after the initial injection. Among C57BL/6J mice (experiment 1), three mice demonstrated ZP3 and TMV coat protein specific responses by 14 days after initial injection. Serum antibody response was measured by ELISA on microtiter plates coated with TMV CP or a KLH-$ZP3_{331-343}$ conjugate. Murine antibody was detected with a horseradish peroxidase conjugate of goat anti-mouse kappa chain secondary antibody. The comparison of serum titers in BALB/CBy and C57BL/6J mice in FIG. 10 illustrates a weaker antibody response in the C57BL/6J genotype to the modified TMV coat protein antigen. This difference in antibody response was more pronounced for the $ZP3_{331-343}$ specific antibodies than for the TMV coat protein specific antibodies.

Figure 11:
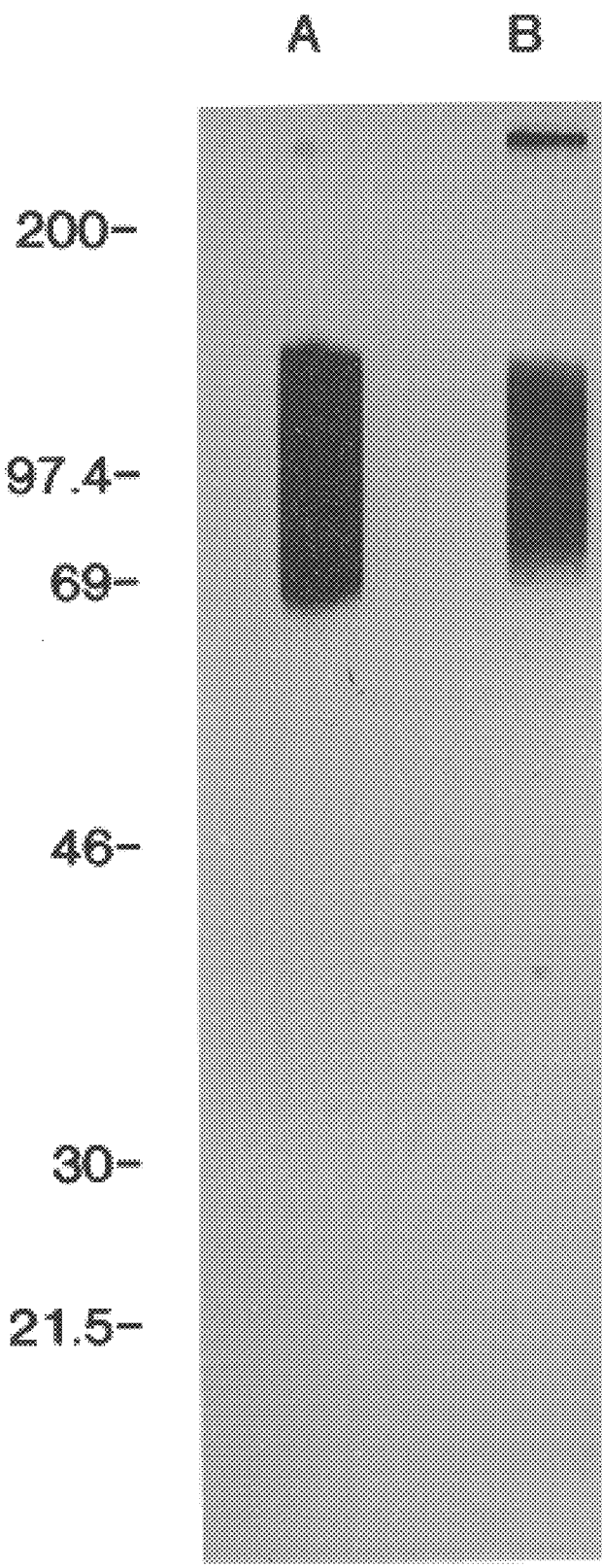
FIG. 11 is a photograph of an SDS-PAGE immunoblot analysis of murine antisera with ZP3 protein labeled with rat monoclonal antibody IE-10 specific for ZP3$_{336-342}$. Authentic ZP3 proteins were separated by SDS-PAGE and blotted onto nitrocellulose, then labeled with rat monoclonal antibody IE-10 specific for ZP3$_{336-342}$ (Lane A) or with sera from mouse #C20 from experiment 2, which was immunized with TMV-ZP331-343 (Lane B), then detected with an alkaline phosphatase conjugated antibody recognizing rat or mouse Ig, respectively. The marks at the left of A indicate the positions of marker proteins of (from top to bottom) 200, 97.4, 69, 46, 30, and 21.5 kDa.

The ability of serum antibodies elicited in immunized mice to recognize the ZP3 protein was evaluated by decorating Western blots of authentic ZP3 separated by SDS-PAGE. FIG. 11 shows immunoblot analysis of murine antisera with ZP3 protein. Serum antibodies from a BALB/CBy mouse (or a C57BL/6J mouse, data not shown) recognized two forms of authentic murine ZP3 glycoprotein which were also recognized by a rat monoclonal antibody (IE-10) specific for $ZP3_{336-342}$ (I. J. East, et al., supra). These results show that an antibody response to both the carrier protein and the added ZP3 epitope is elicited in the serum of mice parenterally immunized with the modified coat protein, although the immune response to the ZP3 antigen differs with mouse genotype. Some of the resulting antibody specifically recognizes the $ZP3_{331-343}$ peptide as revealed by ELISA with this peptide conjugated to KLH. Some circulating antibody also recognizes the zona pellucida in its native context based on Western blot analysis of purified mouse zona pellucida glycoproteins and on in situ recruitment to the zonapellucida. Sera from mice immunized with the hybrid TMV-ZP3 coat protein decorate two ZP3 glycoprotein species on Western blots of mouse zona preparations separated by SDS-PAGE which are identical to those labeled with a rat monoclonal antibody specific for $ZP3_{334-343}$. These studies show that circulating antibodies were recruited to murine zona in vivo as has been demonstrated in mice immunized with ZP3 peptides containing ZP3 residues 336–343 (Millar, et al., supra; Rhim, et al., supra; Lou, et al., supra; Luo, et al., supra). These observations further indicate that the modified coat protein antigen induces serum antibodies which specifically recognize the target auto epitope in its native context, and some of these antibodies are recruited to the antigen in vivo. Despite the relatively low level of $ZP3_{331-343}$ specific antibodies in the sera of some individual immunized mice, antibody was still found to be recruited to zonapellucida in all mice immunized with the modified coat protein.

Previous immunization studies employing $ZP3_{331-343}$ and other closely related ZP3 peptides have resulted in varying levels of contraception depending upon the mouse genotype and the peptide sequence. No impact of immunization with the TMV-ZP3 modified coat protein was observed in this study, but the level of fertility in control mice was relatively low. Our results are potentially different from some previous ZP3 peptide immunization studies (East, et al., supra; Millar, et al., supra) in that we failed to observe a significant impact on fertility after immunization with the ZP3 epitopes despite evidence of a humoral immune response and recruitment of antibody to the zona in vivo.

H. Evaluation of fertility.

After 6 weeks (Experiment 1) or 5 weeks (Experiment 3) of immunization treatment, individual female mice were placed in cages with a male mouse. In experiment 1, male mice were removed after 10 days. Eighteen days after initiation of cohabitation, females were sacrificed and uterine contents were observed. In experiment 3, female mice were moved after one week to cages with a different male mouse for an additional week. Males were removed and females were observed daily for birth of pups. Females were sacrificed 35 days after the removal of males.

Ovarian pathology was associated with immunization and appeared in reduced ovary size, uterine swelling and intra uterine hematoma in some mice. This latter observation may indicate postovulation autoimmune intervention resulting from the TMV-ZP3 immunization. However, the severe oophoritis observed after immunization with peptides containing the T cell epitope $ZP3_{330-336}$ (Rhim, et al., supra; Luo, et al., supra) was not observed in this study for either C57BL/6J or BALB/cBy immunized with the TMV-$ZP3_{331-343}$ antigen. Differences in the antigen composition and in the method of immunization between this study and these previous studies with ZP3 peptides may be responsible in part for the differences in observed responses. The epitope chosen for this study overlaps significantly with $ZP3_{330-336}$, a T cell epitope associated with autoimmune oophoritis (Millar, et al, supra; Rhim, et al., supra; Lou, et al., supra; Luo, et al., supra) and induction of Th-mediated antibody responses to other ZP3 epitopes (Lou, et al., supra; Luo, et al, supra) in {C57BL/6J X A/J}F1 mice. Autoimmune oophoritis as observed for {C57BL/6J X A/J}F1 mice was not anticipated in this study since the critical amino terminal asparagine residue in the $ZP3_{330-336}$ epitope was replaced by a serine residue of the TMV coat protein and the IA molecule ($a^k b^b$) identified for presentation of the $ZP3_{330-336}$ epitope (Rhim, et al., supra) was absent from either of the two genotypes tested here.

Fertility of mice was assessed after male mice were caged with individual immunized and control females for a minimum of 10 days. Following removal of male mice, females were observed for pregnancy and live births (Experiment 3) or fetuses were counted at sacrifice 8 days after removal of males (Experiment 1). As shown by the data summarized in Table 5 below, no reduction in fertility was observed in immunized mice in either experiment 1 or experiment 3, although the fertility of control mice in both experiments was relatively low. At sacrifice in experiment 1, uterine swelling was observed in both nonpregnant treated mice, but not in nonpregnant control mice. This swelling was accompanied by the presence of intrauterine hematomae which were absent from nonpregnant control mice.

TABLE 5

Fecundity of mice immunized with TMV cp or with recombinant TMV cp containing $ZP3_{331-343}$

| mouse | antigen | pups | mouse | antigen | pups |
|---|---|---|---|---|---|
| Experiment #1 C57BL/6J | | | | | |
| 5 | TMV | 0 | 1 | TMV-$ZP3_{331-343}$ | 7 |
| 6 | TMV | 4 | 2 | TMV-$ZP3_{331-343}$ | 0 |
| 7 | TMV | 0 | 3 | TMV-$ZP3_{331-343}$ | 3 |
| 8 | TMV | 7 | 4 | TMV-$ZP3_{331-343}$ | 0 |
| Experiment #3 BALB/cBy | | | | | |
| 1 | TMV | 9 | 21 | TMV-$ZP3_{331-343}$ | 7 |
| 2 | TMV | 0 | 22 | TMV-$ZP3_{331-343}$ | 0 |
| 3 | TMV | 0 | 23 | TMV-$ZP3_{331-343}$ | 0 |
| 4 | TMV | 0 | 24 | TMV-$ZP3_{331-343}$ | 8 |

1. Immunolocalization of antibody.

Ovaries were collected at sacrifice. After removal of associated fatty tissue, each ovary was immersed in OCT (Miles Inc., Elkhart, Ind.), snap frozen and stored at -70° C. until ready for sectioning. Five micron sections were cut on a cryostat, mounted, and air-dried. Sections were fixed for five minutes in acetone, washed in two changes of PBS, and then fixed for ten minutes in periodate-lysine-paraformaldehyde as described (Going, et al., J. Pathology, 155:185, 1988). Sections were washed twice in PBS and then incubated one hour in HRP conjugated anti-murine kappa chain antibody, 0.5 mg/ml Diaminobenzidine (Sigma, Saint Louis, Mo.), (DAB), with 0.1% $H_2O_2$ in PBS for twenty minutes and 0.5% cupric sulfate in 150 mM NaCl for 20 minutes to enhance DAB demonstration. Sections were then counterstained for four minutes in #2 Gill's Hematoxylin (Richard Allan Inc., Richland, Mich.) rinsed in two changes of PBS, dehydrated, cleared and mounted. Negative controls for each specimen received PBS instead of antibody solution, and were otherwise treated identically to other samples.

Figure 13A:
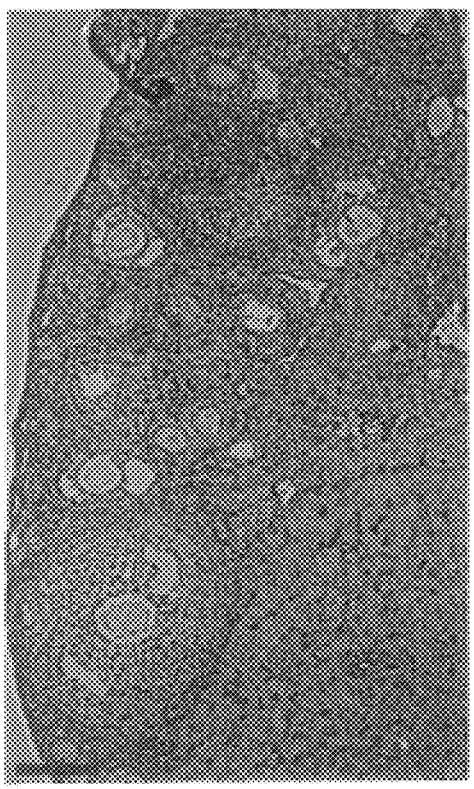
FIG. 13A shows the follicles of mice immunized with TMV CP. Frozen ovaries were sectioned (7 mm) and labeled with goat anti-mouse kappa chain-horseradish peroxidase conjugate, then developed with DAB to identify tissues containing mouse kappa chain immunoglobulin.
Figure 13C:
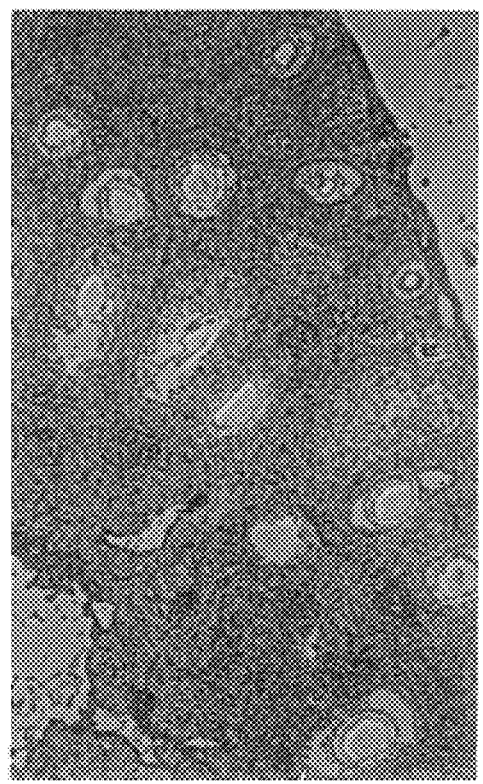
FIG. 13C shows the follicles of mice immunized with TMV-ZP3$_{331-343}$.
Figure 13B:
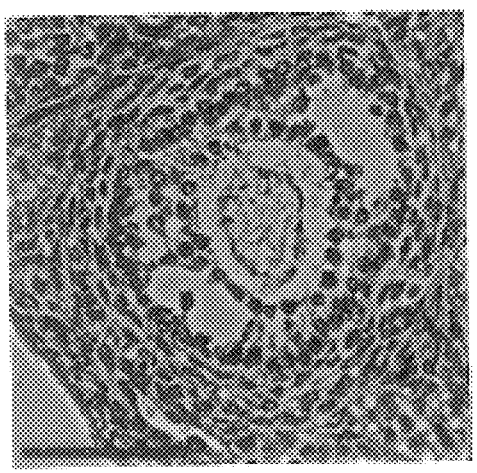
FIG. 13B shows the subject matter of FIG. 13A at 200×magnification.
Figure 13D:
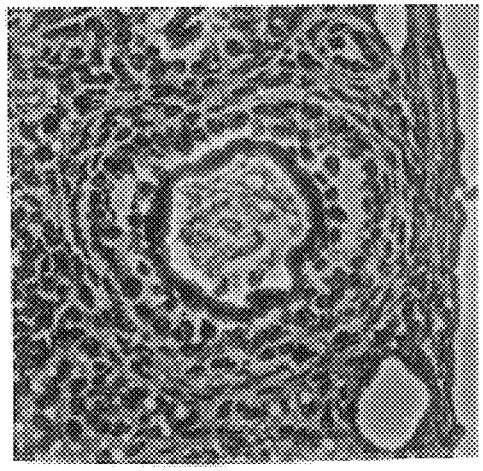
FIG. 13D shows the subject matter of FIG. 13A at 400×magnification.

Cryosections of ovaries were labeled with a horseradish peroxidase conjugate of a goat antibody specific for murine kappa chains. DAB staining superimposed on zona pellucida of treated mice, but not on zona of untreated controls, revealing the presence of significant quantities of murine antibody recruited in situ to the zona pellucida of immunized mice. Frozen ovaries were sectioned (7 μm) and decorated with goat anti-mouse kappa chain-horseradish peroxidase conjugate, then developed with DAB to identify tissues containing mouse kappa chain immunoglobulin. This localization is illustrated in the micrographs in FIG. 13. Frozen ovaries were sectioned (7 μm) and labeled with goat anti-mouse kappa chain-horseradish peroxidase conjugate, then developed with DAB to identify tissues containing mouse kappa chain immunoglobulin FIGS. 13A and 13B show follicles of mice immunized with TMV CP. FIGS. 13C and 13D show follicles of mice immunized with TMV-$ZP_{331-343}$. Isotype evaluation of the antibody localized to zona pellucida of immunized mice demonstrated this antibody was predominantly IgG and not IgM or IgA(data not shown). In general, higher levels of background staining with DAB in ovary sections of treated mice were observed. At sacrifice ovary size was observed to be smaller in treated mice than in controls.

EXAMPLE 13 cAB promoters drive the nuclear expression of chlorophyll A/B binding protein genes (Apel and Kloppstech, Eur.

J Biochem., 85:581–588, 1978). The expression is light inducible, phytochrome mediated, and limited to green tissue (Mitra, et al., Plant. Mol. Biol., 12:169–179, 1989; Simpson, et al., Nature, 323:551–554, 1986; Teeri, et al, EMBO J., 8343–350, 1989). Tobacco (N. tabacum) leaf discs were transformed with the MP gene under the control of the cAB promoter AB80, and more than 10 transgenic lines each of N. tabacum cv Xanthi nn (a systemic host for TMV) and cv Xanthi NN (hypersensitive to TMV) were recovered. Also Xanthi nn was transformed with MP gene or the uidA gene under the control of the pal2 promoter, and 6 pal2-MP lines and 5 pal2-uidA lines were recovered. In addition, transgenic plants as described in Table 5 of this application that express the MP gene or the uidA gene under the control of the cAB or the CaMV 35S promoter were used. Tobacco transformed with the cAB promoter with no MP coding sequence was used as a negative control.

sequence of TMV isolated from pTM-934 (comprising TMV nucleotides 4855–5868; Oliver, et al., Virology, 155:277–288, 1986) ligated with the nos 3' end. A fragment containing the pal2 promoter, the TMV MP sequence, and the nos termination sequence was isolated by partial digestion with Hind III and complete digestion with EcoR I. The isolated gene was ligated with the binary plant transformation vector pMON-505 (Rogers, el al., Methods Enzymol., 153:253–277, 1987) that had been previously digested with EcoR I and Hind III. The plasmid pPGN was constructed by first ligating the E. coli uidA gene, derived from the plasmid pRAJ-260 (Jefferson, et al., Proc. Natl. Acad. Sci. USA, 88:2702–2706, 1986), with the nos termination signal in pUC 19. The pal2 promoter (described above) was ligated into the Sma I site of this plasmid resulting in the plasmid pUC19-PGN. This gene was excised as an Eco RI/Hind III fragment and ligated with pMON-505 to give pMON-505-

TABLE 6

DESCRIPTION OF THE TRANSGENIC PLANT LINES USED

| Plant Line | Tobacco Cultivar | Promoter | Coding Sequence | Descriptive Name Used in Text |
|---|---|---|---|---|
| Sx-O | Xanthi nn | cAB | none | control |
| Esc4-7 | Xanthi nn | cAB | uidA | nn-cAB-uidA |
| cAB-nn E, F, I, 6 | Xanthi nn | cAB | TMV MP | nn-cAB-MP |
| cAB-NN F, J, O, 4 | Xanthi NN | cAB | TMV MP | NN-cAB-MP |
| G 6-1 | Xanthi NN | CaMV 35 S | uidA | NN-35S-uidA |
| 277 | Xanthi nn | CaMV 35 S | TMV MP | nn-35S-MP |
| 2004, 2005 | Xanthi NN | CaMV 35 S | TMV MP | NN-35S-MP |
| PGN | Xanthi nn | pal2 | uidA | nn-pal2-uidA |
| PMN | Xanthi nn | pal2 | TMV MP | nn-pal2-MP |

A. Plasmid construction and tobacco transformation.

1. Plasmids containing the cAB promoter.

A DNA fragment corresponding to nucleotides 4903–5709 of TMV $U_1$ was inserted into the Xho I and BamH I sites of pUC 18. This fragment was excised and ligated into the Sal I and BamH I sites of the plasmid pGV1511 (construction of pGV1511 is described in Cashmore, Proc. Natl. Acad. Sci. USA, 81:2960–2964, 1984, which is incorporated herein by reference in its entirety) downstream of the cAB promoter AB80 from Pisum sativum to form the plasmid pGV1511-30K. The resulting construct is referred to herein as the cAB-MP gene construct.

Triparental mating (Matzke and Matzke, Plant Mol. Biol., 7:357–365, 1986) was used to mobilize pGV1511-30K into the rifampicin-resistant C58C1 strain of Agrobacteriurn tumefaciens (Van Larebeke, et al., Nature, 252:169–170, 1974) carrying the disarmed Ti plasmid pGV3850 (Zambryski, et al., Science, 246:377–379, 1983). The resulting chimeric construct was used to transform Nicotine tabacum cv "Xanthi NN" and "Xanthi nn" by the leaf disc procedure (Horsch, et al., Science, 227:1229–1231, 1985). N. tabacum cv Xanthi nn was also transformed with a chimeric construct made from pGV1511 (without the transformed with a MP gene sequence) to produce control plants. $R_1$ plants were used for all experiments. Plants were grown at 25–30° C. under artificial light with a 14 hr light/10 hr dark photoperiod.

2. Plasmids containing the pal2 promoter.

The pal2 promoter was derived from the gPAL 2 gene of Phaseolus vulgaris (Cramer, et al., Plant Mol. Biol., 12:367–383, 1989). A Dra I fragment containing a 1157 bp fragment was ligated into the Xho I site (made blunt by a fill-in reaction) of pUC18-MN, which contains the MP PGN. Transformation of tobacco was carried out as described by Reimann-Philipp and Beachy (Mol. Plant-Microbe Interact., 6:323–330, 1993). $R_1$ plants were used for all experiments. Plants were grown as described above.

B. Other plant lines.

$R_3$ progeny of plant lines 277, 2004 and 2005 (Deom, et al., Science, 273:384–389, 1987; Deom, et al., Virology, 180:251–256, 1991) were used. These lines express the MP open reading frame under the control of the 35S promoter of cauliflower mosaic virus (referred to herein as the 35S-MP gene construct). Plants were grown from $R_1$ seeds of G 6-I, a transgenic plant line that expresses the uidA gene from the 35S promoter, and which was previously developed in this laboratory (L. Farrell and R. N. Beachy, unpublished). $R_1$ seeds of line Esc4-7, which contains a cAB-uidA gene construct, were kindly provided by June Simpson, CINVESTAV, Irapuato, Mexico. Plants were grown as described above. Heterozygous R1 progeny plants that contained the MP gene were used in the virus infection studies.

C. In vitro transcription and plant inoculation.

Full-length clones of TMV $U_1$ and TMVΔMP (Holt and Beachy, 1991, supra) and TMVΔMP-GUS (Lapidate, et al., The Plant J, 4:959–970, 1993), were transcribed in vitro, and the transcripts were inoculated onto plants using the procedure of Holt and Beachy, supra (1991). TMVΔMP lacks the first two-thirds of the MP sequence, and retains the last third, which contains the viral origin of assembly and the coat protein subgenomic promoter, in an untranslated form. TMVΔMP-GUS contains the uidA coding sequence in place of the first two-thirds of the MP gene, reining the last third of the gene as in TMVΔMP. In all plants, gene integration was confirmed by Southern blot analysis (data not shown), and in the case of plants expressing the MP gene, MP accumulation was confirmed by Western blot analysis (not shown).

D. Histochemical detection of GUS activity.

Leaf tissue from transgenic plants that express the uidA gene or from plants infected with TMVΔMP-GUS was vacuum infiltrated with GUS assay buffer (50 mM sodium phosphate buffer, pH 7.0, 10 mM EDTA, 0.1% Triton X-100, 0.5 mM potassium ferrocyanide/ferricyanide) (Jefferson, el al., Proc. Natl. Acad. Sci. USA, 88:2702–2706, 1986) containing 0.5 mg/ml 5-bromo-4-chloro-3-indolyl-β-D-glucuronide cycloammonium salt (X-Gluc). Tissues were incubated overnight at 37° C. and then transferred to 70% EtOH for clearing and examination.

Figures 14A, 14B, 14C:
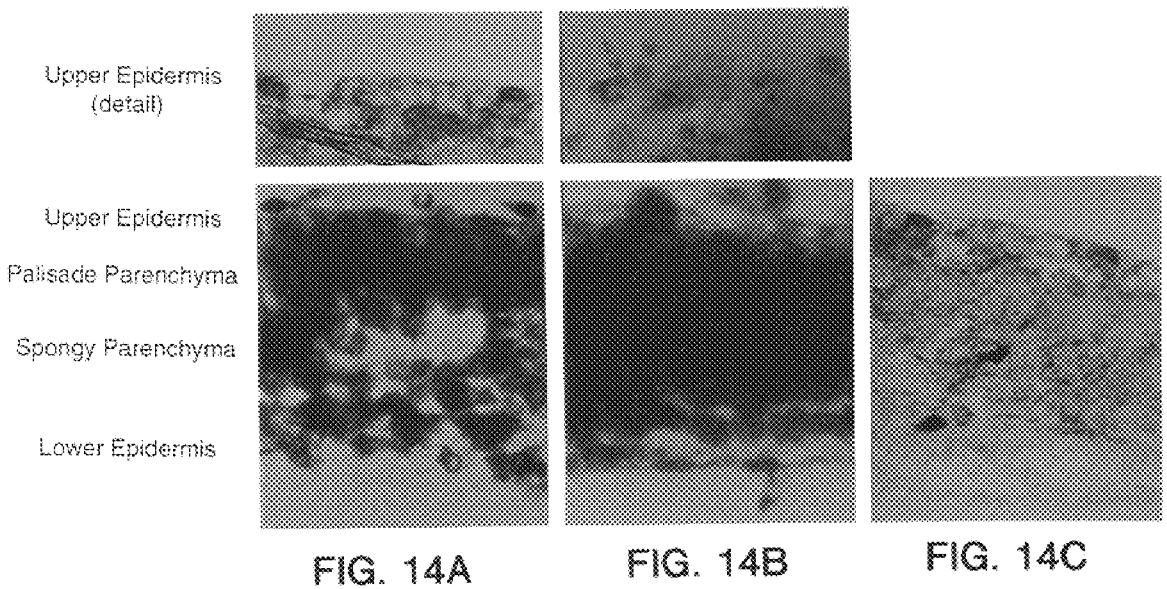
FIGS. 14A–14C are the pattern of GUS activity in leaves of tobacco plants inoculated with transgenic clones of TMV. Upper photographs in FIGS. 14A and 14B show GUS activity in isolated epidermis. The lower photographs show transverse sections through leaf tissues.

In order to determine in which tissues expression in transgenic N. tabacum plants occurs, plants expressing the uidA gene from the cAB, 35S, or pal2 promoter were analyzed by histological GUS assays. FIG. 14 shows leaf sections of R1 progeny of transgenic plants after incubation with the substrate X-Gluc. As has been previously demonstrated by others (Jefferson, Genet. Eng. 10:247–263, 1988), the results shown in FIG. 14A indicate plants that expressed the 35S-uidA gene construct showed high levels of GUS activity in all tissues. In contrast, as shown in FIG. 14B, plants that express the cAB-uidA gene construct showed no activity in epidermal cells (except for guard cells and leaf hairs), low activity in vascular cells (not shown), and high activity in mesophyll cells, guard cells, and leaf hair cells. It is assumed that plants expressing the MP gene follow the same pattern of gene expression. In accordance with previously reported results (Reimann-Philipp and Beachy, Mol. Plant-Microbe Interact, 6:323–330, 1993), as shown in FIG. 14C, plants expressing the pal2-uidA gene construct showed GUS activity primarily in the leaf upper epidermis.

E. Detection and quantification of MP.

Fresh leaf tissue (excluding the midribs) from transgenic plants or plants infected with TMV was homogenized in extraction buffer (62.5 mM Tris-HCl, pH 6.8, 1% [w/v] SDS and 20% [v/v] glycerol) followed by heating for 5 minutes in a boiling water bath. Proteins were precipitated by addition of 4 volumes of ice-cold 14,000 g for 5 minutes, and the pellet was redissolved in extraction buffer. Total protein concentration was determined using the BCA assay (Pierce, Rockford, Ill.). MP was detected by SDS-PAGE (Laemmli, supra) followed by Western blotting (Sambrook, et al., supra; Towbin, et al., Proc. Natl. Acad. Sci. USA, 76:4350–4354, 1979) using an anti-MP antibody (Deom, et al., 1987, supra) as the primary antibody, and an alkaline phosphatase conjugate (Southern Biotechnology Associates) as the secondary antibody. MP was quantified by ELISA in microtiter plates using the same antibodies.

Figure 15:
FIG. 15 is a representation of a Western blot PAGE analysis of tissues from Sx-0 (control) and nn-pal2-MP plants. ue upper epidermis; wl=whole leaf; s=stem.

Plants expressing the pal2-MP gene construct were also analyzed by PAGE followed by Western blotting. Total protein was extracted from leaf upper epidermis, whole leaf tissue, and stem tissue. FIG. 15, which compares Western blots of Sx-0 (control) and nn-pal2-MP plants, indicates MP accumulation was found to occur predominantly in the leaf upper epidermis.

Figure 16A:
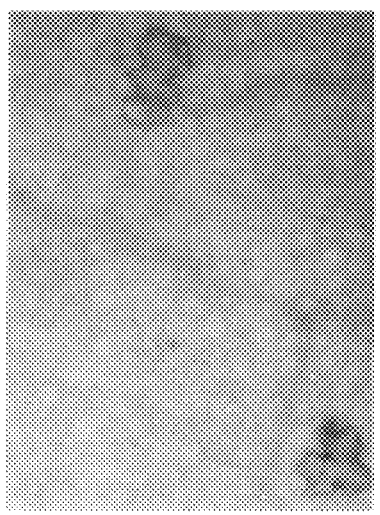
Figure 16B:

Histochemical detection of GUS activity following inoculation with TMVΔMP-GUS showed that in both the SN-cAB-MP and N19-35S-MP plant lines, virus replication (as revealed by GUS activity) is restricted to the vicinity of local lesions. Characteristic results of GUS activity detection for lines cAB-NN F and 2005 infected with TMVΔMP-GUS are shown in FIGS. 16A and 16B, respectively. In both nn-cAB-MP and nn-35S-MP plants inoculated with TMVΔMP-GUS, GUS activity was found in large irregularly shaped areas (not shown).

F. Tissue specificity of the cAB and pal2 promoters.

The amount of MP that accumulates in each cAB-MP and 35S-MP transgenic plant line was determined and compared to the amount produced by TMV infection in nontransgenic plants at five days after inoculation. Three week old plants were inoculated on each of 2 lower leaves with 50 μl of TMVΔMP at a concentration that would form 150 lesions on a 2005 leaf. MP was extracted as described above from leaves 3 and 4 (from the top) of plants 6 weeks after planting and was quantitated by ELISA.

Table 7 of this application displays the results for Xanthi nn plants, and Table 8 of this application displays the results for Xanthi NN plants. TMV infection produced the highest level of MP, and was assigned the value of 100% for comparative purposes. The various transgenic lines showed a wide range of MP levels, from as little as about 1% to as much as about 60% of the level seen in TMV-infected plants.

TABLE 7

SEVERITY OF SYMPTOMS AND AMOUNT OF VIRUS DETECTED IN UPPER
LEAVES OF TRANSGENIC XANTHI nn TOBACCO PLANTS INOCULATED WITH TMV ΔMP

| Plant Line | Relative Amount of MP (%)[a] | Symptoms[b] | Relative CP Level in in Upper Leaves (%) | Number of Infectious Units in Upper Leaves[c] |
|---|---|---|---|---|
| Sx-0 | 0 | None | 0 | 0 |
| Nontransgenic Xanthi nn infected with TMV | 100 | Severe mosaic in upper and middle leaves, rugosity in middle leaves | 100 | 186 ± 35 |
| 277 | 61 | Severe mosaic in upper leaves, rugosity and chlorosis in middle leaves | 100 | 182 ± 31 |
| cAB-nn E | 4.2 | Mosaic in upper leaves and rugosity in middle leaves | 88 | 144 ± 26 |
| cAB-nn F | 3.8 | Attentuated mosaic in upper leaves | 84 | 112 ± 21 |
| cAB-nn I | 2.4 | Rugosity in upper leaves, chlorosis in middle leaves | 66 | 68 ± 11 |
| cAB-nn 6 | 1.3 | None | 12 | 11 ± 4 |

[a]The values are averages of 3 punches taken from leaves 3 and 4 from each of 3 plants. The percentages are relative to the amount of MP in extracts of Xanthi nn tobacco plants infected with TMV (25 μg MP per g of frozen leaf tissue), 5 days after inoculaton.
[b]Three-week-old plants were inoculated with 50 μl of TMV ΔMP (at a concentration that would form 150 lesions on a 2005 leaf) on each of 2 lower leaves. The symptoms were recorded in 4 plants 10 days after inoculation.
[c]Two leaf discs 5.9 mm in diameter (0.4 g) were collected from each plant and ground in 400 μl of phosphae buffer pH 7.2 50 μl of each extract was inoculated onto a leaf of plant line 2005 and local lesions were counted. Results are the averages of 6 leaves of three 2005 plants, 4 days after inoculation.

TABLE 8

NUMBER AND SIZE OF LOCAL LESIONS IN TRANSGENIC NN TOBACCO PLANTS INOCULATED WITH TMV OR TMV ΔMP

| Plant Line | Relative Amount of MP (%)[a] | TMV[c] | | TMV ΔMP[c] | |
|---|---|---|---|---|---|
| | | Number | Diameter (mm) | Number | Diameter (mm) |
| Xanthi NN | 0 | 24.0 ± 16 | 3 | 0 | N/A |
| Nontransgenic Xanthi nn infected with TMV | 100 | N/A[d] | N/A | N/A | N/A |
| 2005 | 58 | 32.0 ± 18 | 6.0 ± 2.4 | 35.1 ± 17 | 4.0 ± 1.8 |
| cAB-NN F | 33 | 21.1 ± 19 | 3.6 ± 1.4 | 48.8 ± 23 | 1.8 ± 1.5 |
| cAB-NN J | 27 | 30.2 ± 14 | 3.4 ± 1.6 | 58.7 ± 32 | 1.5 ± 1.4 |
| 2004 | 20[b] | 27.6 ± 13 | 3.5 ± 1.1 | 18.5 ± 10 | 1.4 ± 0.4 |
| cAB-NN O | 2.3 | 28.3 ± 21 | 3.5 ± 1.4 | 0.3 ± 0.8 | 1.1 ± 0.5 |
| cAB-NN 4 | 1.6 | 26.6 ± 17 | 3.4 ± 1.2 | 4.2 ± 1.8 | 1.2 ± 0.8 |

[a]See Table 2 for explanation of values.
[b]Determined from values described by Deom, et al. (Virology, 180:251–256, 1991).
[c]Plants were inoculated with 50 μl per leaf of a standard virion inoculum (TMV or TMV ΔMP) solution that would produce approximately 50 local lesions on a 2005 leaf. The number and size of local lesions are the average of 2 inoculated leaves on each of 3 plants 4 DPI.
[d]N/A = not applicable.

F. Quantification of TMV CP in plants.

Two 5.9 mm-diameter leaf disks were ground in 100 μl of 35 mM potassium phosphate, pH 7.5, 10 mM β-mercaptoethanol, 400 mM NaCl. Insoluble material was removed by a 5 minute centrifugation at 14,000 g. 10 μg of protein (as determined by BCA assay) was used in an ELISA reaction in microtiter plates using an anti-CP antibody as the primary antibody, and an alkaline phosphatase conjugate as the secondary antibody.

Complementation of TMV mutants by transgenic plants

Figure 16C:
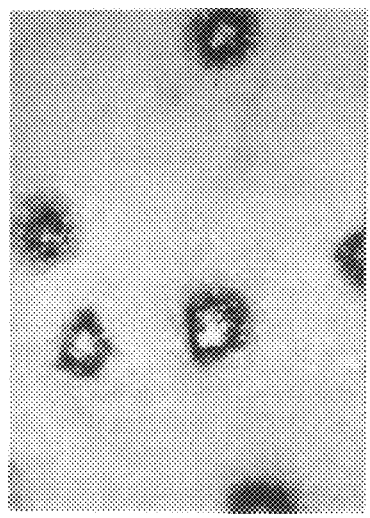

Plants were inoculated with RNA transcripts produced in vitro from cDNA clones of TMV lacking the MP gene (TMVΔMP; Holt and Beachy, 1991, supra) or in which the MP gene is replaced by the uidA gene (TMVΔMP-GUS; Lapidot, et al., *The Plant J.*, 4:959–970, 1993). All of the plant lines that express the MP gene from the cAB or 35S promoter were able to complement both TMV mutants regardless of the level of MP accumulation, although the severity of symptoms caused by infection was dependent upon the MP level (Tables 7 and 8). When nn-pal2-MP plants, which accumulate MP primarily in the epidermis, were inoculated with TMVΔMP, GUS activity in plants three days after inoculation indicated no symptoms of virus infection. Additionally, twenty-four plants were inoculated with RNA transcripts of TMVΔMP-GUS. As shown in FIG. 16C, GUS activity three days after inoculation was found only in isolated epidermal cells. No sign of virus replication was found in mesophyll cells.

The visual appearance of the local lesions produced by TMVΔMP in plant lines that express the MP sequence from the cAB promoter (e.g., line cAB-N21 F; FIG. 16D) is different from that produced in plants that harbor the 3f S-MP gene construct (e.g., line 2005; FIG. 16E). The lesions produced on 2005 plants are similar in appearance to those produced by TMV in Xanthi NN plants, i.e., the lesions have a tan central area surrounded by a ring of dark pigment. By contrast, the lesions produced in cAB-NN F plants are white and do not have a dark ring, and are also significantly smaller in size (see below). This unusual morphology was seen in all the NN-cAB-MP lines when infected with TMVΔMP, regardless of the amount of MP produced. Infection of these plant lines with wild type TMV produced normal local lesions; two examples are shown in FIGS. 16F and 16G.

Effect of MP level on severity of symptoms and level of virus accumulation

Three-week-old transgenic Xanthi nn plants carrying the cAB-MP gene construct that accumulated widely varying levels of MP were inoculated with equal amounts (50 μl) of TMVΔMP at a concentration that would form 150 lesions on a 2005 leaf) on each of two lower leaves. Ten days after inoculation, disease symptoms were recorded in four plants of each line, and the level of virus accumulation in upper leaves was determined by quantitating CP accumulation and by inoculating leaf homogenates onto plant line 2005. Two leaf discs 5.9 mm in diameter (0.4 g) were collected from each plant and ground in 400 μl of phosphate buffer pH 7.2 50 μl of each extract was inoculated onto a leaf of plant line 2005 and local lesions were counted The number of infectious units found, as shown in Table 7, are the average of 6 leaves of three 2005 plants, 4 days after inoculation. The level of virus accumulation and the severity of symptoms in line 277 (nn-35S-MP) infected with TMVΔMP matched that of nontransgenic Xanthi nn infected with TMV, even though the level of MP was only 60% as great as the level produced by TMV infection. Lines cAB-nn E and cAB-nn F, with much lower levels of MP (about 4% of TMV infection), showed strong disease symptoms and significant amounts of virus accumulation in upper leaves. Lines cAB-nn I and cAB-nn 6, with even lower amounts of MP, showed moderate or no symptoms and significantly lower levels of virus accumulation. Thus, the severity of disease symptoms and the level of virus accumulation in these plant lines was correlated with the amount of MP in the plants. However, a small amount of MP (about 4% of the level found in TMV infection) is sufficient to produce essentially full development of symptoms and virus accumulation.

Effect of MP level on number and size of local lesions

Transgenic Xanthi NN plants carrying the cAB-MP and the 35S-M P gene constructs were inoculated with TMV or TMVΔMP. The number and size of the resulting local lesions were determined as described above are shown in the data summarized in Table 8 and in FIGS. 16F and 16G). The number of local lesions produced by TMV was similar in all plant lines tested. In contrast, the number of lesions produced by TMVΔMP depended on the level of MP in the plants. On lines cAB-NIK O and cAB-NN 4, which have very low levels of MP (about 2% of the level seen in TMV-infected Xanthi nn plants), very few lesions were produced. On line 2004, with 20% as much MP as in systemic TMV infection, the number of lesions was higher, and in the three lines with 27% or more of the MP level seen in systemic TMV infection, the number of lesions reached a maximum level.

The size of the lesions produced by TMVΔMP did not depend on the level of MP in the plant or on the promoter that was driving MP expression, except on line 2005. Likewise, the size of lesions produced by TMV, while larger than TMVΔMP lesions, was invariant regardless of the level of MP produced by the plant (including nontransgenic plants), except on line 2005. The anomalous size of lesions on line 2005 may be due to the exceptionally high level of MP in this line.

Figure 17A:
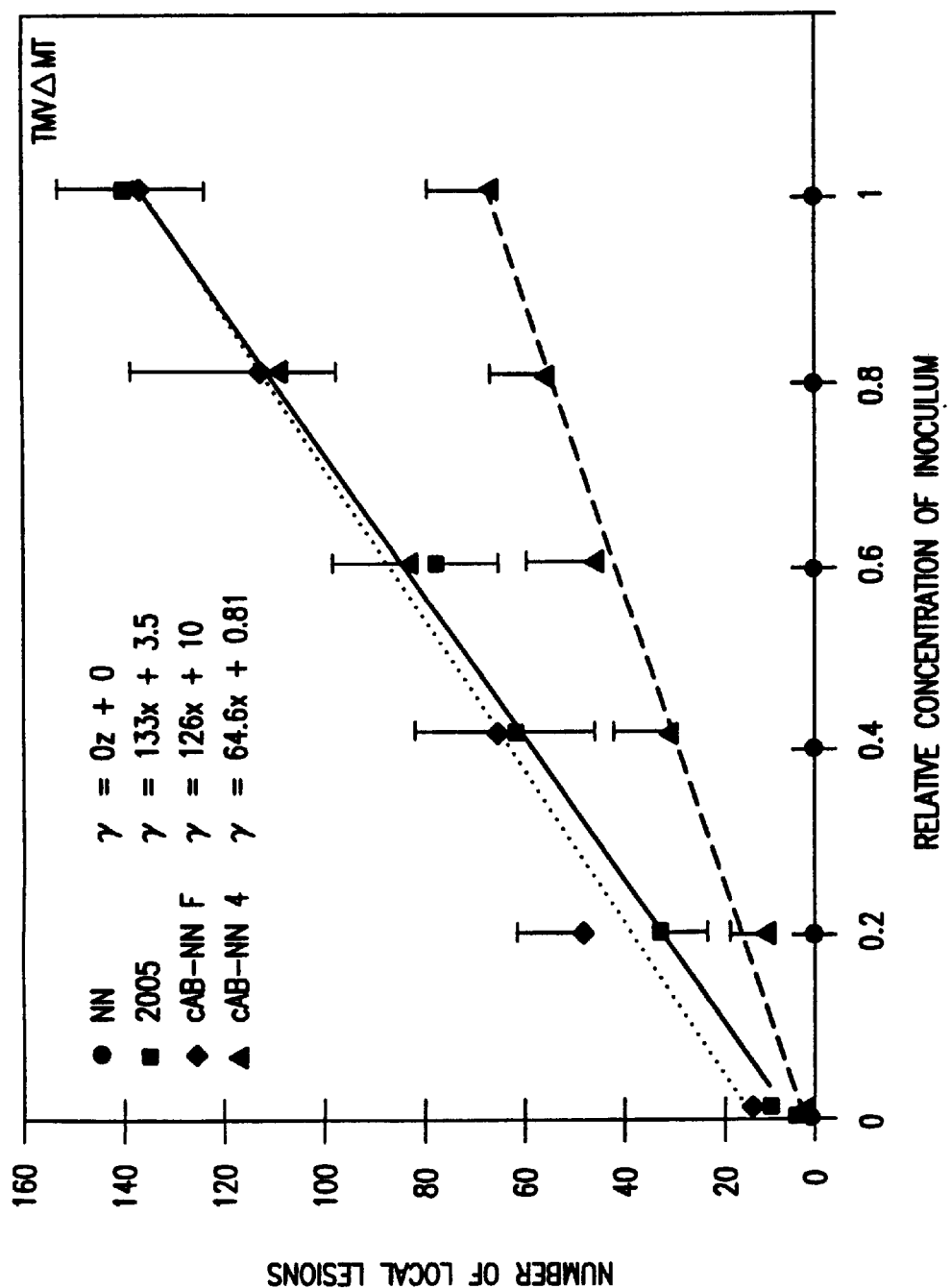
FIGS. 17A–17B are a set of graphs comparing the number of local lesions produced on tobacco cv. Xanthi NN plants by different concentrations of transgenic clones of TMV clones.
Figure 17B:
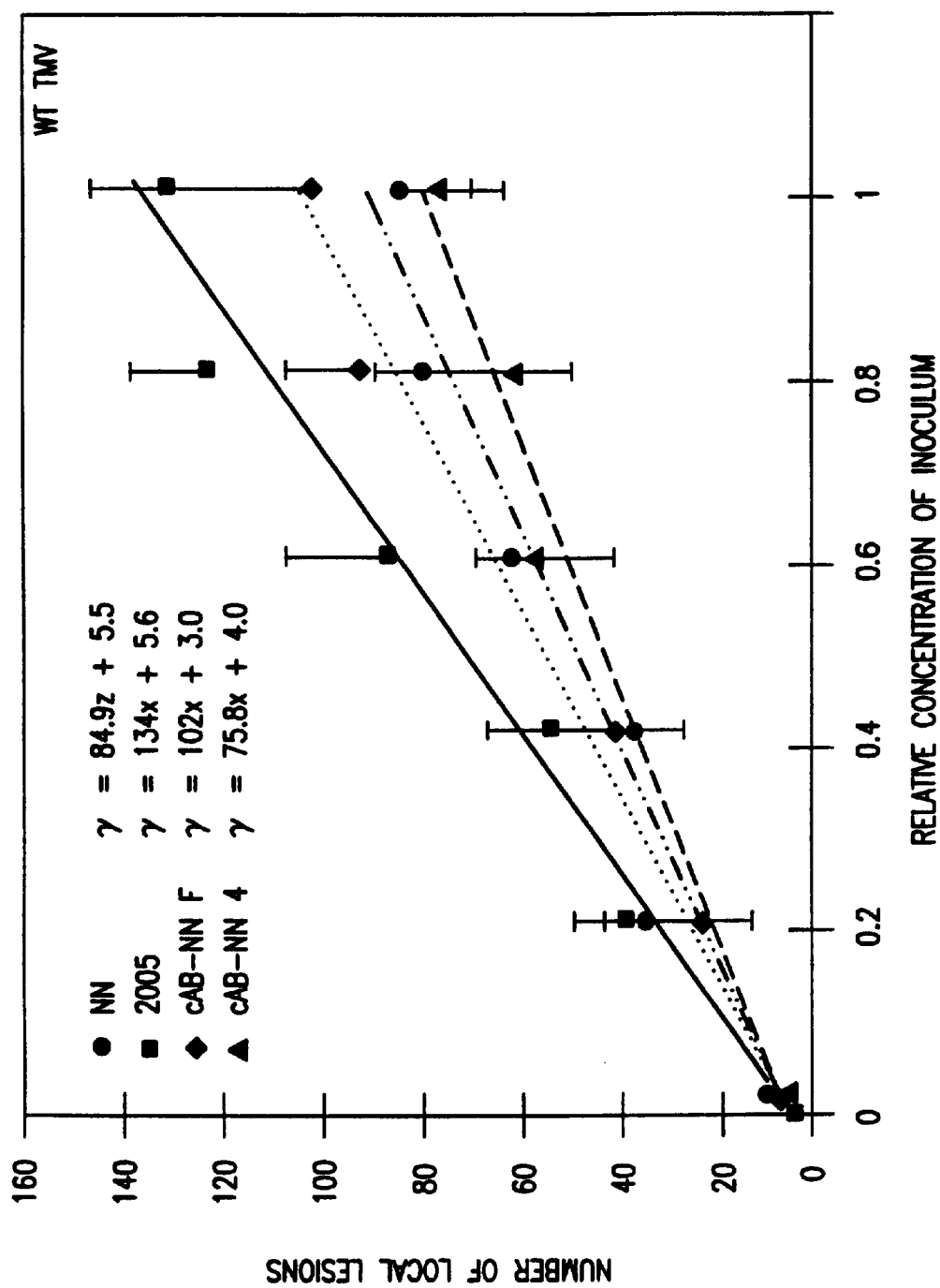

To better characterize the effect of MP level on the number of lesions formed, several lines were inoculated with a range of concentrations of TMVΔMP or TMV. As shown by the data in FIG. 17, the number of local lesions produced varied linearly with the inoculum concentration. At higher virus concentrations, the differences between the lines become more apparent than in the data summarized in Table 8. With TMVΔMP, the slopes of the dose/response lines for cAB-NN F and 2005, which contain high levels of MP, were approximately equal, and were significantly greater than for cAB-NN 4, which contains a very low level of MP, showing that the level of MP affects the likelihood of a multicellular infection being established. With TMV, the slopes of the dose/response lines for cAB-NN F and cAB-NIK 4 were roughly equal to the slope for nontransgenic plants. The slope for plant line 2005 was greater than for the other three plant lines. In the case of TMVΔMP, 33% of the level of MP found in nontransgenic plants systemically infected with TMV is sufficient to produce the maximum number of lesions. In the case of TMV, the level of MP in the plant does not affect the number of lesions except in line 2005, with the highest MP level. In both cases, the fact that all the dose/response lines intercept the y-axis at 0 suggests that the number of potential infection sites on a leaf is the same for all the plant lines.

Transgenic plants that contain the cAB-MP gene construct were able to complement two mutants of TMV that lack a functional MP gene, TMVΔMP and TMVΔMP-GUS. This demonstrates that TMV infection does not require MP expression in most epidermal cells. Thus, expression of MP in the epidermis may not be needed for the virus to move from an epidermal cell to a mesophyll cell. This can be explained if: (a) virus can move from epidermal cells to mesophyll cells without the aid of MP; (b) the plasmodesmata connecting epidermal cells to mesophyll cells can be modified sufficiently by MP produced solely in mesophyll cells as to allow virus movement; or (c) MP can move from mesophyll cells into epidermal cells, where it might interact with and promote movement of the virus; Waigmann, et al. (*Proc. Natl. Acad. Sci USA,* 91:1433–1437, 1994) have shown that MP purified from *E. coli* and injected into tobacco leaf cells can move into adjacent cells. In a TMV infection of a nontransgenic plant, only option (a) is available.

Inoculation of nn-pal2-MP plants with TMVΔMP-GUS resulted only in infection of individual epidermal cells (FIG. 16C). The presence of MP in epidermal cells was not sufficient to allow virus to spread laterally through the epidermis or downward into the mesophyll cells (and, for that matter, that virus cannot spread in either of these ways without the aid of MP). In a TMV infection of a nontransgenic plant, the virus may produce a very high level of MP during the initial stages of infection, in which case the inability of nn-pal2-MP plants to complement TMVΔMP may simply be due to an insufficient amount of MP in the epidermis. However, analysis by Western blotting (FIG. 15) shows a substantial level of MP accumulation in the leaf upper epidermis. Another explanation is that virus movement from the epidermis to the mesophyll may have occurred too infrequently to be detected in these experiments. This raises the possibility that TMV infection of mesophyll cells in a nontransgenic plant may not always depend on the presence of MP in the epidermis. Further studies are needed to determine how TMV infection progresses to the multicellular stage.

The lesions formed by TMVΔMP on NN-cAB-MP plants do not show the dark ring around the perimeter that is seen in lesions produced by TMVΔMP on NI9-35S-MP plants and by TMV on nontransgenic plants (FIGS. 16D–G). This difference may be due to the absence of MP in most epidermal cells in NN-cAB-M P plants, which could affect how the hypersensitive response occurs. The difference is not the result of a low level of MP, since line 2004 (NN-35S-MP), with a level of MP comparable to that of cAB-NN J, shows small lesions with normal morphology. Other factors can also affect lesion morphology: some TMV mutants (in most cases known to contain mutations in the MP gene) form lesions without rings (Jockusch, *Virology,* 35:94–101, 1968; Zimmern and Hunter, *EMBO J.,* 2:1893–1990, 1983; T. W. Kahn and R. N. Beachy, unpublished results).

The availability of transgenic plants with varying levels of MP allowed us to study the role of MP level in the initiation, local spread, and systemic spread of virus infection. The effect of the amount of MP on the establishment of multicellular infection sites was determined by counting the number of local lesions formed on Xanthi NN plants. The effect of the amount of MP on local spread was determined by measuring the diameters of local lesions at a given time after inoculation, which is taken to be indicative of the rate at which the virus spreads locally. The effect of MP level on systemic spread of virus was determined by measuring the level of virus accumulation in upper leaves of plants at a given time after inoculation of lower leaves. The rate of systemic spread will be a function of the efficiency with which infection is established and the rates of local and long-distance movement.

When transgenic Xanthi NN plants were inoculated with TMVΔMP, the number of local lesions produced reached a maximum level when the amount of MP in the plants was about 30% of the MP level in systemic TMV infection of nontransgenic Xanthi nn plants (Table 8; FIG. 17). When the same plant lines were infected with TMV, the number of lesions produced did not depend on the level of MP produced by the plant, except perhaps in the line (2005) that produced the highest level of MP. When the plants were infected with varying concentrations of TMV or TMVΔMP, the slopes of the dose/response lines always intercepted the y-axis at 0, showing that a low level of MP does not reduce the number of potential infection sites on a leaf, but only reduces the likelihood that a given site will progress to a multicellular infection. These results show that a relatively low level of MP is required for TMV to establish a multicellular infection. Above the level of MP seen in line cAB-NN J, an increase in the amount of MP does not enhance the efficiency of the establishment of infection. A possible explanation for this observation is that the level of MP in each cell in a transgenic leaf may vary. At low total levels of MP, some cells may have less MP than is required to allow an infection to spread, while others may exceed the threshold level. As the total amount of MP is increased, a point will be reached at which all cells are above the threshold; further increases in the MP level will not lead to a greater efficiency of establishing a multicellular infection.

As shown by the data in Table 8, once a multicellular infection is established, the rate at which the virus spreads locally can be assessed by measuring the rate of growth of local lesions. In TMVΔMP infections, the size of local lesions after a given amount of time was the same regardless of the amount of MP in the plant line, except in the case of line 2005, which contains the highest amount of MP. In TMV infection, the lesions were larger than in TMVΔMP infection, and were comparable in size to lesions formed by TMV on nontransgenic plants. Again, the exception was line 2005, on which lesions were larger. The level of MP in line 2005 is apparently so high that the virus is able to overcome the hypersensitive response to some extent by spreading quickly (lesions on this line continue to grow for a longer time than lesions on other plant lines). At lower levels of MP, the amount of MP contributed by the plant does not influence the rate of spread of the virus, although TMV apparently has an advantage over TMVΔMP. The more rapid spread of TMV may be the result of production of locally high levels of MP during virus replication.

When transgenic Xanthi nn plants were infected with a high concentration of TMVΔMP, the severity of systemic disease symptoms and the level of virus accumulation in upper leaves depended on the level of MP in the plants (Table 7). However, above a rather low level of MP (about 4% of the level seen in TMV infection of nontransgenic plants), an increase in the amount of MP did not lead to an increase in virus accumulation. Although this may suggest that a process or function that is involved in systemic infection has been saturated by even a low level of MP. The most likely explanation is that the upper leaves have reached the point at which no more virus can be produced. This shows that TMV produces substantially more MP than is required to achieve full systemic infection of a tobacco plant.

The question of how the level of MP influences the rate of systemic infection can be addressed by comparing the results of the systemic infection experiments (Table 7) to the results of the experiments that measured the efficiency of initiation of establishment of multicellular infection and the rate of local spread (Table 8). Maximal efficiency of establishment of multicellular infection requires about 30% of the level of MP seen in systemic TMV infection of Xanthi nn plants, while maximal rate of systemic spread requires only about 4% of that level. Thus, under the experimental conditions reported here, the rate of systemic spread does not appear to be limited by the efficiency of establishment of infection. The rate of local spread is independent of the level of MP (Table 8), suggesting that the rate of systemic spread is not limited by the rate of local spread (although the rate of local spread in Xanthi NN and nn plants could be different). Thus, the level of MP may exert its influence on the rate of systemic infection by directly affecting the rate of long-distance spread of virus through the vascular system of the plant.

In summary, the establishment of a multicellular infection by TMV does not depend on the presence of MP in the majority of epidermal cells, and indeed, appears not to benefit from its presence. This step does however require a moderate level of MP in the mesophyll in order to achieve maximum efficiency. Once a multicellular infection has been established, even a very low level of MP is sufficient for the virus to spread locally at its maximum rate. The maximum rate of systemic spread requires less MP than is produced during a wild-type TMV infection, and long-distance movement may be directly influenced by the level of MP.

SUMMARY OF SEQUENCES

SEQ ID NO: 1 is an amino acid sequence for TMV coat protein.

SEQ ID NO: 2 is a nucleotide sequence encoding tobacco mosaic virus.

SEQ ID NO: 3 is the amino acid sequence for a truncated TMV MP (deletion mutant).

SEQ ID NO: 4 is a nucleotide sequence for a truncated TMV movement protein TAD26.

SEQ ID NO: 5 is a nucleotide sequence encoding TEV-NIa-based expression cassette PRO1.

SEQ ID NO: 6 is the deduced amino acid sequence for TEV-NIa-based expression cassette PRO1.

SEQ ID NO: 7 is an oligonucleotide primer for TMV U1.

SEQ ID NO: 8 is an oligonucleotide primer for TMV U1.

SEQ ID NO: 9 is an oligonucleotide primer for TMV U1.

SEQ ID NO: 10 is an amino acid sequence encoding a viral antigenic epitope of HIV gp 120.

SEQ ID NO: 11 is an amino acid sequence encoding a viral antigenic epitope of HIV gp 120.

SEQ ID NO: 12 is an amino acid sequence encoding a viral antigenic epitope of HIV gp 120.

SEQ ID NO: 13 is an amino acid sequence encoding a viral antigenic epitope of HIV gp 120.

SEQ ID NO: 14 is an amino acid sequence encoding a viral antigenic epitope of influenza virus hamaggluttin (12CA5).

SEQ ID NO: 15 is an amino acid sequence encoding an antigenic epitope of human c-myc (9E10).

SEQ ID NO: 16 is an amino acid sequence encoding an antigenic epitope of murine zona pellucida (ZP3).

SEQ ID NO: 17 is a nucleotide sequence for a PCR primer for the TMV cDNA infectious clone.

SEQ ID NO: 18 is a nucleotide sequence for a PCR primer for the TMV cDNA infectious clone.

SEQ ID NO: 19 is a nucleotide sequence for a PCR primer for the TMV cDNA infectious clone.

SEQ ID NO: 20 is a nucleotide sequence for a PCR primer for the TMV cDNA infectious clone.

SEQ ID NO: 21 is the amino acid sequence of a modified TMV CP containing a 15 amino acid epitope of HV gp 120 V3 loop inserted between amino acids 154 and 155 of the wild type TMV CP.

SEQ ID NO: 22 is the amino acid sequence of a modified TMV CP containing a 10 amino acid epitope of HIV gp 120 V3 loop inserted between amino acids 154 and 155 of the wild type TMV CP.

SEQ ID NO: 23 is the amino acid sequence of a modified TMV CP containing a 15 amino acid epitope of HIV gp 120 V3 loop inserted between amino acids 154 and 155 of the wild type TMV CP.

SEQ ID NO: 24 is the amino acid sequence of a modified TMV CP containing a 20 amino acid epitope of HIV gp 120 V3 loop inserted between amino acids 154 and 155 of the wild type TMV CP.

SEQ ID NO: 25 is the amino acid sequence for the wild type TMV movement protein.

SEQ ID NO: 26 is a nucleotide sequence for a PCR primer (T3) for the coat protein coding sequence of TMV strain U1.

SEQ ID NO: 27 is a nucleotide sequence for a PCR primer (T3) for the coat protein coding sequence of TMV strain U1.

SEQ ID NO: 28 is a nucleotide sequence for a PCR primer (T7) for the coat protein coding sequence of TMV strain U1.

SEQ ID NO: 29 is a nucleotide sequence for a PCR primer (T7) for the coat protein coding sequence of TMV strain U1.

SEQ ID NO: 30 is the amino acid sequence of the amino terminal cysteyl residue of the synthetic ZP peptide.

SEQUENCE LISTING (1) GENERAL INFORMATION:

(iii) NUMBER OF SEQUENCES: 30

(2) INFORMATION FOR SEQ ID NO:1:

(i) SEQUENCE CHARACTERISTICS:
      (A) LENGTH: 159 amino acids
      (B) TYPE: amino acid
      (D) TOPOLOGY: linear (ii) MOLECULE TYPE: protein (vii) IMMEDIATE SOURCE:
      (B) CLONE: TMV CP (xi) SEQUENCE DESCRIPTION: SEQ ID NO:1:

Met Ser Tyr Ser Ile Thr Thr Pro Ser Gln Phe Val Phe Leu Ser Ser
1               5                   10                  15

Ala Trp Ala Asp Pro Ile Glu Leu Ile Asn Leu Cys Thr Asn Ala Leu
            20                  25                  30

Gly Asn Gln Phe Gln Thr Gln Gln Ala Arg Thr Val Val Gln Arg Gln
        35                  40                  45

Phe Ser Glu Val Trp Lys Pro Ser Pro Gln Val Thr Val Arg Phe Pro
    50                  55                  60

Asp Ser Asp Phe Lys Val Tyr Arg Tyr Asn Ala Val Leu Asp Pro Leu
65                  70                  75                  80

Val Thr Ala Leu Leu Gly Ala Phe Asp Thr Arg Asn Arg Ile Ile Glu
            85                  90                  95

Val Glu Asn Gln Ala Asn Pro Thr Thr Ala Glu Thr Leu Asp Ala Thr
        100                 105                 110

Arg Arg Val Asp Asp Ala Thr Val Ala Ile Arg Ser Ala Ile Asn Asn
    115                 120                 125

Leu Ile Val Glu Leu Ile Arg Gly Thr Gly Ser Tyr Asn Arg Ser Ser
130                 135                 140

Phe Glu Ser Ser Ser Gly Leu Val Trp Thr Ser Gly Pro Ala Thr
145                 150                 155

(2) INFORMATION FOR SEQ ID NO:2:

(i) SEQUENCE CHARACTERISTICS:
      (A) LENGTH: 6395 base pairs
      (B) TYPE: nucleic acid
      (C) STRANDEDNESS: single
      (D) TOPOLOGY: linear (ii) MOLECULE TYPE: Genomic DNA (vii) IMMEDIATE SOURCE:
      (B) CLONE: TMV (xi) SEQUENCE DESCRIPTION: SEQ ID NO:2:

GTATTTTTAC AACAATTACC AACAACAACA AACAACAAAC AACATTACAA TTACTATTTA    60

CAATTACAAT GGCATACACA CAGACAGCTA CCACATCAGC TTTGCTGGAC ACTGTCCGAG   120

-continued

```
GAAACAACTC CTTGGTCAAT GATCTAGCAA AGCGTCGTCT TTACGACACA GCGGTTGAAG      180

AGTTTAACGC TCGTGACCGC AGGCCCAAGG TGAACTTTTC AAAAGTAATA AGCGAGGAGC      240

AGACGCTTAT TGCTACCCGG GCGTATCCAG AATTCCAAAT TACATTTTAT AACACGCAAA      300

ATGCCGTGCA TTCGCTTGCA GGTGGATTGC GATCTTTAGA ACTGGAATAT CTGATGATGC      360

AAATTCCCTA CGGATCATTG ACTTATGACA TAGGCGGGAA TTTTGCATCG CATCTGTTCA      420

AGGGACGAGC ATATGTACAC TGCTGCATGC CCAACCTGGA CGTTCGAGAC ATCATGCGGC      480

ACGAAGGCCA GAAAGACAGT ATTGAACTAT ACCTTTCTAG GCTAGAGAGA GGGGGGAAAA      540

CAGTCCCCAA CTTCCAAAAG GAAGCATTTG ACAGATACGC AGAAATTCCT GAAGACGCTG      600

TCTGTCACAA TACTTTCCAG ACAATGCGAC ATCAGCCGAT GCAGCAATCA GGCAGAGTGT      660

ATGCCATTGC GCTACACAGC ATATATGACA TACCAGCCGA TGAGTTCGGG GCGGCACTCT      720

TGAGGAAAAA TGTCCATACG TGCTATGCCG CTTTCCACTT CTCTGAGAAC CTGCTTCTTG      780

AAGATTCATA CGTCAATTTG GACGAAATCA ACGCGTGTTT TTCGCGCGAT GGAGACAAGT      840

TGACCTTTTC TTTTGCATCA GAGAGTACTC TTAATTATTG TCATAGTTAT TCTAATATTC      900

TTAAGTATGT GTGCAAAACT TACTTCCCGG CCTCTAATAG AGAGGTTTAC ATGAAGGAGT      960

TTTTAGTCAC CAGAGTTAAT ACCTGGTTTT GTAAGTTTTC TAGAATAGAT ACTTTTCTTT     1020

TGTACAAAGG TGTGGCCCAT AAAAGTGTAG ATAGTGAGCA GTTTTATACT GCAATGGAAG     1080

ACGCATGGCA TTACAAAAAG ACTCTTGCAA TGTGCAACAG CGAGAGAATC CTCCTTGAGG     1140

ATTCATCATC AGTCAATTAC TGGTTTCCCA AAATGAGGGA TATGGTCATC GTACCATTAT     1200

TCGACATTTC TTTGGAGACT AGTAAGAGGA CGCGCAAGGA AGTCTTAGTG TCCAAGGATT     1260

TCGTGTTTAC AGTGCTTAAC CACATTCGAA CATACCAGGC GAAAGCTCTT ACATACGCAA     1320

ATGTTTTGTC CTTTGTCGAA TCGATTCGAT CGAGGGTAAT CATTAACGGT GTGACAGCGA     1380

GGTCCGAATG GGATGTGGAC AAATCTTTGT TACAATCCTT GTCCATGACG TTTTACCTGC     1440

ATACTAAGCT TGCCGTTCTA AAGGATGACT TACTGATTAG CAAGTTTAGT CTCGGTTCGA     1500

AAACGGTGTG CCAGCATGTG TGGGATGAGA TTTCGCTGGC GTTTGGGAAC GCATTTCCCT     1560

CCGTGAAAGA GAGGCTCTTG AACAGGAAAC TTATCAGAGT GGCAGGCGAC GCATTAGAGA     1620

TCAGGGTGCC TGATCTATAT GTGACCTTCC ACGACAGATT AGTGACTGAG TACAAGGCCT     1680

CTGTGGACAT GCCTGCGCTT GACATTAGGA AGAAGATGGA AGAAACGGAA GTGATGTACA     1740

ATGCACTTTC AGAGTTATCG GTGTTAAGGG AGTCTGACAA ATTCGATGTT GATGTTTTTT     1800

CCCAGATGTG CCAATCTTTG GAAGTTGACC CAATGACGGC AGCGAAGGTT ATAGTCGCGG     1860

TCATGAGCAA TGAGAGCGGT CTGACTCTCA CATTTGAACG ACCTACTGAG GCGAATGTTG     1920

CGCTAGCTTT ACAGGATCAA GAGAAGGCTT CAGAAGGTGC TTTGGTAGTT ACCTCAAGAG     1980

AAGTTGAAGA ACCGTCCATG AAGGGTTCGA TGGCCAGAGG AGAGTTACAA TTAGCTGGTC     2040

TTGCTGGAGA TCATCCGGAG TCGTCCTATT CTAAGAACGA GGAGATAGAG TCTTTAGAGC     2100

AGTTTCATAT GGCAACGGCA GATTCGTTAA TTCGTAAGCA GATGAGCTCG ATTGTGTACA     2160

CGGGTCCGAT TAAAGTTCAG CAAATGAAAA ACTTTATCGA TAGCCTGGTA GCATCACTAT     2220

CTGCTGCGGT GTCGAATCTC GTCAAGATCC TCAAAGATAC AGCTGCTATT GACCTTGAAA     2280

CCCGTCAAAA GTTTGGAGTC TTGGATGTTG CATCTAGGAA GTGGTTAATC AAACCAACGG     2340

CCAAGAGTCA TGCATGGGGT GTTGTTAAAA CCCACGCGAG GAAGTATCAT GTGGCGCTTT     2400

TGGAATATGA TGAGCAGGGT GTGGTGACAT GCGATGATTG GAGAAGAGTA GCTGTCAGCT     2460

CTGAGTCTGT TGTTTATTCC GACATGGCGA AACTCAGAAC TCTGCGCAGA CTGCTTCGAA     2520
```

```
ACGGAGAACC GCATGTCAGT AGCGCAAAGG TTGTTCTTGT GGACGGAGTT CCGGGCTGTG    2580

GGAAAACCAA AGAAATTCTT TCCAGGGTTA ATTTTGATGA AGATCTAATT TTAGTACCTG    2640

GGAAGCAAGC CGCGGAAATG ATCAGAAGAC GTGCGAATTC CTCAGGGATT ATTGTGGCCA    2700

CGAAGGACAA CGTTAAAACC GTTGATTCTT TCATGATGAA TTTTGGGAAA AGCACACGCT    2760

GTCAGTTCAA GAGGTTATTC ATTGATGAAG GGTTGATGTT GCATACTGGT TGTGTTAATT    2820

TTCTTGTGGC GATGTCATTG TGCGAAATTG CATATGTTTA CGGAGACACA CAGCAGATTC    2880

CATACATCAA TAGAGTTTCA GGATTCCCGT ACCCCGCCCA TTTTGCCAAA TTGGAAGTTG    2940

ACGAGGTGGA GACACGCAGA ACTACTCTCC GTTGTCCAGC CGATGTCACA CATTATCTGA    3000

ACAGGAGATA TGAGGGCTTT GTCATGAGCA CTTCTTCGGT TAAAAAGTCT GTTTCGCAGG    3060

AGATGGTCGG CGGAGCCGCC GTGATCAATC CGATCTCAAA ACCCTTGCAT GGCAAGATCC    3120

TGACTTTTAC CCAATCGGAT AAAGAAGCTC TGCTTTCAAG AGGGTATTCA GATGTTCACA    3180

CTGTGCATGA AGTGCAAGGC GAGACATACT CTGATGTTTC ACTAGTTAGG TTAACCCCTA    3240

CACCAGTCTC CATCATTGCA GGAGACAGCC ACATGTTTT GGTCGCATTG TCAAGGCACA    3300

CCTGTTCGCT CAAGTACTAC ACTGTTGTTA TGGATCCTTT AGTTAGTATC ATTAGAGATC    3360

TAGAGAAACT TAGCTCGTAC TTGTTAGATA TGTATAAGGT CGATGCAGGA ACACAATAGC    3420

AATTACAGAT TGACTCGGTG TTCAAAGGTT CCAATCTTTT TGTTGCAGCG CCAAAGACTG    3480

GTGATATTTC TGATATGCAG TTTTACTATG ATAAGTGTCT CCCAGGCAAC AGCACCATGA    3540

TGAATAATTT TGATGCTGTT ACCATGAGGT TGACTGACAT TTCATTGAAT GTCAAAGATT    3600

GCATATTGGA TATGTCTAAG TCTGTTGCTG CGCCTAAGGA TCAAATCAAA CCACTAATAC    3660

CTATGGTACG AACGGCGGCA GAAATGCCAC GCCAGACTGG ACTATTGGAA AATTTAGTGG    3720

CGATGATTAA AAGGAACTTT AACGCACCCG AGTTGTCTGG CATCATTGAT ATTGAAAATA    3780

CTGCATCTTT AGTTGTAGAT AAGTTTTTTG ATAGTTATTT GCTTAAAGAA AAAAGAAAAC    3840

CAAATAAAAA TGTTTCTTTG TTCAGTAGAG AGTCTCTCAA TAGATGGTTA GAAAAGCAGG    3900

AACAGGTAAC AATAGGCCAG CTCGCAGATT TTGATTTTGT AGATTTGCCA GCAGTTGATC    3960

AGTACAGACA CATGATTAAA GCACAACCCA AGCAAAAATT GGACACTTCA ATCCAAACGG    4020

AGTACCCGGC TTTGCAGACG ATTGTGTACC ATTCAAAAAA GATCAATGCA ATATTTGGCC    4080

CGTTGTTTAG TGAGCTTACT AGGCAATTAC TGGACAGTGT TGATTCGAGC AGATTTTTGT    4140

TTTTCACAAG AAAGACACCA GCGCAGATTG AGGATTTCTT CGGAGATCTC GACAGTCATG    4200

TGCCGATGGA TGTCTTGGAG CTGGATATAT CAAAATACGA CAAATCTCAG AATGAATTCC    4260

ACTGTGCAGT AGAATACGAG ATCTGGCGAA GATTGGGTTT TGAAGACTTC TTGGGAGAAG    4320

TTTGGAAACA AGGGCATAGA AAGACCACCC TCAAGGATTA TACCGCAGGT ATAAAAACTT    4380

GCATCTGGTA TCAAAGAAAG AGCGGGGACG TCACGACGTT CATTGGAAAC ACTGTGATCA    4440

TTGCTGCATG TTTGGCCTCG ATGCTTCCGA TGGAGAAAAT AATCAAAGGA GCCTTTTGCG    4500

GTGACGATAG TCTGCTGTAC TTTCCAAAGG GTTGTGAGTT TCCGGATGTG CAACACTCCG    4560

CGAATCTTAT GTGGAATTTT GAAGCAAAAC TGTTTAAAAA ACAGTATGGA TACTTTTGCG    4620

GAAGATATGT AATACATCAC GACAGAGGAT GCATTGTGTA TTACGATCCC CTAAAGTTGA    4680

TCTCGAAACT TGGTGCTAAA CACATCAAGG ATTGGGAACA CTTGGAGGAG TTCAGAAGGT    4740

CTCTTTGTGA TGTTGCTGTT TCGTTGAACA ATTGTGCGTA TTACACACAG TTGGACGACG    4800

CTGTATGGGA GGTTCATAAG ACCGCCCCTC CAGGTTCGTT TGTTTATAAA AGTCTGGTGA    4860

AGTATTTGTC TGATAAAGTT CTTTTTAGAA GTTTGTTTAT AGATGGCTCT AGTTGTTAAA    4920
```

```
GGAAAAGTGA ATATCAATGA GTTTATCGAC CTGACAAAAA TGGAGAAGAT CTTACCGTCG    4980

ATGTTTACCC CTGTAAAGAG TGTTATGTGT TCCAAAGTTG ATAAAATAAT GGTTCATGAG    5040

AATGAGTCAT TGTCAGAGGT GAACCTTCTT AAAGGAGTTA AGCTTATTGA TAGTGGATAC    5100

GTCTGTTTAG CCGGTTTGGT CGTCACGGGC GAGTGGAACT TGCCTGACAA TTGCAGAGGA    5160

GGTGTGAGCG TGTGTCTGGT GGACAAAAGG ATGGAAAGAG CCGACGAGGC CACTCTCGGA    5220

TCTTACTACA CAGCAGCTGC AAAGAAAAGA TTTCAGTTCA AGGTCGTTCC CAATTATGCT    5280

ATAACCACCC AGGACGCGAT GAAAACGTC  TGGCAAGTTT TAGTTAATAT TAGAAATGTG    5340

AAGATGTCAG CGGGTTTCTG TCCGCTTTCT CTGGAGTTTG TGTCGGTGTG TATTGTTTAT    5400

AGAAATAATA TAAAATTAGG TTTGAGAGAG AAGATTACAA ACGTGAGAGA CGGAGGGCCC    5460

ATGGAACTTA CAGAAGAAGT CGTTGATGAG TTCATGGAAG ATGTCCCTAT GTCGATCAGG    5520

CTTGCAAAGT TTCGATCTCG AACCGGAAAA AAGAGTGATG TCCGCAAAGG GAAAAATAGT    5580

AGTAATGATC GGTCAGTGCC GAACAAGAAC TATAGAAATG TTAAGGATTT TGGAGGAATG    5640

AGTTTTAAAA AGAATAATTT AATCGATGAT GATTCGGAGG CTACTGTCGC CGAATCGGAT    5700

TCGTTTTAAA TATGTCTTAC AGTATCACTA CTCCATCTCA GTTCGTGTTC TTGTCATCAG    5760

CGTGGGCCGA CCCAATAGAG TTAATTAATT TATGTACTAA TGCCTTAGGA AATCAGTTTC    5820

AAACACAACA AGCTCGAACT GTCGTTCAAA GACAATTCAG TGAGGTGTGG AAACCTTCAC    5880

CACAAGTAAC TGTTAGGTTC CCTGACAGTG ACTTTAAGGT GTACAGGTAC AATGCGGTAT    5940

TAGACCCGCT AGTCACAGCA CTGTTAGGTG CATTCGACAC TAGAAATAGA ATAATAGAAG    6000

TTGAAAATCA GGCGAACCCC ACGACTGCCG AAACGTTAGA TGCTACTCGT AGAGTAGACG    6060

ACGCAACGGT GGCCATAAGG AGCGCGATAA ATAATTTAAT AGTAGAATTG ATCAGAGGAA    6120

CCGGATCTTA TAATCGGAGC TCTTTCGAGA GCTCTTCTGG TTTGGTTTGG ACCTCTGGTC    6180

CTGCAACTTG AGGTAGTCAA GATGCATAAT AAATAACGGA TTGTGTCCGT AATCACACGT    6240

GGTGCGTACG ATAACGCATA GTGTTTTTCC CTCCACTTAA ATCGAAGGGT TGTGTCTTGG    6300

ATCGCGCGGG TCAAATGTAT ATGGTTCATA TACATCCGCA GGCACGTAAT AAAGCGAGGG    6360

GTTCGAATCC CCCCGTTACC CCCGGTAGGG GCCCA                              6395

(2) INFORMATION FOR SEQ ID NO:3:

(i) SEQUENCE CHARACTERISTICS:
        (A) LENGTH: 64 amino acids
        (B) TYPE: amino acid
        (D) TOPOLOGY: linear (ii) MOLECULE TYPE: protein (vii) IMMEDIATE SOURCE:
        (B) CLONE: TMV MP (xi) SEQUENCE DESCRIPTION: SEQ ID NO:3:

Met Ala Leu Val Val Lys Gly Lys Val Asn Ile Asn Glu Phe Ile Asp
 1               5                  10                  15

Leu Thr Lys Met Glu Lys Ile Leu Pro Ser Met Phe Thr Pro Val Lys
                20                  25                  30

Ser Val Met Cys Ser Lys Val Asp Lys Ile Met Val His Glu Asn Glu
            35                  40                  45

Ser Leu Ser Glu Val Asn Leu Leu Lys Gly Val Lys Leu Ala Tyr Trp
        50                  55                  60

(2) INFORMATION FOR SEQ ID NO:4:
```

(i) SEQUENCE CHARACTERISTICS:
    (A) LENGTH: 36 base pairs
    (B) TYPE: nucleic acid
    (C) STRANDEDNESS: single
    (D) TOPOLOGY: linear (ii) MOLECULE TYPE: Genomic DNA (xi) SEQUENCE DESCRIPTION: SEQ ID NO:4:

TTAATCGATG ATGATTCGGT CGCCGAATCG GATTCG                                      36

(2) INFORMATION FOR SEQ ID NO:5:

(i) SEQUENCE CHARACTERISTICS:
        (A) LENGTH: 1488 base pairs
        (B) TYPE: nucleic acid
        (C) STRANDEDNESS: single
        (D) TOPOLOGY: linear (ii) MOLECULE TYPE: Genomic DNA (vii) IMMEDIATE SOURCE:
        (B) CLONE: PRO1

(ix) FEATURE:
        (A) NAME/KEY: CDS
        (B) LOCATION: 156...1481

(xi) SEQUENCE DESCRIPTION: SEQ ID NO:5:

```
GAGCTCAGAT CTAAATAACA AATCTCAACA CAACATATAC AAAACAAACG AATCTCAAGC           60

AATCAAGCAT TCTACTTCTA TTGCAGCAAT TTAAATCATT TCTTTTAAAG CAAAAGCAAT          120

TTTCTGAAAA TTTTCACCAT TTACGAACGA TAGCC ATG CCC GGG GAA CCA GTC             173
                                      Met Pro Gly Glu Pro Val
                                        1               5

TAT TTC CAA GGG AAG AAG AAT CAG AAG CAC AAG CTT AAG ATG AGA GAG            221
Tyr Phe Gln Gly Lys Lys Asn Gln Lys His Lys Leu Lys Met Arg Glu
            10                  15                  20

GCG CGT GGG GCT AGA GGG CAA TAT GAG GTT GCA GCG GAC GCA GGG GCG            269
Ala Arg Gly Ala Arg Gly Gln Tyr Glu Val Ala Ala Asp Ala Gly Ala
        25                  30                  35

CTA GAA CAT TAC TTT GGA AGC GCA TAT AAT AAC AAA GGA AAG CGC AAG            317
Leu Glu His Tyr Phe Gly Ser Ala Tyr Asn Asn Lys Gly Lys Arg Lys
    40                  45                  50

GGC ACC ACG AGA GGA ATG GGT GCA AAG TCT CGG AAA TTC ATA AAC ATG            365
Gly Thr Thr Arg Gly Met Gly Ala Lys Ser Arg Lys Phe Ile Asn Met
55                  60                  65                  70

TAT GGG TTT GAT CCA ACT GAT TTT TCA TAC ATT AGG TTT GTG GAT CCA            413
Tyr Gly Phe Asp Pro Thr Asp Phe Ser Tyr Ile Arg Phe Val Asp Pro
                75                  80                  85

TTG ACA GGT CAC ACT ATT GAT GAG TCC ACA AAC GCA CCT ATT GAT TTA            461
Leu Thr Gly His Thr Ile Asp Glu Ser Thr Asn Ala Pro Ile Asp Leu
            90                  95                 100

GTG CAG CAT GAG TTT GGA AAG GTT AGA ACA CGC ATG TTA ATT GAC GAT            509
Val Gln His Glu Phe Gly Lys Val Arg Thr Arg Met Leu Ile Asp Asp
        105                 110                 115

GAG ATA GAG CCT CAA AGT CTT AGC ACC CAC ACC ATC CAT GCT TAT            557
Glu Ile Glu Pro Gln Ser Leu Ser Thr His Thr Thr Ile His Ala Tyr
    120                 125                 130

TTG GTG AAT AGT GGC ACG AAG AAA GTT CTT AAG GTT GAT TTA ACA CCA            605
Leu Val Asn Ser Gly Thr Lys Lys Val Leu Lys Val Asp Leu Thr Pro
135                 140                 145                 150

CAC TCG TCG CTA CGT GCG AGT GAG AAA TCA ACA GCA ATA ATG GGA TTT            653
His Ser Ser Leu Arg Ala Ser Glu Lys Ser Thr Ala Ile Met Gly Phe
                155                 160                 165
```

```
CCT GAA AGG GAG AAT GAA TTG CGT CAA ACC GGC ATG GCA GTG CCA GTG      701
Pro Glu Arg Glu Asn Glu Leu Arg Gln Thr Gly Met Ala Val Pro Val
        170                 175                 180

GCT TAT GAT CAA TTG CCA CCA AAG AGT GAG GAC TTG ACG TTT GAA GGA      749
Ala Tyr Asp Gln Leu Pro Pro Lys Ser Glu Asp Leu Thr Phe Glu Gly
            185                 190                 195

GAA AGC TTG TTT AAG GGA CCA CGT GAT TAC AAC CCG ATA TCG AGC ACC      797
Glu Ser Leu Phe Lys Gly Pro Arg Asp Tyr Asn Pro Ile Ser Ser Thr
    200                 205                 210

ATT TGT CAC TTG ACG AAT GAA TCT GAT GGG CAC ACA ACA TCG TTG TAT      845
Ile Cys His Leu Thr Asn Glu Ser Asp Gly His Thr Thr Ser Leu Tyr
215                 220                 225                 230

GGT ATT GGA TTT GGT CCC TTC ATC ATT ACA AAC AAG CAC TTG TTT AGA      893
Gly Ile Gly Phe Gly Pro Phe Ile Ile Thr Asn Lys His Leu Phe Arg
                235                 240                 245

AGA AAT AAT GGA ACA CTG TTG GTC CAA TCA CTA CAT GGT GTA TTC AAG      941
Arg Asn Asn Gly Thr Leu Leu Val Gln Ser Leu His Gly Val Phe Lys
            250                 255                 260

GTC AAG AAC ACC ACG ACT TTG CAA CAA CAC CTC ATT GAT GGG AGG GAC      989
Val Lys Asn Thr Thr Thr Leu Gln Gln His Leu Ile Asp Gly Arg Asp
        265                 270                 275

ATG ATA ATT ATT CGC ATG CCT AAG GAT TTC CCA CCA TTT CCT CAA AAG     1037
Met Ile Ile Ile Arg Met Pro Lys Asp Phe Pro Pro Phe Pro Gln Lys
    280                 285                 290

CTG AAA TTT AGA GAG CCA CAA AGG GAA GAG CGC ATA TGT CTT GTG ACA     1085
Leu Lys Phe Arg Glu Pro Gln Arg Glu Glu Arg Ile Cys Leu Val Thr
295                 300                 305                 310

ACC AAC TTC CAA ACT AAG AGC ATG TCT AGC ATG GTG TCA GAC ACT AGT     1133
Thr Asn Phe Gln Thr Lys Ser Met Ser Ser Met Val Ser Asp Thr Ser
                315                 320                 325

TGC ACA TTC CCT TCA TCT GAT GGC ATA TTC TGG AAG CAT TGG ATT CAA     1181
Cys Thr Phe Pro Ser Ser Asp Gly Ile Phe Trp Lys His Trp Ile Gln
            330                 335                 340

ACC AAG GAT GGG CAG TGT GGC AGT CCA TTA GTA TCA ACT AGA GAT GGG     1229
Thr Lys Asp Gly Gln Cys Gly Ser Pro Leu Val Ser Thr Arg Asp Gly
        345                 350                 355

TTC ATT GTT GGT ATA CAC TCA GCA TCG AAT TTC ACC AAC ACA AAC AAT     1277
Phe Ile Val Gly Ile His Ser Ala Ser Asn Phe Thr Asn Thr Asn Asn
    360                 365                 370

TAT TTC ACA AGC GTG CCG AAA AAC TTC ATG GAA TTG TTG ACA AAT CAG     1325
Tyr Phe Thr Ser Val Pro Lys Asn Phe Met Glu Leu Leu Thr Asn Gln
375                 380                 385                 390

GAG GCG CAG CAG TGG GTT AGT GGT TGG CGA TTA AAT GCT GAC TCA GTA     1373
Glu Ala Gln Gln Trp Val Ser Gly Trp Arg Leu Asn Ala Asp Ser Val
                395                 400                 405

TTG TGG GGG GGC CAT AAA GTT TTC ATG AGC AAA CCT GAA GAG CCT TTT     1421
Leu Trp Gly Gly His Lys Val Phe Met Ser Lys Pro Glu Glu Pro Phe
            410                 415                 420

CAG CCA GTT AAG GAA GCG ACT CAA CTC ATG AGT GAA TTG GTG TAC TCG     1469
Gln Pro Val Lys Glu Ala Thr Gln Leu Met Ser Glu Leu Val Tyr Ser
        425                 430                 435

CAA GGG AGG CCT TGAATTC                                             1488
Gln Gly Arg Pro
440

(2) INFORMATION FOR SEQ ID NO:6:

(i) SEQUENCE CHARACTERISTICS:
        (A) LENGTH: 442 amino acids
        (B) TYPE: amino acid
        (D) TOPOLOGY: linear
```

(ii) MOLECULE TYPE: protein (v) FRAGMENT TYPE: internal (xi) SEQUENCE DESCRIPTION: SEQ ID NO:6:

```
Met Pro Gly Glu Pro Val Tyr Phe Gln Gly Lys Lys Asn Gln Lys His
 1               5                  10                  15

Lys Leu Lys Met Arg Glu Ala Arg Gly Ala Arg Gly Gln Tyr Glu Val
                20                  25                  30

Ala Ala Asp Ala Gly Ala Leu Glu His Tyr Phe Gly Ser Ala Tyr Asn
            35                  40                  45

Asn Lys Gly Lys Arg Lys Gly Thr Thr Arg Gly Met Gly Ala Lys Ser
        50                  55                  60

Arg Lys Phe Ile Asn Met Tyr Gly Phe Asp Pro Thr Asp Phe Ser Tyr
 65                  70                  75                  80

Ile Arg Phe Val Asp Pro Leu Thr Gly His Thr Ile Asp Glu Ser Thr
                85                  90                  95

Asn Ala Pro Ile Asp Leu Val Gln His Glu Phe Gly Lys Val Arg Thr
            100                 105                 110

Arg Met Leu Ile Asp Asp Glu Ile Glu Pro Gln Ser Leu Ser Thr His
        115                 120                 125

Thr Thr Ile His Ala Tyr Leu Val Asn Ser Gly Thr Lys Lys Val Leu
130                 135                 140

Lys Val Asp Leu Thr Pro His Ser Ser Leu Arg Ala Ser Glu Lys Ser
145                 150                 155                 160

Thr Ala Ile Met Gly Phe Pro Glu Arg Glu Asn Glu Leu Arg Gln Thr
                165                 170                 175

Gly Met Ala Val Pro Val Ala Tyr Asp Gln Leu Pro Pro Lys Ser Glu
            180                 185                 190

Asp Leu Thr Phe Glu Gly Glu Ser Leu Phe Lys Gly Pro Arg Asp Tyr
        195                 200                 205

Asn Pro Ile Ser Ser Thr Ile Cys His Leu Thr Asn Glu Ser Asp Gly
210                 215                 220

His Thr Thr Ser Leu Tyr Gly Ile Gly Phe Gly Pro Phe Ile Ile Thr
225                 230                 235                 240

Asn Lys His Leu Phe Arg Arg Asn Asn Gly Thr Leu Leu Val Gln Ser
                245                 250                 255

Leu His Gly Val Phe Lys Val Lys Asn Thr Thr Thr Leu Gln Gln His
            260                 265                 270

Leu Ile Asp Gly Arg Asp Met Ile Ile Ile Arg Met Pro Lys Asp Phe
        275                 280                 285

Pro Pro Phe Pro Gln Lys Leu Lys Phe Arg Glu Pro Gln Arg Glu Glu
290                 295                 300

Arg Ile Cys Leu Val Thr Thr Asn Phe Gln Thr Lys Ser Met Ser Ser
305                 310                 315                 320

Met Val Ser Asp Thr Ser Cys Thr Phe Pro Ser Ser Asp Gly Ile Phe
                325                 330                 335

Trp Lys His Trp Ile Gln Thr Lys Asp Gly Gln Cys Gly Ser Pro Leu
            340                 345                 350

Val Ser Thr Arg Asp Gly Phe Ile Val Gly Ile His Ser Ala Ser Asn
        355                 360                 365

Phe Thr Asn Thr Asn Asn Tyr Phe Thr Ser Val Pro Lys Asn Phe Met
370                 375                 380

Glu Leu Leu Thr Asn Gln Glu Ala Gln Gln Trp Val Ser Gly Trp Arg
```

```
                385                 390                 395                 400
Leu Asn Ala Asp Ser Val Leu Trp Gly Gly His Lys Val Phe Met Ser
                    405                 410                 415

Lys Pro Glu Glu Pro Phe Gln Pro Val Lys Glu Ala Thr Gln Leu Met
            420                 425                 430

Ser Glu Leu Val Tyr Ser Gln Gly Arg Pro
            435                 440
```

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:7:

GGTACCTGGG CCCCTACCGG GGTAACGGG        29

(2) INFORMATION FOR SEQ ID NO:8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:8:

GCTGCAGTAT TTTTACAACA ATTACC        26

(2) INFORMATION FOR SEQ ID NO:9:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:9:

GTAATACGAC TCACTATAGT ATTTTTACAA CAATTA        36

(2) INFORMATION FOR SEQ ID NO:10:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:10:

```
Arg Ile His Ile Gly Pro Gly Arg Ala Phe
 1               5                  10
```

(2) INFORMATION FOR SEQ ID NO:11:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:11:

Tyr Asn Lys Arg Lys Arg Ile His Ile Gly Pro Gly Arg Ala Phe
1               5                   10                  15

(2) INFORMATION FOR SEQ ID NO:12:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:12:

Arg Ile His Ile Gly Pro Gly Arg Ala Phe Tyr Thr Thr Lys Asn
1               5                   10                  15

(2) INFORMATION FOR SEQ ID NO:13:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:13:

Tyr Asn Lys Arg Lys Arg Ile His Ile Gly Pro Gly Arg Ala Phe Tyr
1               5                   10                  15

Thr Thr Lys Asn
            20

(2) INFORMATION FOR SEQ ID NO:14:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (vii) IMMEDIATE SOURCE:
        (B) CLONE: 12CA5

(xi) SEQUENCE DESCRIPTION: SEQ ID NO:14:

Tyr Pro Tyr Asp Val Pro Asp Tyr Ala
1               5

(2) INFORMATION FOR SEQ ID NO:15:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (vii) IMMEDIATE SOURCE:
        (B) CLONE: 9E10

(xi) SEQUENCE DESCRIPTION: SEQ ID NO:15:

Glu Gln Lys Leu Ile Ser Glu Glu Asp Leu
1               5                   10

(2) INFORMATION FOR SEQ ID NO:16:

(i) SEQUENCE CHARACTERISTICS:
        (A) LENGTH: 13 amino acids (B) TYPE: amino acid
        (D) TOPOLOGY: linear (ii) MOLECULE TYPE: peptide (vii) IMMEDIATE SOURCE:
        (B) CLONE: ZP3

(xi) SEQUENCE DESCRIPTION: SEQ ID NO:16:

Ser Ser Ser Ser Gln Phe Gln Ile His Gly Pro Arg Gln
 1               5                  10

(2) INFORMATION FOR SEQ ID NO:17:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:17:

CATATAGGAC CAGGAAGAGC CTTCGGTCCT GCAACTTGAG G                     41

(2) INFORMATION FOR SEQ ID NO:18:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:18:

ATTAACCCTC ACTAAAG                                                17

(2) INFORMATION FOR SEQ ID NO:19:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:19:

GGCTCTTCCT GGTCCTATAT GTATTCTAGA GGTCCAAACC AAAC                  44

(2) INFORMATION FOR SEQ ID NO:20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:20:

ATTAACCCTC ACTAAAG                                                17

(2) INFORMATION FOR SEQ ID NO:21:

(i) SEQUENCE CHARACTERISTICS:
        (A) LENGTH: 174 amino acids
        (B) TYPE: amino acid
        (D) TOPOLOGY: linear (ii) MOLECULE TYPE: protein (vii) IMMEDIATE SOURCE:
      (B) CLONE: TMV CP (xi) SEQUENCE DESCRIPTION: SEQ ID NO:21:

```
Met Ser Tyr Ser Ile Thr Thr Pro Ser Gln Phe Val Phe Leu Ser Ser
1               5                   10                  15

Ala Trp Ala Asp Pro Ile Glu Leu Ile Asn Leu Cys Thr Asn Ala Leu
            20                  25                  30

Gly Asn Gln Phe Gln Thr Gln Gln Ala Arg Thr Val Val Gln Arg Gln
        35                  40                  45

Phe Ser Glu Val Trp Lys Pro Ser Pro Gln Val Thr Val Arg Phe Pro
50                  55                  60

Asp Ser Asp Phe Lys Val Tyr Arg Tyr Asn Ala Val Leu Asp Pro Leu
65                  70                  75                  80

Val Thr Ala Leu Leu Gly Ala Phe Asp Thr Arg Asn Arg Ile Ile Glu
            85                  90                  95

Val Glu Asn Gln Ala Asn Pro Thr Thr Ala Glu Thr Leu Asp Ala Thr
            100                 105                 110

Arg Arg Val Asp Asp Ala Thr Val Ala Ile Arg Ser Ala Ile Asn Asn
            115                 120                 125

Leu Ile Val Glu Leu Ile Arg Gly Thr Gly Ser Tyr Asn Arg Ser Ser
130                 135                 140

Phe Glu Ser Ser Ser Gly Leu Val Trp Thr Ser Tyr Asn Lys Arg Lys
145                 150                 155                 160

Arg Ile His Ile Gly Pro Gly Arg Ala Phe Gly Pro Ala Thr
            165                 170
```

(2) INFORMATION FOR SEQ ID NO:22:

(i) SEQUENCE CHARACTERISTICS:
          (A) LENGTH: 169 amino acids
          (B) TYPE: amino acid
          (D) TOPOLOGY: linear (ii) MOLECULE TYPE: protein (vii) IMMEDIATE SOURCE:
          (B) CLONE: TMV CP (xi) SEQUENCE DESCRIPTION: SEQ ID NO:22:

```
Met Ser Tyr Ser Ile Thr Thr Pro Ser Gln Phe Val Phe Leu Ser Ser
1               5                   10                  15

Ala Trp Ala Asp Pro Ile Glu Leu Ile Asn Leu Cys Thr Asn Ala Leu
            20                  25                  30

Gly Asn Gln Phe Gln Thr Gln Gln Ala Arg Thr Val Val Gln Arg Gln
        35                  40                  45

Phe Ser Glu Val Trp Lys Pro Ser Pro Gln Val Thr Val Arg Phe Pro
50                  55                  60

Asp Ser Asp Phe Lys Val Tyr Arg Tyr Asn Ala Val Leu Asp Pro Leu
65                  70                  75                  80

Val Thr Ala Leu Leu Gly Ala Phe Asp Thr Arg Asn Arg Ile Ile Glu
            85                  90                  95

Val Glu Asn Gln Ala Asn Pro Thr Thr Ala Glu Thr Leu Asp Ala Thr
            100                 105                 110

Arg Arg Val Asp Asp Ala Thr Val Ala Ile Arg Ser Ala Ile Asn Asn
            115                 120                 125
```

```
Leu Ile Val Glu Leu Ile Arg Gly Thr Gly Ser Tyr Asn Arg Ser Ser
    130                 135                 140

Phe Glu Ser Ser Ser Gly Leu Val Trp Thr Ser Arg Ile His Ile Gly
145                 150                 155                 160

Pro Gly Arg Ala Phe Gly Pro Ala Thr
                165
```

(2) INFORMATION FOR SEQ ID NO:23:

(i) SEQUENCE CHARACTERISTICS:
        (A) LENGTH: 174 amino acids
        (B) TYPE: amino acid
        (D) TOPOLOGY: linear (ii) MOLECULE TYPE: protein (vii) IMMEDIATE SOURCE:
        (B) CLONE: TMV CP (xi) SEQUENCE DESCRIPTION: SEQ ID NO:23:

```
Met Ser Tyr Ser Ile Thr Thr Pro Ser Gln Phe Val Phe Leu Ser Ser
1                   5                  10                  15

Ala Trp Ala Asp Pro Ile Glu Leu Ile Asn Leu Cys Thr Asn Ala Leu
                20                  25                  30

Gly Asn Gln Phe Gln Thr Gln Gln Ala Arg Thr Val Val Gln Arg Gln
            35                  40                  45

Phe Ser Glu Val Trp Lys Pro Ser Pro Gln Val Thr Val Arg Phe Pro
 50                 55                  60

Asp Ser Asp Phe Lys Val Tyr Arg Tyr Asn Ala Val Leu Asp Pro Leu
65                  70                  75                  80

Val Thr Ala Leu Leu Gly Ala Phe Asp Thr Arg Asn Arg Ile Ile Glu
                85                  90                  95

Val Glu Asn Gln Ala Asn Pro Thr Thr Ala Glu Thr Leu Asp Ala Thr
                100                 105                 110

Arg Arg Val Asp Asp Ala Thr Val Ala Ile Arg Ser Ala Ile Asn Asn
            115                 120                 125

Leu Ile Val Glu Leu Ile Arg Gly Thr Gly Ser Tyr Asn Arg Ser Ser
    130                 135                 140

Phe Glu Ser Ser Ser Gly Leu Val Trp Thr Ser Arg Ile His Ile Gly
145                 150                 155                 160

Pro Gly Arg Ala Phe Tyr Thr Thr Lys Asn Gly Pro Ala Thr
                165                 170
```

(2) INFORMATION FOR SEQ ID NO:24:

(i) SEQUENCE CHARACTERISTICS:
        (A) LENGTH: 179 amino acids
        (B) TYPE: amino acid
        (D) TOPOLOGY: linear (ii) MOLECULE TYPE: protein (vii) IMMEDIATE SOURCE:
        (B) CLONE: TMV CP (xi) SEQUENCE DESCRIPTION: SEQ ID NO:24:

```
Met Ser Tyr Ser Ile Thr Thr Pro Ser Gln Phe Val Phe Leu Ser Ser
1                   5                  10                  15

Ala Trp Ala Asp Pro Ile Glu Leu Ile Asn Leu Cys Thr Asn Ala Leu
                20                  25                  30

Gly Asn Gln Phe Gln Thr Gln Gln Ala Arg Thr Val Val Gln Arg Gln
            35                  40                  45
```

```
Phe Ser Glu Val Trp Lys Pro Ser Pro Gln Val Thr Val Arg Phe Pro
     50                  55                  60

Asp Ser Asp Phe Lys Val Tyr Arg Tyr Asn Ala Val Leu Asp Pro Leu
 65                  70                  75                  80

Val Thr Ala Leu Leu Gly Ala Phe Asp Thr Arg Asn Arg Ile Ile Glu
                 85                  90                  95

Val Glu Asn Gln Ala Asn Pro Thr Thr Ala Glu Thr Leu Asp Ala Thr
                100                 105                 110

Arg Arg Val Asp Asp Ala Thr Val Ala Ile Arg Ser Ala Ile Asn Asn
             115                 120                 125

Leu Ile Val Glu Leu Ile Arg Gly Thr Gly Ser Tyr Asn Arg Ser Ser
130                 135                 140

Phe Glu Ser Ser Ser Gly Leu Val Trp Thr Ser Tyr Asn Lys Arg Lys
145                 150                 155                 160

Arg Ile His Ile Gly Pro Gly Arg Ala Phe Tyr Thr Thr Lys Asn Gly
                 165                 170                 175

Pro Ala Thr
```

(2) INFORMATION FOR SEQ ID NO:25:

(i) SEQUENCE CHARACTERISTICS:
        (A) LENGTH: 268 amino acids
        (B) TYPE: amino acid
        (D) TOPOLOGY: linear (ii) MOLECULE TYPE: protein (vii) IMMEDIATE SOURCE:
        (B) CLONE: TMV MPwt (xi) SEQUENCE DESCRIPTION: SEQ ID NO:25:

```
Met Ala Leu Val Val Lys Gly Lys Val Asn Ile Asn Glu Phe Ile Asp
 1               5                  10                  15

Leu Thr Lys Met Glu Lys Ile Leu Pro Ser Met Phe Thr Pro Val Lys
                 20                  25                  30

Ser Val Met Cys Ser Lys Val Asp Lys Ile Met Val His Glu Asn Glu
                 35                  40                  45

Ser Leu Ser Glu Val Asn Leu Leu Lys Gly Val Lys Leu Ile Asp Ser
 50                  55                  60

Gly Tyr Val Cys Leu Ala Gly Leu Val Val Thr Gly Glu Trp Asn Leu
 65                  70                  75                  80

Pro Asp Asn Cys Arg Gly Gly Val Ser Val Cys Leu Val Asp Lys Arg
                 85                  90                  95

Met Glu Arg Ala Asp Glu Ala Thr Leu Gly Ser Tyr Tyr Thr Ala Ala
                100                 105                 110

Ala Lys Lys Arg Phe Gln Phe Lys Val Val Pro Asn Tyr Ala Ile Thr
             115                 120                 125

Thr Gln Asp Ala Met Lys Asn Val Trp Gln Val Leu Val Asn Ile Arg
130                 135                 140

Asn Val Lys Met Ser Ala Gly Phe Cys Pro Leu Ser Leu Glu Phe Val
145                 150                 155                 160

Ser Val Cys Ile Val Tyr Arg Asn Asn Ile Lys Leu Gly Leu Arg Glu
                 165                 170                 175

Lys Ile Thr Asn Val Arg Asp Gly Gly Pro Met Glu Leu Thr Glu Glu
                 180                 185                 190

Val Val Asp Glu Phe Met Glu Asp Val Pro Met Ser Ile Arg Leu Ala
                 195                 200                 205
```

```
Lys Phe Arg Ser Arg Thr Gly Lys Lys Ser Asp Val Arg Lys Gly Lys
    210                 215                 220

Asn Ser Ser Asn Asp Arg Ser Val Pro Asn Lys Asn Tyr Arg Asn Val
225                 230                 235                 240

Lys Asp Phe Gly Gly Met Ser Phe Lys Lys Asn Asn Leu Ile Asp Asp
                245                 250                 255

Asp Ser Glu Ala Thr Val Ala Glu Ser Asp Ser Phe
            260                 265
```

(2) INFORMATION FOR SEQ ID NO:26:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:26:

```
GTCTTGGTCC GTGTATTTGG AATTGGAGCT ACTAGAAGAG GTCCAAACCA AAC          53
```

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:27:

```
AATAACCCTC ACTAAAGGGA                                               20
```

(2) INFORMATION FOR SEQ ID NO:28:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:28:

```
CCAAATACAC GGACCAAGAC AAGGTCCTGC AACTTGAGG                          39
```

(2) INFORMATION FOR SEQ ID NO:29:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:29:

```
TAATACGACT CACTATAGGG AGA                                           23
```

(2) INFORMATION FOR SEQ ID NO:30:

(i) SEQUENCE CHARACTERISTICS:
        (A) LENGTH: 13 amino acids
        (B) TYPE: amino acid
        (D) TOPOLOGY: linear -continued (ii) MOLECULE TYPE: peptide (xi) SEQUENCE DESCRIPTION: SEQ ID NO:30:

```
Cys Ser Ser Ser Ser Asn Gly His Pro Gln Phe Gln Arg
1               5                   10
```

The foregoing description of the invention is exemplary for purposes of illustration and explanation. It should be understood that various modifications can be made without departing from the spirit and scope of the invention. Accordingly, the following claims are intended to be interpreted to embrace all such modifications.

What is claimed is:

1. A method for producing a heterologous peptide in a plant comprising:
   a) infecting a TMV host plant with a CP modified infectious clone of TMV having a wild type MP gene and a wild type CP gene modified by insertion of a nucleotide sequence encoding a heterologous peptide of about 5 to about 20 amino acids between codons encoding amino acids 154 and 155;

b) culturing the plant under conditions to foster plant growth; and c) recovering the heterologous peptide from the leaves of the plant.

2. The method of claim 1 wherein the plant is a transgenic plant expressing a wild type TMV movement protein.

3. The method of claim 1 wherein the plant is further infected with a MP modified infectious clone of TMV having a wild type CP gene and an inactivated MP gene.

4. The method of claim 3 wherein the inactivated MP gene comprises SEQ ID NO:3.

5. The method of claim 3 wherein the inactivated MP gene comprises SEQ ID NO:4.

6. The method of claim 3 wherein the infecting is in a ratio of CP modified infectious clone to MP modified infectious clone of 1:1 to 10:1.

7. The method of claim 1 wherein the infecting is by viral transcripts produced in vitro.

8. The method of claim 1 wherein the host plant is selected from the group consisting of lettuce, spinach, tomato, potato, *Nicotiana tabacum. N. Glutinosa, N. Sylvester, Phaseolus vulgaris* and *Chenopodium amaranticolor.*

9. The method of claim 1 wherein the heterologous peptide comprises an antigenic epitope.

10. The method of claim 9 wherein the antigenic epitope is SEQ ID NO:14.

11. The method of claim 9 wherein the antigenic epitope is selected from the group consisting of SEQ ID NOS: 10, 11, 12 and 13.

12. The method of claim 9 wherein the antigenic epitope is SEQ ID NO: 16.

13. A method for producing an immune response stimulating peptide in a plant comprising:

a) infecting a TMV host plant with a CP modified infectious clone of TMV having a wild type MP gene and a wild type CP gene modified by insertion of a nucleotide sequence encoding an immune response stimulating peptide of about 5 to about 20 amino acids between codons encoding amino acids 154 and 155;

b) culturing the plant under conditions to foster plant growth; and c) recovering the immune response stimulating peptide from the leaves of the plant.

14. The method of claim 13 wherein the plant is a transgenic plant expressing a wild type MP gene.

15. The method of claim 13 wherein the nucleotide sequence encodes SEQ ID NO: 16.

16. The method of claim 13 wherein the plant is further infected with a MP modified infectious clone of TMV having a wild type CP gene and an inactivated MP gene.

17. The method of claim 16 wherein the infecting is in a ratio of CP modified infectious clone to MP modified infectious clone of 1:1 to 10:1.

18. The method of claim 17 wherein the inactivated MP gene comprises SEQ ID NO:3.

19. The method of claim 14 wherein the infecting is by viral transcripts produced in vitro.

20. The method of claim 14 wherein the host plant is selected from the group consisting of lettuce, spinach, tomato, potato, *Nicotiana tabacum, N. glutinosa, N. Sylvester, Phaseolus vulgaris* and *Chenopodium amaranticolor.*

21. The method of claim 14 wherein the immune response stimulating peptide comprises a viral antigenic epitope.

22. A nucleotide sequence encoding a CP modified infectious clone of TMV comprising a wild type MP gene and a wild type CP gene modified by insertion of a heterologous DNA sequence encoding a peptide of from about 5 to 20 amino acids between codons encoding amino acids 154 and 155.

23. The nucleotide sequence of claim 22 wherein the heterologous DNA sequence encodes a viral antigenic epitope.

24. The nucleotide sequence of claim 23 wherein the heterologous DNA sequence encodes a viral antigenic epitope of HIV gp 120.

25. The nucleotide sequence of claim 24 wherein the heterologous DNA sequence encodes a viral antigenic epitope of influenza hemagglutinin 12CA5.

26. The nucleotide sequence of claim 24 wherein the heterologous DNA sequence encodes an antigenic epitope of murine zona pellucida.

27. A nucleotide sequence encoding a modified infectious clone of TMV comprising a nucleotide sequence encoding a wild type coat protein and an inactivated movement protein, wherein the inactivated movement protein comprises SEQ ID NO:3.

28. A modified TMV virion comprising a heterologous peptide sequence of from about 5 to 20 amino acids inserted between amino acids 154 and 155 of a wild type TMV coat protein.

29. The virion of claim 28 wherein the heterologous peptide sequence is an antigenic epitope of zona pellucida 3.

30. The virion of claim 29 wherein the antigenic epitope is SEQ ID NO:16.

31. The virion of claim 29, wherein the antigenic epitope is SEQ ID NO:14.

32. A modified TMV virion comprising a wild type coat protein and an inactivated movement protein, wherein said movement protein comprises SEQ ID NO: 3.

33. A transgenic plant comprising the recombinant virion of claim 28.

* * * * *